US008124408B2

(12) United States Patent
Cai et al.

(10) Patent No.: US 8,124,408 B2
(45) Date of Patent: Feb. 28, 2012

(54) PREPARATION OF INACTIVATED ARTIFICIAL ANTIGEN PRESENTING CELLS AND THEIR USE IN CELL THERAPIES

(75) Inventors: Zeling Cai, San Diego, CA (US); Ann Moriarty, Poway, CA (US); Juli Degraw, San Diego, CA (US); Didier Leturcq, San Diego, CA (US); Wei-Xing Shi, San Diego, CA (US); Karen Kabat Stegman, Encinitas, CA (US); Xilian Yue, San Diego, CA (US)

(73) Assignee: Janssen Pharmaceutica N.V., Beerse (BE)

( * ) Notice: Subject to any disclaimer, the term of this patent is extended or adjusted under 35 U.S.C. 154(b) by 486 days.

(21) Appl. No.: 11/906,807

(22) Filed: Oct. 4, 2007

(65) Prior Publication Data

US 2009/0017000 A1 Jan. 15, 2009

Related U.S. Application Data

(60) Provisional application No. 60/849,299, filed on Oct. 4, 2006.

(51) Int. Cl.
*C12N 5/07* (2010.01)
*C12N 5/10* (2006.01)

(52) U.S. Cl. ............ 435/325; 435/348; 435/372.3; 435/374; 435/375

(58) Field of Classification Search .................. None
See application file for complete search history.

(56) References Cited

U.S. PATENT DOCUMENTS

| | | | |
|---|---|---|---|
| 4,690,915 A | 9/1987 | Rosenberg |
| 4,844,893 A | 7/1989 | Honsik et al. |
| 5,126,132 A | 6/1992 | Rosenberg |
| 5,314,813 A | 5/1994 | Peterson et al. |
| 5,443,983 A | 8/1995 | Ochoa et al. |
| 5,529,921 A | 6/1996 | Peterson et al. |
| 5,583,031 A | 12/1996 | Stern |
| 5,766,920 A | 6/1998 | Babbitt et al. |
| 5,827,737 A | 10/1998 | Peterson et al. |
| 5,846,827 A | 12/1998 | Celis et al. |
| 5,962,320 A | 10/1999 | Robinson |
| 6,001,365 A | 12/1999 | Peterson et al. |
| 6,040,177 A | 3/2000 | Riddell et al. |
| 6,194,205 B1 * | 2/2001 | Staege et al. ............ 435/373 |
| 6,194,207 B1 | 2/2001 | Bell |
| 6,204,058 B1 | 3/2001 | Bolton |
| 6,210,662 B1 | 4/2001 | Laus et al. |
| 6,210,963 B1 | 4/2001 | Haddada et al. |
| 6,225,042 B1 | 5/2001 | Cai et al. |
| 6,225,044 B1 | 5/2001 | Klein et al. |
| 6,227,368 B1 | 5/2001 | Truc |
| 6,251,385 B1 | 6/2001 | Terman |
| 6,251,627 B1 | 6/2001 | Cai et al. |
| 6,255,073 B1 | 7/2001 | Cai et al. |
| 6,355,479 B1 | 3/2002 | Webb et al. |
| 6,362,001 B1 | 3/2002 | Cai et al. |
| 6,461,867 B1 | 10/2002 | Cai et al. |
| 6,790,662 B1 | 9/2004 | Leturcq |
| 6,828,150 B2 | 12/2004 | Cai et al. |
| 2002/0119121 A1 | 8/2002 | Vitiello et al. |
| 2003/0022820 A1 | 1/2003 | Sherman |
| 2003/0072796 A1 | 4/2003 | Cai et al. |
| 2003/0077248 A1 | 4/2003 | Moriarty et al. |
| 2003/0170212 A1 | 9/2003 | Cai et al. |
| 2004/0071671 A1 | 4/2004 | Leturcq et al. |
| 2004/0147021 A1 | 7/2004 | Schuler et al. |
| 2004/0173778 A1 | 9/2004 | Roncarolo et al. |
| 2005/0054572 A1 | 3/2005 | Marshall |
| 2005/0152916 A1 | 7/2005 | Cai et al. |
| 2006/0134125 A1 | 6/2006 | Luxembourg et al. |
| 2006/0159667 A1 | 7/2006 | Fowler et al. |

FOREIGN PATENT DOCUMENTS

| | | |
|---|---|---|
| EP | 814838 | 5/2003 |
| WO | WO 91/06665 | 5/1991 |
| WO | WO 96/27392 | 9/1996 |
| WO | WO 96/39820 | 12/1996 |
| WO | WO 97/46256 | 12/1997 |
| WO | WO 00/54802 | 9/2000 |
| WO | WO 00/63690 | 10/2000 |
| WO | WO 02/022648 | 3/2002 |
| WO | WO 02/065992 | 8/2002 |
| WO | WO 02/092773 | 11/2002 |

OTHER PUBLICATIONS

Baccala et al., *J. Immunol.*, vol. 174, pp. 4606-4612 (2005).
Bakker et al., *J. Exp. Med.* vol. 179, pp. 1005-1009 (1994).
Belanger et al., 2000, *Transfusion* 40:1503, 2000).
*Biodrugs*, vol. 17(1), pp. 66-68 (2003).
Brichard et al., *J. Exp. Med.*, vol. 178:489-495, 1993.
Bunch et al.,1988, *Nucl. Acids Res.*, vol. 16, pp. 1043-1061.
Brockstedt et al., *Nat. Med.*, vol. 11(8), pp. 853-860 (2005).
Cai et al., *Immunol. Rev.*, vol. 165, pp. 249-265 (1998).
Carbonell et al., 1985, *J. Virol.* vol. 56, p. 153.
Carter et al., *Curr. Opin. Immunol.*, vol. 8(3), pp. 336-342 (1996).
Cerwenka et al., *J. Immunol.*, vol., 161, pp. 97-105 (1998).
Cerwenka et al., *J. Immunol.*, vol. 163(10), pp. 5535-5543 (1999).
Chatenoud et al., *J. Immunology*, 137(3):830-838 (1986). Croft et al., *J. Exp. Med.*, vol. 180, pp. 1715-1728 (1994).
Cutts et al., *Mol. Cancer. Ther.*, vol. 2(7), pp. 661-670 (2003).
Cai et al., 1996, *Proc. Natl. Acad. Sci. USA*, vol. 93, pp. 14736-14741.
Dronkert et al., *Mutat. Res.*, vol. 486(4), pp. 217-247 (2001).
DeSilva et al., 1999, *J. Immunol.*, vol. 163(8), pp. 4413-4420.
Dudley et al. at NCI (Dudley et al., *Science*, vol. 298, pp. 850-854 (2002).
Fraser, et al., 1989, *Cell. Dev. Biol.*, vol. 25, p. 225.
Fujihashi et al., *Proc. Natl. Acad. Sci. USA*, vol. 93, pp. 3613-3618 (1996).
Gaugler et al., *J. Exp. Med.* vol. 179, pp. 921-930 (1994).
Frankenberg-Schwager et al., *Toxicology*, vol. 212, pp. 175-184 (2005).
Faridi et al., *J. Biomol. Struct. Dyn.*, vol. 15(2), pp. 321-332 (1997).
Goldrath et al., *J. Exp. Med.*, vol. 192, pp. 557-564 (2000).
Hanson, *Blood Cells* 18:7, 1992.
Hears et al., *Virology*, vol. 101(1), pp. 124-130 (1980).

(Continued)

Primary Examiner — Karen Canella

(57) ABSTRACT

Methods of processing inactivated artificial antigen presenting cells (aAPCs) and artificial antigen presenting cells with specificity for selected antigenic peptides are described, including their generation and use in cell therapy compositions comprising activated cytotoxic T lymphocytes. Inactivated aAPCs are advantageously generated through crosslinking, such as via a photoreaction involving a psoralen derivative and UVA irradiation.

24 Claims, 23 Drawing Sheets

OTHER PUBLICATIONS

Herzig, *High-Dose Cancer Therapy: Pharmacology, Hematopoietins, Stem Cells* (Armitage and Antman, eds.), Williams and Wilkins (Baltimore), pp. 750-754(1992).
Hryniuk et al., *J. Clin. Oncol.* vol. 4, pp. 1162-1170 (1986.
Ishimaru et al., *Nature Immunol.*, vol. 7(7), pp. 763-772 (2006).
Jackson et al., *Proc. Natl Acad. Sci. USA*, vol. 89, pp. 12117-12121(1992).
Kaech et al., *Cell*, vol. 111, pp. 837-851 (2002).
Kang et al., *Nucleic Acids Res.*, vol., 24(20), pp. 3896-3902 (1996).
Kaufman et al., 1987, *EMBO J*, vol. 6, pp. 187-195.
Kawakami et al., *J. Exp. Med.*, vol. 180, 347-352 (1994).
Kern et al., *Eur. J. Immunol.*, vol. 29, pp. 2908-2915 (1999).
Kieper et al., *Proc. Natl. Acad. Sci. USA*, vol. 96, pp. 13306-13311 (1999).
Kieper et al., *J. Immunol.*, vol. 174, pp. 3157-3163 (2005).
Kim et al., *Nature Biotechnology*, vol. 22(4), pp. 403-410 (2004).
Leturcq et al., "Ex Vivo Generation of Potent Cytotoxic T Lymphocytes for the Treatment of Cancer: A Novel Antigen Presentation System", J Immunother, vol. 25, No. 6, S33, 2002, Society of Biological Therapy 17$^{th}$ Annual Meeting, Abstract #40.
Lin et al.,1989, *Blood*, vol. 74, pp. 517-525.
Livingston et al., *Immunol. Invest.*, vol. 24(4), pp. 619-629 (1995).
Ljunggren et al., 1990, *Nature*, vol. 346(6283), pp. 476-480.
Lubaki et al., *AIDS Res. Hum. Retrovirusus*, vol. 10(11), pp. 1427-1431 (1994).
Latouche et al., 2000, *Nat. Biotechnol.*, vol. 18, pp. 405-409.
Lin et al., *Transfusion*, vol. 37(4), pp. 423-435 (1997).
McFarland et al., *PNAS*, vol. 97(8), pp. 4215-4220 (2000).
Merrifield, *J. American Chemical Society*, vol. 85, pp. 2149-2154 (1963).
Mitchell et al., "Specific Immunotherapy of Cancer with Vaccines", *Ann. N. Y. Acad. Sci.* (Bystryn et al., eds.), pp. 153-166 (1993.
Mitchell et al., *J. Clin. Oncol.*, vol. 12, pp. 402-411 (1994).
Neidle et al., eds., S Molecular Aspects of Anticancer Drug-DNA Interactions. vol. 2, pp. 313-349 (1994).
Mosbach et al., 1983, *Nature* 302:543-545).
Mosmann et al., *Immunol. Today*, vol. 17(3), pp. 138-146 (1996).
Murali-Krishna et al., *J. Immunol.*, vol. 165, pp. 1733-1737 (2000).
Oelke et al., *Nat. Med.*, vol. 9:619-624(2003).
Oelke et al., *TRENDS in Molecular Medicine*, vol. 11(9), pp. 412-420 (2005).
Opferman et al., *Science*, vol. 283, pp. 1745-1748 (1999).
Palva et al., 1983, *Gene* 22:229-235.
Physicians' Desk Reference, pp. 1553-1554 (1990).
Quan et al, "Principles of Biologic Therapy," *Cancer Treatment* (Haskell, ed.) Philadelphia: W.B. Saunders (Philadelphia), pp. 57-69 (1995).
Redfield et al., *Infect. Immun.*, vol. 32(3), pp. 1216-1226.
Reinherz et al., Cell, 19(4):821-827 (1980).
Rubin et al., *Biological Approaches to Cancer Treatment. Biomodulation* (Mitchell, ed.), McGraw-Hill (New York), pp. 379-410 (1993).
Robbins et al., *Cancer Res.* 54:3124-3126, 1994.
Reedijk, *Proc. Natl. Acad. Sci. USA*, vol. 100(7), pp. 3611-3616 (2003).
Sad et al., *Immunity*, vol. 2, pp. 271-279 (1995).
Sancar et al., *Annu. Rev. Biochem.*, vol. 73, pp. 39-85 (2004).
Schneider, 1972, *J. Embryol. Exp. Morph .*, vol. 27, pp. 353-365.
Schneider et al., *Photochem. Photobiol.*, vol. 67(3), pp. 350-357 (1998).
Schoenberger et al., 1998, *Cancer Res.*, vol. 58, pp. 3094-3100.
Schumacher et al., 1990, *Cell*, vol. 62(3), pp. 563-567.
Scott et al., *Cell*, vol. 33(3), pp. 929-941 (1980).
Seed, 1987, *Nature*, vol. 329, p. 840.
Shwed et al., Virology, Vol. 296(2), pp. 241-250 (2002.
Smith el al., 1983, *Mol. Cell. Biol.*, vol. 3, p. 2156.
Sun et al., *Immunity*, vol. 4, pp. 555-564 (1996).
Tizard, I., Immunology: An Introduction, 3$^{rd}$ Edition, pp. 129-143 (1992).
Thorn et al., *J.Immunol. Methods.*, 4(2), pp. 301-315 (1974).
Tuite et al., *Eur. J. Biochem.*, vol. 243(1-2), pp. 482-492 (1997).
Walzer et al., *Cell. Immunol.*, vol. 206, pp. 16-25 (2000).
Warren et al., *Environ. Mol. Mutagen.*, vol. 31(1), pp. 70-81 (1998).
Van der Bruggen et al., *Science*, vol. 254, pp. 1643-1647 (1991).
Visseren et al., *J. Immunol.* vol. 154, pp. 3991-3998 (1995).
Watson et al., *AIDS Res Hum Retroviruses* 6:503, 1990).
Wherry et al., *Nat. Immunol.*, vol. 4, pp. 225-234 (2003.
Wright, 1986, *Nature*, vol. 321, p. 718.
Wolfel et al., *Eur. J. Imnnol.* vol. 24, pp. 759-764 (1994).
Yee et al., *PNAS*, vol. 99, pp. 16168-16173, (2002).
International Search Report re: PCT/US2007/021326 dated Nov. 3, 2008.

* cited by examiner

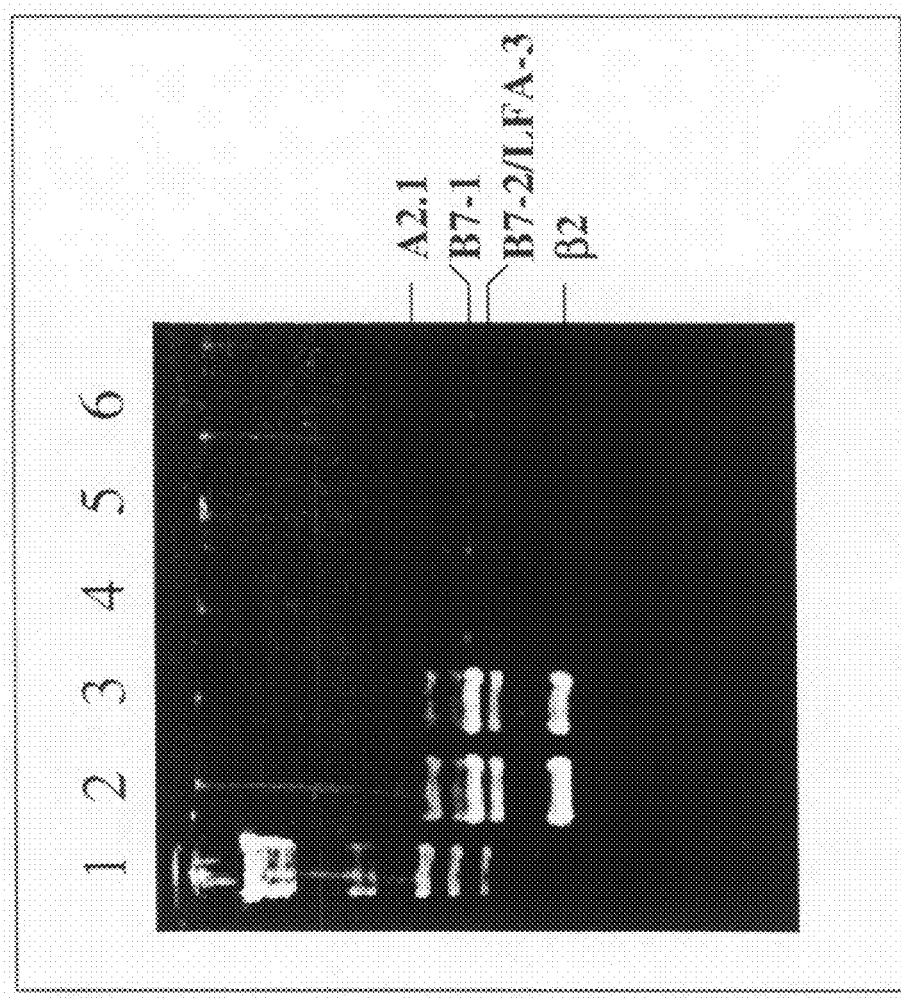

5 μg/ml UVADEX™ + 10 min UVA

Untreated

PREPARATION OF INACTIVATED ARTIFICIAL ANTIGEN PRESENTING CELLS AND THEIR USE IN CELL THERAPIES

CROSS-REFERENCE TO RELATED APPLICATIONS

This application claims the benefit of provisional patent application No.: 60/849,299, entitled "Preparation of Inactivated Artificial Antigen Presenting Cells and their Use in Cell Therapies" filed Oct. 4, 2006.

FIELD OF THE INVENTION

The present invention generally relates to methods for processing cell therapies for treating a disease, disorder, or medical condition, such as cancer, through inactivation of artificial APCs via crosslinking.

BACKGROUND OF THE INVENTION

To facilitate an appreciation of the invention, this section may discuss the historical and technical background leading to the development of the invention, including observations, conclusions, and viewpoints that may be unique to an inventor. Accordingly, the background statements herein should not be construed as an admission regarding the content of the prior art.

A number of therapies have been developed to treat a variety of cancers. Many of these efforts have centered around chemotherapeutic regimens. In one particular combination chemotherapy regimen designed as a treatment for metastatic melanoma, response rates of 35-50% were reported with the "Dartmouth regimen" (a combination of DTIC, cisplatin, BCNU, and tamoxifen), but the duration of survival has remained at 6 to 10 months. High rates of remission also have been reported for aggressive high-dose intensity chemotherapy (Hryniuk et al., *J. Clin. Oncol.* Vol. 4, pp. 1162-1170 (1986)) and repletion of hematopoeisis with autologous bone marrow transplants. Nevertheless, the median duration of survival was short, approximately four months (Herzig, *High-Dose Cancer Therapy: Pharmacology Hematopoietins, Stem Cells* (Armitage and Antman, eds.), Williams and Wilkins (Baltimore), pp. 750-754 (1992)).

Significant improvements in survival on the order of several years have been noted in a small percentage of melanoma patients undergoing certain immunotherapies. Immunotherapies have included active specific immunotherapy with cancer vaccines, as well as the use of nonspecific boosters of the immune system, such as interleukin-2 (IL-2) and interferon-alpha (IFN-α) (Mitchell et al., "Specific Immunotherapy of Cancer with Vaccines", *Ann. N.Y. Acad. Sci.* (Bystryn et al., eds.), pp. 153-166 (1993); Quan et al, "Principles of Biologic Therapy," *Cancer Treatment* (Haskell, ed.) Philadelphia: W. B. Saunders (Philadelphia), pp. 57-69 (1995); Mitchell et al., *J. Clin. Oncol.*, Vol. 12, pp. 402-411 (1994)). See also United States Patent Application Publication No. US 2003/0022820.

The identification of T-cell defined tumor antigens in melanoma has led to clinical trials that target cancer cells by attempting to augment the antigen-specific cellular immune response. This approach has been pursued in numerous vaccination strategies in which the antigens are delivered in an immunogenic context in an attempt to induce potent T cell responses in vivo. Although some clinical responses have been observed in the vaccine trials, the magnitude of the induced T-cell response has generally been low, or undetectable and correlated poorly with clinical responses. Immunization of melanoma patients with cancer antigens may increase the number of circulating CTL precursors; however it has not correlated with clinical tumor regression, suggesting a defect in function or activation in vivo.

Studies in mouse tumor models have demonstrated that adoptive immunotherapy, which involves in vitro immunization of T cells specific for one or more tumor antigens, may be efficacious with minimal toxicity. An obstacle in applying this strategy to the treatment of human tumors has been the identification of immunogenic antigens that render the tumor cells susceptible to CTL-mediated destruction. The isolation of tumor-reactive T cells from melanoma patients has led to the identification of some of the tumor antigens (epitopes) to which CTLs are directed. These include tyrosinase, MART-1/Melan A, gp 100, and MAGE. Of these, tyrosinase and MART-1 are nearly universally expressed on melanoma and therefore represent a desired target choice for adoptive immunotherapy (Van der Bruggen et al., *Science*, Vol. 254, pp. 1643-1647 (1991); Gaugler et al., *J. Exp. Med.* Vol. 179, pp. 921-930 (1994); Kawakami et al., *J. Exp. Med.*, Vol. 180, 347-352 (1994); Brichard et al., *J. Exp. Med.*, Vol. 178:489-495, 1993; Robbins et al., *Cancer Res.* 54:3124-3126, 1994; Bakker et al., *J. Exp. Med.* Vol. 179, pp. 1005-1009 (1994); Wolfel et al., *Eur. J. Immunol.* Vol. 24, pp. 759-764 (1994); and Visseren et al., *J. Immunol.* Vol. 154, pp. 3991-3998 (1995)).

Adoptive T cell therapy involves the removal of T cells from the host environment where tolerogenic mechanisms are active in vivo in cancer patients and contributes to the ineffective responses demonstrated in this patient population. $CD8^+$ T cells may be stimulated ex vivo to generate antigen-specific CTLs (see, e.g., U.S. Pat. No. 6,225,042). Early adoptive immunotherapy approaches employed activated lymphocytes as a treatment for various cancers (Rubin et al., *Biological Approaches to Cancer Treatment. Biomodulation* (Mitchell, ed.), McGraw-Hill (New York), pp. 379-410 (1993)). Initially, lymphokine-activated killer cells (LAK), and later tumor-infiltrating lymphocytes (TIL), activated ex vivo with IL-2, were used, but the demonstration of efficacy was equivocal. These early controlled clinical trials failed to show an advantage to the use of the ex vivo-activated cells over the direct administration of IL-2 to melanoma patients. More recent studies by Yee et al. at Fred Hutchinson Cancer Research Center (Yee et al., *PNAS*, Vol. 99, pp. 16168-16173, (2002)) and Dudley et al. at NCI (Dudley et al., *Science*, Vol. 298, pp. 850-854 (2002)) have demonstrated the potential for certain adoptive T-cell therapeutic approaches. These studies involved use of either T-cell clones specific for MART-1 or gp100 and low-dose IL-2, or TILs expanded ex vivo with allogeneic feeder cells and high-dose IL-2. These studies confirmed that adoptive immunotherapy holds promise as a treatment of cancer, although its full development has been impeded by the lack of reproducible methods for ex vivo generation of therapeutic numbers of antigen-specific $CD8^+$ CTLs (Oelke et al., *Nat. Med.*, Vol. 9:619-624 (2003)).

Cytolytic, or cytotoxic, $CD8^+$ T cells are a major line of defense against viral infections. $CD8^+$ lymphocytes specifically recognize and lyse host cells that are infected with a virus. Although it would be desirable to harness the cytotoxic activity of CTLs, few in vitro/ex vivo procedures have been available to specifically activate CTLs. The identification of key melanoma-associated antigens and a method for specific in vitro activation of CTLs, allows for an efficient evaluation of adoptive immunotherapy for metastatic melanoma (see, in addition to Yee et al., Dudley et al., and Oelke et al., supra, and Leturcq et al., "Ex Vivo Generation of Potent Cytotoxic T Lymphocytes for the Treatment of Cancer: A Novel Antigen Presentation System", *Society of Biological Therapy* 17*th* *Annual Meeting*, Abstract #40 (2002)).

While it is possible to use naturally occurring antigen presenting cells (APCs) for naïve T cell activation in vitro (e.g., dendritic cells, macrophages, B-cells, or autologous tumor cells), the efficiency of activation is low since the MHC molecules of native APCs contain many other peptide epitopes, thus allowing minimal presentation of selected epitopes. Most of these presented peptides represent normal, innocuous endogenous proteins. A more direct approach to this problem would be to activate CD8+ T cells specifically to those epitopes relevant to combating the disease.

One artificial APC which is an xAPC has been developed utilizing a *Drosophila melanogaster* (fruit fly) embryonic cell line, which expresses the major histocompatibility complex (MHC) Class I molecules (Letureq et al., supra; Jackson et al., *Proc. Natl. Acad. Sci. USA*, Vol. 89, pp. 12117-12121 (1992); see also U.S. Pat. Nos. 6,225,042 and 6,355,479). Since *Drosophila* lacks an advanced immune system, *Drosophila* homologues to human TAP-1 and 2 peptide transporters, which are involved in the loading of peptide epitopes into the human MHC molecules, are absent. Hence, transfected Class I molecules and Class II molecules appear on the *Drosophila* cell surface as empty vessels. By incubating *Drosophila* cells transfected with MHC Class I- or MHC Class II-encoding expression vectors with exogenous synthetic peptides that bind to the specific MHC molecules (i.e., tumor antigen T-cell peptide epitopes), all of the available MHC molecules may be occupied with MHC-restricted, specific peptide epitope(s). In particular, the high density expression of MHC Class I molecules presenting single or multiple epitopes, and the addition of key co-stimulatory molecules B7-1 (CD80), CD70, LFA-3 (CD58), and ICAM-1 (CD54) on these *Drosophila* APCs, may permit the in vitro generation of potent, autologous cytotoxic CD8+ T cells which are specific for the selected peptides (Cai et al., *Immunol. Rev.*, Vol. 165, pp, 249-265 (1998).

Various improvements in cell therapies have been developed. See, e.g., the following patent publications: U.S. Pat. Nos. 5,314,813, 5,529,921, 5,827,737, 6,001,365, 6,225,042, 6,251,627, 6,255,073, 6,362,001, 6,461,867, 6,790,662, and 6,828,150; WO 2002/065992 and 2002/092773; and EP 814, 838. For example, three clinical studies (referred to as CTL-01, CTL-02, and CTL-03) in advanced malignant melanoma patients have been conducted where autologous CD8+ T cells are isolated from the patients, stimulated and expanded ex vivo, before being returned to the patients as antigen-specific cytotoxic T lymphocytes (CTLs). The ability to reproducibly generate potent antigen-specific CTLs ex vivo involves a primary stimulation with an embryonic *Drosophila melanogaster* cell line (SC2) that is transfected with human HLA class I, co-stimulatory and adhesion molecules which are important for optimum T cell activation. The transfected cells are used as artificial antigen presenting cells to stimulate naïve CD8+ T cells to drive them to effector cells with cytotoxic activity against target cells, which express the protein to which the CTLs were immunized against in vitro. Two different artificial APC lines have been used in these clinical studies. One expressing HLA-A2, B7.1 and ICAM (clone 666), and the other expressing these same three molecules, plus B7.2 and LFA-3 (clone 668).

A cell therapy product designated CTL-04, which is undergoing clinical investigation, has been developed with the *Drosophila*-based APCs. The cell therapy product is an autologous immunotherapeutic product prepared with ex vivo-activated autologous CD8+ CTLs exhibiting peptide specificity to up to six selected HLA-A2.1-restricted peptides from melanoma-associated antigens identified by the sequences, listed in SEQ ID NOS:5, 6, 7, 8, 9, and 70. The active component of the cell therapy product is the patient's own CD8+ cells, which have been activated ex vivo by exposure to selected peptide-loaded aAPCs having specificity for at least one of the six HLA-A2.1 restricted peptides listed in the SEQ ID NOS. provided above. These CTLs are: derived from autologous naïve T cells isolated from lymphapheresis samples harvested at a clinical site; primed ex vivo against melanoma antigenic peptide epitopes using artificial, inactivated *Drosophila* cells as the APCs; expanded by restimulation with autologous monocytes loaded with the melanoma antigenic epitopes in the presence of Interleukin-2 (IL-2) and Interleukin-7 (IL-7), followed by non-specific expansion using OKT®3; harvested, washed, and re-suspended in final formulation for infusion; and infused into the patient. The final product for re-infusion contains $1-10 \times 10^9$ CTL cells in 300 mL of Lactated Ringer's Injection Solution (76% v/v), 5% dextrose in normal saline (D5NS) (4% v/v), and human serum albumin (HSA) (20% v/v).

Of course, as with any drug, it is important to ensure safety and efficacy of the therapeutic product. Thus, before a cell therapy product such as CTL-04 is released for clinical use, it is typically subjected to various quality assurance tests. For example, the cell therapy product may be tested to confirm absence of *Drosophila* DNA by a PCR-based technique. Additionally, the product may be subjected to RT/PCR to confirm absence of known endogenous insect-specific RNA viruses, such as *Drosophila* Nodavirus (DrNV); *Drosophila* X virus (DXV), and *Drosophila* HPS-1-like virus. Furthermore, the BacT/Alert® may be used to test in-process and final product sterility. The sterility testing of cell products by the NIH Department of Transfusion Medicine for fungal, bacterial, and endotoxin content is mentioned in U.S. Patent Application Publication No. US 2006/0159667.

Notwithstanding the safety and efficacy of such cell therapies, there remains a desire to further develop cell therapies that are further assured as being safe and potent, especially in light of the FDA reclassifying such a cell therapy as a xenotransplantation product. This classification requires a separate set of guidelines, which includes specific mention of the drug as a xenotransplantation product, possible risk of zoonotic infections to both the recipient and close physical contacts, prevention of organ or blood donations after receiving the treatment, and the establishment of a long term monitoring program to determine if late toxicity occurs as a result of the therapy.

SUMMARY OF THE INVENTION

The invention is directed to the general and preferred embodiments defined, respectively, by the independent and dependent claims appended hereto, which for the sake of brevity are incorporated by reference herein. Other preferred embodiments, features, and advantages of the various aspects of the invention will become apparent from the detailed description below taken in conjunction with the appended drawing figures.

In one embodiment, this invention relates to a method for creating activated T lymphocytes ex vivo for administration to a patient, comprising the steps of: inactivating artificial antigen presenting cells (aAPCs) with a nucleic acid crosslinking agent; contacting T lymphocytes isolated from a patient diagnosed with a disease or disorder with said inactivated artificial antigen presenting cells; and collecting the T lymphocytes for administration back to the patient. In one aspect of this embodiment, the crosslinking agent is a psoralen derivative and said inactivating step comprises exposing the artificial antigen presenting cells treated with the psoralen derivative to a photoactivating dose of UVA irradiation. Preferably the psoralen derivative is psoralen, 8-methoxypsoralen (8-MOPS), 4'-(aminomethyl)-4,5',8-psoralen (AMT), or amotosalen (S59). Also preferably where the crosslinking agent is a psoralen derivative, the inactivating step comprises exposing the artificial antigen presenting cells treated with the psoralen derivative at a concentration of from 1 to 100 µg/ml to UVA irradiation at a dose of from 1 to 100 Joule/cm$^2$ UVA irradiation for a period of from 1 to 60 minutes.

The methods of this embodiment are useful in the ex vivo methods for treating cancer and exemplary cancers contemplated within the scope of this invention and these methods further include the steps of loading the artificial antigen presenting cells with at least one cancer-associated peptide antigen. Further, the activated T lymphocytes are preferably cytotoxic toward target cells expressing the peptide, and the peptide is selected from the group consisting of melanoma cancer-associated peptide antigens, ovarian cancer-associated peptide antigens, breast cancer-associated peptide antigens, lung cancer-associated peptide antigens, leukemia-, multiple myeloma- and lymphoma-associated peptide antigens, and prostate cancer-associated peptide antigens. Preferred peptides are those that comprise at least eight contiguous antigenic amino acids of the amino acid sequence of MART-1, tyrosinase, gp100, NY-ESO-1, MUC-1, CA-125, Her-2, survivin, telomerase, CAMEL, CEA, livin, SART-1, SCP-1, SSX-2, PRAME, C-Lectin, Pec60, AES, MAGE-3, G250, FBP, SSX-4, SP17, hTRT, MUC-16, MAGE-1, Topoisomerase II, Integrin β8 subunit precursor, MUC-1, MAGE-B2, STAT 1, γ-Catenin, or H-RYK. Still more preferred is the use of one or more of the peptides selected from the group consisting of: SILSLKEAST (SEQ ID NO:1), KMASRSMRL (SEQ ID NO:2), ALALAALLVV (SEQ ID NO: 3), ALLVVDREV (SEQ ID NO: 4), YMNGTMSQV (SEQ ID NO:5), YMDGTMSQV (SEQ ID NO:6), ITDQVPFSV (SEQ ID NO:7), YLEPGPVTA (SEQ ID NO:8), AAGIGILTV (SEQ ID NO:9), ELAGIGILTV (SEQ ID NO:10), CLTSTVQLV (SEQ ID NO:11), HLYQGCQVV (SEQ ID NO:12), KIFGSLAFL (SEQ ID NO:13), IISAVVGIL (SEQ ID NO:14), PLTSIISAV (SEQ ID NO:15), VMAGVGSPYV (SEQ ID NO:16), VLVKSPNHV (SEQ ID NO:17), ELVSEFSRM (SEQ ID NO:18), YLSGANLNL (SEQ ID NO:19), GPLTPLPV (SEQ ID NO:20), SLLMWITQC (SEQ ID NO:21), KALFAGPPV (SEQ ID NO:22), YLETFREQV (SEQ ID NO:23), GLQSPKSPL (SEQ ID NO:24), VLLKLRRPV (SEQ ID NO:25), ELYIPSVDL (SEQ ID NO:26), SLLMWITQV (SEQ ID NO:27), ILAKFLHWL (SEQ ID NO:28), STAPPVHNV (SEQ ID NO:29), FLWGPRALV (SEQ ID NO:30), FMWGNLTLA (SEQ ID NO:31), RLVDDFLLV (SEQ ID NO:32), HLSTAFARV (SEQ ID NO:33), QLSLLMWIT (SEQ ID NO:34), ELWTHSYKV (SEQ ID NO:35), KVAELVHFL (SEQ ID NO:36), YIFATCLGL (SEQ ID NO:37), HLYIFATCL (SEQ ID NO:38), MLMAQEALAFL (SEQ ID NO:39), STLEKINKT (SEQ ID NO:40), KASEKIFYV (SEQ ID NO:41), SLLMWITQCFL (SEQ ID NO:42), ELTLGEFLKL (SEQ ID NO:43), LTLGEFLKL (SEQ ID NO:44), SLLEKREKT (SEQ ID NO:45), TLGEDDPWL (SEQ ID NO:46), KLGLKPLEV (SEQ ID NO:47), YLWTSAKNT (SEQ ID NO:48), STAPPAHGV (SEQ ID NO:49), GMGSEELRL (SEQ ID NO:50), SLGSPVLGL (SEQ ID NO:51), YLFFYRKSV (SEQ ID NO:52), CQQEETFLL (SEQ ID NO:53), TLAKFSPYL (SEQ ID NO:54), NLTHVLYPV (SEQ ID NO:55), STFKNWPFL (SEQ ID NO:56), SLLQHLIGL (SEQ ID NO:57), FLDQRVFFV (SEQ ID NO:58), FLDQRVFVV (SEQ ID NO:59), FLDQVAFVV (SEQ ID NO:60), GLDREQLYL (SEQ ID NO:61), VMQHLLSPL (SEQ ID NO:62), QQTHGITRL (SEQ ID NO:63), LQPLSGPGL (SEQ ID NO:64), TLDRDSLYV (SEQ ID NO:65), QLYLELSQL (SEQ ID NO:66), KVLEYVIKV (SEQ ID NO:67), KVADLVGFL (SEQ ID NO:68), KTWGQYWQV (SEQ ID NO:70) and VLDGLDVLL (SEQ ID NO:71).

A preferred peptide mixture for use in the methods of the present invention include at least one peptide selected from the group consisting of YMNGTMSQV (SEQ ID NO:5), ITDQVPFSV (SEQ ID NO:7), AAGIGILTV (SEQ ID NO:9), ELAGIGILTV (SEQ ID NO:10), SLLMWITQV (SEQ ID NO:27), FLWGPRALV (SEQ ID NO:30), TLAKFSPYL (PRAME; SEQ ID NO:54) and VLDGLDVLL (SEQ ID NO:71).

In a further preferred method of this embodiment, the method comprises isolating T cells from a leukopheresis sample (otherwise known as a pheresis sample) from a patient for use in said contacting step; and administering to the subject an effective amount of the T lymphocytes collected in said collecting step. Moreover, the method can also comprise restimulating said activated T lymphocytes prior to performing said administering step, said restimulation procedure comprising: contacting the activated T lymphocytes with at least one cytokine, thereby promoting activated T cell proliferation; and incubating the activated T cells with irradiated autologous non-CD8+ cells, adherent nonCD8$^+$ cells or Psoralen/UVA treated artificial antigen presenting cells (aAPCs), thereby generating restimulated activated T lymphocytes. Preferred cytokines include those selected from the group consisting of IL-2, IL-4, IL-7, IL-12, IL-15, IL-17, IL-21, IFN-γ, and TNF-α, and wherein said activated T lymphocytes comprise activated cytotoxic T lymphocytes. Activated T lymphocytes can additionally be subjected to at least one iteration of a restimulation procedure prior to performing said generating step, said restimulation procedure comprising: contacting the activated T lymphocytes with a combination of IL-2 and at least one other cytokine selected from the group consisting of IL-7, IL-15 or IL-21 thereby promoting activated T cell growth, proliferation, or differentiation; and incubating the activated T cells with irradiated autologous non CD8+ cells or adherent nonCD8$^+$ cells or Psoralen/UVA treated aAPCs to generate restimulated T lymphocytes. Preferably the restimulation procedure comprises contacting the activated T lymphocytes with *Drosophila* aAPCs in the presence of IL-2 at a concentration of from 1 to 100 U/ml; IL-7 from 1 to 100 U/ml, IL-15 from 1 to 100 ng/ml and IL-21 from 1 to 100 ng/ml. In one aspect of this method, irradiated autologous adherent nonCD8$^+$ cells comprise irradiated autologous adherent CD14+ cells and in another aspect of this embodiment, irradiated autologous non CD8+ cells comprise irradiated autologous CD4+ T cells.

In yet another aspect of this method, the method further comprises freezing and thawing said artificial antigen presenting cells prior to, subsequent to, or concomitant with said inactivating step and prior to said contacting step. Preferably in all aspects of these methods, the inactivated artificial antigen presenting cells are incapable of proliferation and are essentially free of contamination.

In preferred methods of this invention the artificial antigen presenting cells express a human leukocyte MHC antigen molecule, β-2 microglobulin, and an assisting molecule comprising a co-stimulatory molecule selected from the group consisting of human CD80 (B7-1), LFA-3 (CD58), CD83, CD86 (B7-2) or a member of the TNF family selected from the group consisting of CD70, TNFα, LT, 4-1BBL and OX40L or an adhesion molecule selected from the group consisting of ICAM-1, ICAM-2, ICAM-3 and LFA-3. Still more preferably the artificial antigen presenting cells express the human HLA class I MHC antigen molecule HLA 2.1. Where the class I MHC molecule is HLA-A2.1, the assisting molecules are preferably B7-1 (CD80), LFA-3(CD58), CD70 and ICAM-1(CD54). Also preferably, the artificial antigen presenting cells are psoralen/UVA treated *Drosophila* cells transfected with HLA molecules and costimulation molecules.

As mentioned above, a preferred use of this method relates to a variety of cancers, including malignant melanoma, multiple myeloma, prostate cancer, lymphoma, non-Hodgkin's lymphoma, leukemia, acute lymphoblastic leukemia, acute myeloid leukemia, chronic lymphocytic leukemia, chronic myeloid leukemia, Burkitt's lymphoma, thyroid cancer, uterine cancer, kidney cancer, ovarian cancer, lung cancer, breast cancer, liver cancer, pancreatic cancer, prostate cancer, colon cancer, skin cancer, stomach cancer, cervical cancer, head and neck cancer, glioma, and brain cancer.

In another embodiment of this invention, the invention relates to artificial antigen presenting cells. Preferred psoralen-inactivated artificial antigen presenting cells are those expressing HLA-A2.1, B7-1 (CD80), LFA-3(CD58), CD70 and ICAM-1 (CD54) cell surface protein. One set of preferred peptide mixture to be combined with the artificial antigen presenting cells include YMNGTMSQV (SEQ ID NO:5), ITDQVPFSV (SEQ ID NO:7), AAGIGILTV (SEQ ID NO:9), ELAGIGILTV (SEQ ID NO:10), SLLMWITQV (SEQ ID NO:27), FLWGPRALV (SEQ ID NO:30), TLAKFSPYL (PRAME; SEQ ID NO:54) and VLDGLDVLL (SEQ ID NO:71). When combined with the artificial antigen presenting cells, these peptides associate with the MHC proteins and are said to be "loaded" artificial antigen presenting cells which then present the preferred peptide combination.

Other artificial antigen presenting cells include those expressing the surface proteins HLA-A2.1, B7-1 and ICAM-1. Other artificial antigen presenting cells include cells expressing HLA-A2.1, B&-1, FLA-3, CD70 and ICAM-1; those expressing HLA-A2.1, B&-1, B&-2, FLA-3 and ICAM-1.

BRIEF DESCRIPTION OF THE DRAWINGS

FIG. 3 shows an analysis of the degree of transcription of xenogenic nucleic acid associated with *Drosophila* aAPCs (clone B) that were either untreated, γ-irradiation treated, or UVADEX/UVA treated. Cultures of *Drosophila* xAPCs (clone B) were either untreated, treated with γ-irradiation for 50 minutes (delivering approximately 16,000 rads), or treated with UVADEX (5 µg/ml)/UVA. Each culture of xAPCs was washed and cocultured for 10 weeks with feeder *Drosophila* cell line (clone D) that did not contain xenogenic nucleic acid-encoding HLA A2.1, B7-1, B7-2, or β2m. Reverse transcriptase (RT-PCR) reactions using primers specific for HLA A2.1, B7-1, B7-2, and β2m transcripts were then performed on extracts from the indicator cell lines that were cocultured with each of the untreated, UVADEX (5 µg/ml)/UVA-treated, and γ-irradiated xAPCs. RT-PCR products were then visualized by agarose gel electrophoresis. Lane 1, molecular weight markers; lane 2, RT-PCR products from untreated clone B xAPCs (positive control); lane 3, RT-PCR products from γ-irradiated clone B xAPCs; lanes 4, 5, and 6, RT-PCR products from UVADEX/UVA-treated clone B xAPCs that were UVA radiated for 5, 15, or 30 minutes, respectively, as indicated.

(FIG. 4A, microscopy analysis of lysis of clone D indicator cells incubated with an aliquot of an untreated xAPC viral stock; FIG. 4B, microscopy analysis of lysis of clone D indicator cells incubated with an aliquot of UVADEX/UVA-treated xAPC viral stock; FIG. 4C, analysis of cell survival of clone D indicator cells incubated with the indicated serial dilutions of untreated xAPC viral stock or of UVADEX/UVA xAPC viral stock. Closed circles, clone D cells incubated with untreated viral stock; open circles, clone D cells incubated with UVADEX/UVA treated viral stock.

FIG. 8A shows a comparison of the percentage of CD8$^+$ T cells isolated from C57BL/6 (wild type) mice that were stained with OVA8 peptide (SIINFEKL; SEQ ID NO:69)-bound MHC tetramers after activation with either UVADEX/UVA-treated xAPCs expressing K$^b$, B7-1, and ICAM-1 molecules loaded with the OVA8 peptide or non-treated xAPCs expressing the same molecules (lane 2 vs. lane 1). FIG. 8B shows a comparison of the percentage of CD8$^+$ T cells isolated from MyD88 knock-out (MyD88$^{-/-}$) mice that were stained with OVA8 peptide (SIINFEKL; SEQ ID NO:69)-bound MHC tetramers after activation with either UVADEX/UVA-treated xAPCs or non-treated xAPCs (lane 4 vs. lane 3) as described for FIG. 8A. Lanes 1 and 2, percentage of stained CD8$^+$ T cells isolated form and activated from wild type mice (B6), as described in FIG. 8A (performed as a positive control).

DETAILED DESCRIPTION OF THE INVENTION AND ITS PREFERRED EMBODIMENTS

Figure 1:
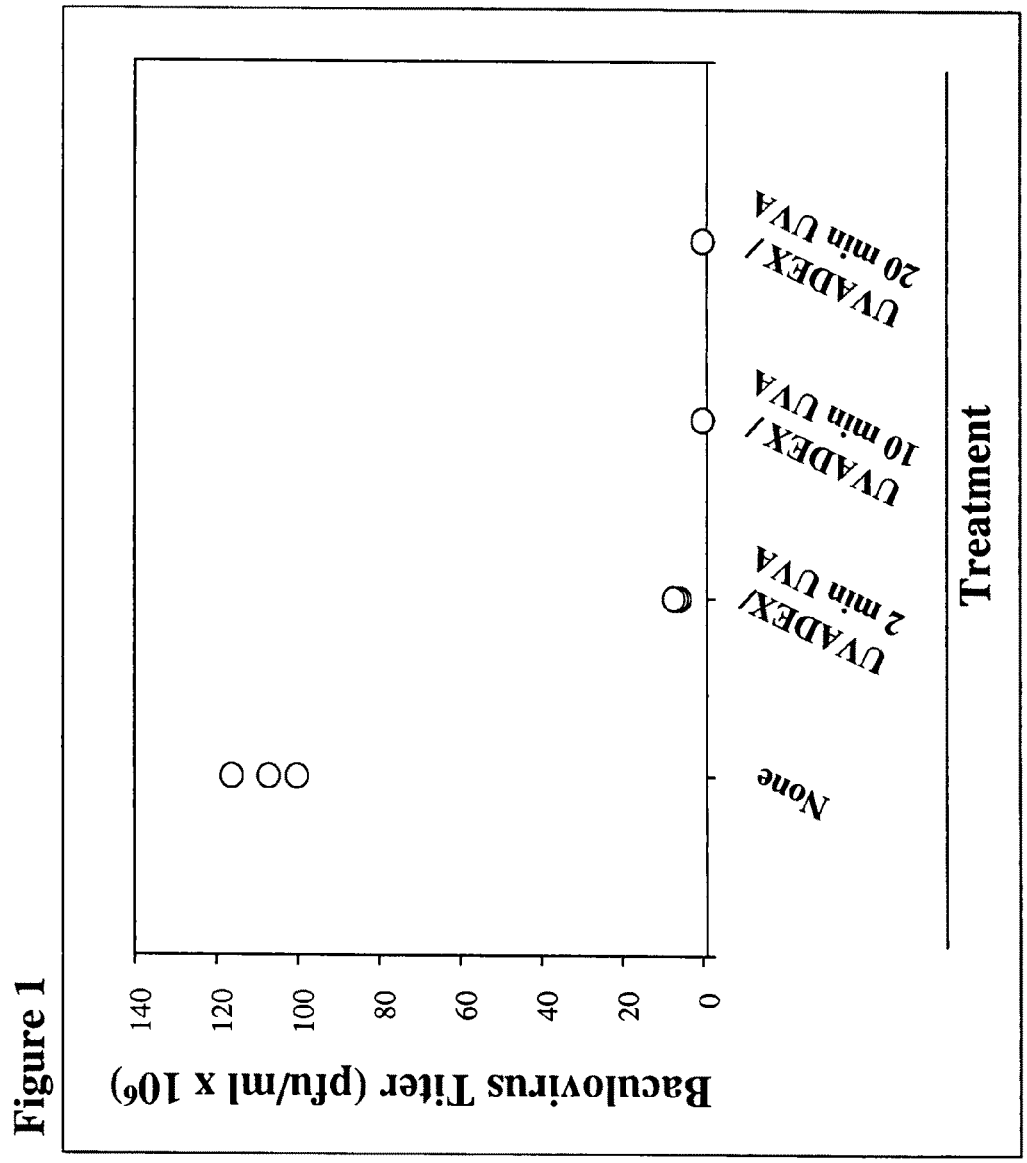
FIG. 1 illustrates the baculovirus titers following UVADEX/UVA treatment of baculovirus-infected Sf9 cells. Sf9 cells were infected with a titrated dose of baculovirus, and the infected cells were treated with 5 µg/ml of UVADEX at 4° C. for 30 minutes, followed by UVA treatment for 0, 2, 10, or 20 minutes, respectively, as indicated. The treated cells were then cultured at 28° C. for 4 days. Cultured supernatant was collected and used to infect fresh, uninfected cultures of Sf9 cells seeded in 96-well plates. Baculovirus present in these Sf9 cultures was detected by a rapid microtiter assay (Invitrogen) using a gp64-specific antibody, and baculovirus titers were calculated.

To illustrate the invention, various exemplary and preferred embodiments are described below. For the sake of brevity, the disclosures of all patents and other publications cited in this specification are incorporated by reference herein. Unless defined otherwise herein or apparent from the context, all technical and scientific terms used herein have the same meaning as used in the art.

The terms "including", "comprising", and "containing" are used herein in their open, non-limiting sense.

In accordance with a general aspect of the present invention, artificial antigen-presenting cells (aAPCs) are exposed to a crosslinking agent, thereby rendering the aAPCs nonviable. Preferably, the aAPCs are also rendered essentially free of microorganism contaminants via the inactivation through crosslinking. Such inactivated aAPCs, when loaded with selected peptide, are still capable of activating naïve T cells to become activated T cells (e.g., either activated cluster of differentiation (CD) CD4$^+$ T cells or activated CD8$^+$ cells T, which are activated helper T cells or CTLs, respectively) specific for selected peptide. The inactivated aAPCs are useful in preparing therapeutic compositions and cell therapy products comprising activated T cells that have been generated by contacting the peptide-loaded inactivated aAPCs. For general guidance regarding the preparation of antigen-presenting systems, including those based on xenogenic species, see, e.g.: U.S. Pat. No. 5,962,320; U.S. Patent Application Publication Nos. 2003/0072796, 2003/0077248, 2004/0071671, 2005/0152916, and 2006/0134125; International Publication Nos. WO 00/63690, WO 02/065992, and WO 02/092773; Oelke et al., TRENDS in Molecular Medicine, Vol. 11(9), pp. 412-420 (2005); Sun et al., Immunity, vol. 4, pp. 555-564 (1996); and Kim et al., Nature Biotechnology, Vol. 22(4), pp. 403-410 (2004).

The specific naïve T cell lineage that is activated by the inactivated aAPCs depends on the nature of MHC molecules that are expressed on the surface of the aAPCs. Accordingly, aAPCs expressing only MHC Class I molecules may present selected peptide to and activate naïve CD8$^+$ T cells, and aAPCs expressing MHC Class II molecules may present selected peptide to and activate naïve CD4$^+$ T cells. Similarly, aAPCs expressing both MHC Class I and MHC Class II molecules may present selected peptide to and activate both naïve CD8$^+$ T cells and CD4$^+$ T cells.

To produce a cell therapy product, autologous naïve T cells obtained from a pheresis sample withdrawn from a subject are contacted with inactivated aAPCs that have been loaded with selected peptide, such as a peptide comprising at least eight contiguous amino acids of the amino acid sequence of a human AML protein. As a result, the contacted naïve T cells become activated, in that they are primed to target cells expressing at least one epitope that corresponds to selected peptide with which the naïve T cells were activated. When encountered by the activated T cells, such targeted cells may be killed by the activated T cells by virtue the ability of the activated T cells to exhibit specific target cell cytotoxicity (i.e., specific cell killing).

The pheresis sample may be collected from the subject by any of a number of suitable lymphocytapheresis, lymphapheresis, and leukaphoresis procedures now known or that become available in the art, which provide for the collection of peripheral blood leukocytes (PBLs) from collected peripheral blood, and from which leukocytes may separated from other plasma components of the sample. Exemplary procedures are illustrated in, e.g., U.S. Patent Application Publication Numbers US 2004/0173778 and US 200/40147021, and U.S. Pat. Nos. 4,690,915, 5,126,132, 6,255,073, 5,846,827, 6,251,385, 6,225,044, 6,210,963, 6,194,207, 5,443,983, 6,040,177, 5,766,920, 6,210,662, 6,204,058, and 6,227,368. From the pheresis sample, naïve T cells, which may be naïve CD4$^+$ T cells, naïve CD8$^+$ T cells, or naïve CD4$^+$ T cells and naïve CD8$^+$ T cells, are substantially separated from other PBLs, e.g., non-T cells. Preferably, naïve CD8$^+$ T cells are separated and then employed to produce a therapeutic composition or a cell therapy product containing autologous cytotoxic T cells (CTLs), which product is reinfused or transfused back into the subject from whom the pheresis sample used to derive the cell therapy product was obtained. Reinfusion procedures that may be employed include those procedures disclosed in, for example, U.S. Pat. Nos. 4,844,893 and 4,690,915.

A subject from whom a pheresis product comprising naïve T cells may be obtained is preferably a mammal in need of treatment, such as a dog, a cat, a horse, a rat, rabbit, mouse, a non-human primate, or a human. More preferably, the subject is a human patient in need of treatment for a disease, disorder, or medical condition associated with aberrant immune system function. Alternatively, in appropriate circumstances immune cells, such as naïve T cells, that are not derived from a subject to be treated, but which are derived from another compatible source such as an immune cell donor, or even an immortalized or transformed immune cell line, may be employed to prepare cell therapy products in accordance with the invention.

Methods for selection of PBLs include procedures employing Ficoll gradients, technique employing immunopurification (e.g., monoclonal antibodies directed against cell surface markers, such as CD molecules, and beads, such as Sepharose-, Protein A-, and Protein G-conjugated beads to which the antibodies may be adsorbed, and magnetic beads to which antibodies may be adsorbed), flow cytometry, and fluorescence-activated cell sorter (FACS) analysis.

Selected naïve T cells are preferably substantially separated from non-selected pheresis sample components. More preferably, selected naïve T cells are substantially purified by magnetic bead purification systems such as those available in the art, e.g., Miltenyi beads (Myltenyi Biotec) and Dynabead systems (Dynal Biotech) combined with cell sorting procedures, such as FACS-based methods, or other appropriate cell sorting devices and methodologies. The thus-selected naïve T cells are then admixed and incubated with inactivated and selected-peptide loaded aAPCs for a time sufficient to activate and enrich for a desired, population of activated T cells, such as activated helper T cells, and preferably, CTLs or CD8$^+$ memory T cells. Such activated T cells preferably are activated in a peptide-specific manner.

The ratio of substantially separated naïve T cells to aAPCs may be optimized for the particular individual, e.g., in light of individual characteristics such as the amenability of the individual's lymphocytes to culturing conditions and the nature and severity of the disease or other condition being treated. An exemplary separated naive T cell to inactivated aAPC ratio is from about 30:1 to 300:1. For example, $3 \times 10^7$ human PBL and $1 \times 10^6$ aAPCs may be admixed and maintained in medium comprising RPMI 1640 culture medium.

Accordingly, naïve T cells comprise CD4$^+$ or CD8$^+$ cells that have not been primed with selected peptide-loaded aAPCs. Naïve T cells may be identified experimentally based on one or more appropriate characteristics routinely selected, such as those associated with cell growth and proliferation status, cell phenotype, and cellular activity. With respect to cell growth and proliferation status, naïve T cells preferably comprise a population of resting T cells—that is, they tend to reside in the $G_0$ portion of the cell cycle. Activated T cells are often in $G_1$ or S phase of the cell cycle. Memory T cells comprise T cells that were once naïve but have been activated and have subsequently re-entered a resting state, or comprise naïve T cells that acquired a memory phenotype as a result of homeostatic expansion (see Opferman et al., *Science*, Vol. 283, pp. 1745-1748 (1999); Wherry et al., *Nat. Immunol.*, Vol. 4, pp. 225-234 (2003); Kaech et al., *Cell*, Vol. 111, pp. 837-851 (2002); Kieper et al., *Proc. Natl. Acad. Sci. USA*, Vol. 96, pp. 13306-13311 (1999); Goldrath et al., *J. Exp. Med.*, Vol. 192, pp. 557-564 (2000); Murali-Krishna et al., *J. Immunol.*, Vol. 165, pp. 1733-1737 (2000)). Such memory T cells may be re-activated upon, for example, re-exposure to priming antigen, assistance from CD4+ T helper cells, and/or exposure to appropriate cytokines. Thus, compared to memory T cells and activated T, naïve T cells are relatively non-proliferative in vivo, unless depletion of the naïve T cell pool (such as occurs during a robust activation of T cells in response to antigen) necessitates a period of relatively slow homeostatic proliferation in order to replenish naïve T cell numbers (see, e.g., Kieper et al., *J. Immunol.*, Vol. 174, pp. 3157-3163 (2005), and Baccala et al., *J. Immunol.*, Vol. 174, pp. 4606-4612 (2005)). With respect to phenotype, naïve T cells may be distinguished from non-naïve T cells (e.g., CD4$^+$ helper T cells, memory T cells, and effector T cells (e.g., CTLs)) by the existence and relative level of expression of a naïve T cell-associated CD molecule profile, which may include CD11a$^{low}$/LFA-1$^{low}$ (or$^{dim}$), CD25$^{low}$, CD27$^+$ (or$^{hi}$), CD44$^{low}$ or CD44$^{int}$, CD45RA$^+$ (or$^{pos}$), CD45RO$^-$ (or$^{neg}$), CD95$^{low}$ (or$^{dim}$), CD57$^-$ (or$^{neg}$), and CD62L$^{hi}$ (or$^{bright}$) as compared to the level of expression observed for non-naïve T cells. Naïve T cells may also be distinguished by a relatively high level of expression of the chemokine receptor, CCR7 (CCR7$^{hi}$) as compared to the level of expression observed for non-naïve T cells (see, e.g., McFarland et al., *PNAS*, Vol. 97(8), pp. 4215-4220 (2000); Ishimaru et al., *Nature Immunol.*, Vol. 7(7), pp. 763-772 (2006); and Kern et al., *Eur. J. Immunol.*, Vol. 29, pp. 2908-2915 (1999)). In contrast, memory cells, for example, may be characterized by a CD27$^{low}$, CD44$^{hi}$, CD45RA$^-$, CD45RO$^+$, CD57$^+$ (or hi), CD62L$^{low}$, and/or CCR7$^{low}$ phenotype (see, e.g., Kern et al., *Eur. J. Immunol.*, Vol. 29, pp. 2908-2915 (1999), and Baccala et al., *J. Immunol.*, Vol. 174:4606-4612 (2005)). With respect to cellular activity, naïve T cells may be characterized by an inability to efficiently produce or secrete interferon alpha, interferon gamma, interleukin (IL)1, IL-2, IL-3, IL-4, IL-5, IL-6, IL-7, IL-8, IL-9, IL-10, IL-12, tumor necrosis factor alpha (TNF-α), and/or granulocyte macrophage-colony stimulating factor GM-CSF (see, e.g., Cerwenka et al., *J. Immunol.*, Vol., 161, pp. 97-105 (1998); Walzer et al., *Cell. Immunol.*, Vol. 206, pp. 16-25 (2000); Tizard, I., IMMUNOLOGY: AN INTRODUCTION, 3$^{rd}$ Edition, pp. 129-143 (1992); U.S. Patent Application Publication No. US 2002/0119121; and International Publication No. WO 2002/022648). Naïve T cells also do not exhibit substantive cytotoxicity or specific cell killing activity towards presumptive target cells.

Naïve T cells, which may comprise naïve CD8$^+$ T cells, naïve CD4$^+$ T cells, or combinations of CD8$^+$ T cells and CD4$^+$ T cells that are primed and stimulated, and therefore activated, as described above, may optionally be restimulated and/or expanded to produce therapeutic compositions and cell therapy products comprising activated T cells of a desired phenotype and number. Exemplary restimulation procedures include adding one or more selected cytokines that promote activated T cell growth, proliferation, and/or differentiation and incubating activated T cells with selected peptide-loaded nonCD8$^+$ cells, such as CD14$^+$ cells. The selection of appropriate cytokines will depend on the desired phenotype of the activated T cells that will ultimately comprise the therapeutic composition or cell therapy product. Thus, naïve CD4+ T cells may be activated and optionally restimulated and/or expanded to become CD4$^+$ T helper (Th) 1 cells or CD4$^+$ Th2 cells, and naïve CD8+ T cells may be activated and optionally restimulated and/or expanded to become CTLs possessing a Tc1-like phenotype, CTLs possessing a Tc2-like phenotype, memory T cells, or a combination of such, as desired by the artisan considering guidance in the art (see, e.g., Cerwenka et al., *J. Immunol.*, Vol. 163(10), pp. 5535-5543 (1999); Mosmann et al., *Immunol. Today*, Vol. 17(3), pp. 138-146 (1996); Carter et al., *Curr. Opin. Immunol.*, Vol. 8(3), pp. 336-342 (1996); Croft et al., *J. Exp. Med.*, Vol. 180, pp. 1715-1728 (1994); Fujihashi et al., *Proc. Natl. Acad. Sci. USA*, Vol. 93, pp. 3613-3618 (1996); U.S. Pat. No. 6,355,479 and International Publication No. WO 97/46256. Preferred cytokines include IL-1, IL-2, IL-7, IL-4, IL-5, IL-6, IL-12, IFN-γ, and TNF-α. An exemplary T cell expansion procedure includes incubating activated T cells with irradiated nonCD8$^+$ cells in the presence of selected cytokines and an anti-CD3 antibody preparation, such as OKT®3, to promote non-specific activated T cell expansion. Selection of the number, sequence, and combination of such restimulation and expansion protocols to be employed are within the purview of the artisan and may be facilitated by guidance in the art. See, e.g., Cerwenka et al., *J. Immunol.*, Vol. 161, pp. 97-105 (1998); Livingston et al., *Immunol. Invest.*, Vol. 24(4), pp. 619-629 (1995); Sad et al., *Immunity*, Vol. 2, pp. 271-279 (1995); U.S. Patent Application Publication No. US 2003/0170212; and International Publication No. WO 02/092773.

In preferred embodiments, T cells that have been stimulated are subsequently subjected to at least one iteration of a restimulation procedure, comprising contacting the stimulated T cells with amounts of IL-2 and IL-7 sufficient to promote the growth, proliferation, and/or differentiation of the activate T cells, and then incubating the so-contacted T cells with irradiated, autologous, adherent nonCD8$^+$ cells (e.g., CD14$^+$ cells) and additional sufficient amounts of IL-2 and IL-7. In embodiments in which the restimulation procedure is performed more than once, the activated T cells are contacted with additional amounts of IL-2 and IL-7 between each iteration of the restimulation procedure. In other preferred embodiments, the activated T cells are subjected to at least one expansion procedure subsequent to the at least one iteration of a restimulation procedure, wherein the expansion procedure comprises incubating activated T cells with irradiated nonCD8$^+$ cells in the presence of an amount of IL-2 sufficient to promote the growth, proliferation, and/or differentiation of the so-contacted T cells, and an anti-CD3 antibody preparation, preferably OKT®3.

In preferred embodiments, the naïve T-cells comprise CD8$^+$ T cells, which when activated and optionally re-stimulated and/or expanded, may exhibit, for example, cytotoxic activity toward cells to which they are targeted or produce immunostimlatory or cytotoxicity-associated cytokines. Preferably, they exhibit a combination of these features. Naive CD8$^+$ T cells that have been primed and activated may be subjected to restimulation and/or expansion protocols as described above, which drive differentiation and/or polarization of so-activated CD8+ T cells toward specific CTL cell lineage phenotypes, such as CD8$^+$ Tc1 and CD8$^+$ Tc2 phenotypes. The peptide-loaded aAPC-activated CD8$^+$ T cells may also be subjected to several rounds of restimulation, in vivo or in vitro, with selected peptide alone or in conjunction with certain cytokines, such as IL-2, IL-7, and IL-12, and interferon gamma or with antibodies, such as those directed against the T cell receptor (TCR) and costimulatory molecules on the surface of the activated T cells. In preferred embodiments, activated CD8$^+$ T cells are further restimulated in this way, which maintain immunogenicity and cytotoxicity for target cells for at least about four or five generations, yielding memory CD8$^+$ T cells. Methods for memory CD8$^+$ T cell identification, characterization, immunogenicity maintenance, and expansion may be found in, for example, Cerwenka et al., *J. Immunol.*, Vol., 161, pp. 97-105 (1998); Cerwenka et al., *J. Immunol.*, Vol. 163, pp. 5535-5543 (1999); Patent Application Publication No. 2002/0119121; and International Publication No. WO 2002/022648.

The aAPCs that are employed in the cell therapy product preparation methods may comprise inactivated xAPCs, which are modified host cells from a non-human species that are capable of expressing exogenous molecules on their surface, and xAPC culture medium. The aAPCs also comprise an exogenous MHC molecule selected from MHC Class I molecules and MHC Class II molecules. The aAPC systems optionally further comprise at least one exogenous assisting molecule that assists in the activation of naïve T cells. Preferably, the exogenous molecules are encoded by xenogenic nucleic acid that has been introduced into host cells.

Preferably, the aAPCs comprise at least one co-stimulatory molecule in addition to the MHC Class I or Class II molecule. More preferably, the aAPCs comprise at least one co-stimulatory molecule and at least one adhesion molecule in addition to the MHC Class I or Class II molecule (see Kim et al., 2004, *Nature*, Vol. 22(4), pp. 403-410; Cai et al., 1996, *Proc. Natl. Acad. Sci. USA*, Vol. 93, pp. 14736-14741; Jackson et al., 1992, *Proc. Nat. Acad. Sci. USA*, Vol. 89, pp. 12117-12121; Schoenberger et al., 1998, *Cancer Res.*, Vol. 58, pp. 3094-3100; and Latouche et al., 2000, *Nat. Biotechnol.*, Vol. 18, pp. 405-409). Techniques, methods, and reagents useful for selection, cloning, preparation, and expression of exemplary assisting molecules, including co-stimulatory molecules and adhesion molecules, are exemplified in, e.g., U.S. Pat. Nos. 6,225,042, 6,355,479, and 6,362,001. Preferred HLA class I MHC antigen molecules include, but not limited to, HLA 2.1 (HLA-A*0201), as well as HLA-A*0101, HLA-A*0301, HLA-A*1101, HLA-A*2402, HLA-A*3303, HLA-C*0701, HLA-C*0702, HLA-C*0401, HLA-B*0702, HLA-B*4402, HLA-B*3501.

Preferred MHC Class I molecules include a heavy chain (e.g., an alpha chain) and a β2-microglobin. Such an MHC Class I molecule may be either a full-length molecule or an extracellular portion of a full-length molecule, such extracellular portion lacking complete transmembrane or cytoplasmic domains, or lacking both complete transmembrane and cytoplasmic domains. The MHC Class I molecule is preferably capable of binding a selected peptide. Exemplary MHC Class I molecules that may be employed in the present invention include, for example, molecules that are encoded by human leukocyte antigen (HLA)-A, HLA-B, HLA-C, HLA-E, HLA-F, or HLA-G loci. Preferably, the MHC Class I molecule is selected from molecules encoded by HLA-A, HLA-B, and HLA-C loci. Techniques, methods, and reagents useful for selection, cloning, preparation, and expression of β2-microglobin molecules, MHC Class I molecules such as HLA molecules, and portions thereof, are exemplified in U.S. Pat. Nos. 6,225,042, 6,355,479, and 6,362,001.

Preferred MHC Class II molecules include an alpha (α) chain and a beta (β) chain which associate together to form an MHC class II heterodimer. Such an MHC Class II heterodimer may be either a full-length molecule or an extracellular portion of a full-length α chain, an extracellular portion of a full-length β chain, or extracellular portions of both α and β chains, such extracellular portion or portions lacking complete transmembrane or cytoplasmic domains. Exemplary MHC Class II molecules that may be employed in the present invention include molecules that are encoded by HLA-DP, HLA-DQ HLA-DR, HLA-DO, HLA-DN, or HLA-DZ loci. Techniques, methods, and reagents useful for selection, cloning, preparation, and expression of MHC Class II α chains, β chains, and αβ heterodimers, and extracellular portions thereof, are exemplified in U.S. Pat. Nos. 5,583,031, and 6,355,479.

The assisting molecule facilitates the activation of naïve T-cells when such naïve T cells are presented with an MHC Class I or Class II molecule to which a selected peptide, which is an antigen or an immunogen, or both an antigen and an immunogen, is bound. The assisting molecule may be assisting molecules such as: (i) co-stimulatory molecules, which are proteins expressed by antigen presenting cells such as B7.1 (previously known as B7 and also known as CD80) and B7.2 (also known as CD86), and CD70, which, among other things, bind to CD28 and/or CTLA-4 molecules on the surface of T cells, thereby effecting, for example, cytokine, such as interleukin (IL)-2, secretion, T-cell expansion, Th1 differentiation, and short-term T-cell survival (see Kim et al., 2004, *Nature*, Vol. 22(4), pp. 403-410); and (ii) adhesion molecules, for example, carbohydrate-binding glycoproteins such as selecting, transmembrane binding glycoproteins such as integrins, calcium-dependent proteins such as cadherins, and single-pass transmembrane immunoglobulin (Ig) superfamily proteins, such as intercellular adhesion molecules (ICAMs), that promote, for example, cell-to-cell or cell-to-matrix contact. Preferred adhesion molecules include ICAMs, such as ICAM-1, ICAM-2, ICAM-3 and LFA-3. Any suitable number and combination of assisting molecules may be employed.

The host cells may be modified to become aAPC lines for use in activating naïve T cells. Any type of cells capable of continuous growth in culture that can be manipulated to express the exogenous molecules may selected as a source of host cells (see, e.g., *Current Protocols in Molecular Biology*, John Wiley & Sons, N.Y. (1991), for summaries and procedures for culturing and using a variety of cell lines). Accordingly, the host cells may originate from any of a variety of species, including prokaryotic species, such as bacterial species, or eukaryotic species, such as, yeasts, insects, plants, mycoplasmas, and mammals.

In preferred embodiments the host cells include primary cells that are harvested and isolated from an organism, preferably an animal, and are either employed directly in the preparation of the antigen presentation system or are so employed after the primary cells are cultured, or passed, through a limited number of generations, e.g., from one to fifty. Alternatively, such primary cell lines may be cultured under conditions that allow for the generation of an immortalized cell line that is descendent from the ancestral primary cell line, which may be routinely selected. Such immortalization may entail culturing primary cells through a sufficient number of generations such that a crisis period is reached, during which most primary cells in the culture die while a relatively small number of rapidly dividing variants persist. A culture that is founded by such a persistent variant may theoretically be passed through any number of generations, provided that the cells are diluted at appropriate times and by an appropriate dilution factor, and that appropriate nutrients and media are replenished, to allow for sustained propagation. Transformed cell lines also may serve as a source of eukaryotic host cells that may be employed in the preparation of the antigen presentation system. Such transformed cell lines may be derived from tumor cells taken from an animal harboring such a tumor. Various types of immortalized or transformed cell lines may be acquired from any of a number of cell line repositories, such as the American Type Culture Collection (ATCC), or may be prepared by the artisan using routine techniques now known or that become available in the art.

Exemplary parameters that may be manipulated to obtain a desired set of host cell and aAPC growth and culture conditions include temperature, degree of aeration, percentage oxygen saturation, percentage carbon dioxide saturation, nutrient composition and concentration, and static growth versus agitated (i.e., shaking) growth. Illustrative methods for the preparation, growth, and culture of selected host cells, such as Schneider 2 cells, are provided in U.S. Pat. Nos. 6,225,042, 6,355,479, and 6,362,001; Sambrook et al., MOLECULAR CLONING: A LABORATORY MANUAL, Second Edition, Cold Spring Harbor Laboratory, Cold Spring Harbor, N.Y., (1989); Ausubel et al. (eds.), CURRENT PROTOCOLS IN MOLECULAR BIOLOGY, Greene Publishing Association and John Wiley Interscience, New York, 1992; and Frank, "Perspectives on Baculovirus Expression Systems", November 1998, OMRF Research Technology Forum.

Host cells selected for modification to become aAPCs are preferably deficient in intracellular antigen-processing, intracellular peptide trafficking, and/or intracellular MHC Class I or Class II molecule-peptide loading, or are poikilothermic (i.e., less sensitive to temperature challenge than mammalian cell lines), or possess both deficient and poikilothermic properties (see, e.g., DeSilva et al., 1999, *J. Immunol.*, Vol. 163(8), pp. 4413-4420; Schumacher et al., 1990, *Cell*, Vol. 62(3), pp. 563-567; Ljunggren et al., 1990, *Nature*, Vol. 346(6283), pp. 476-480). Preferably, selected host cells also lack the ability to express at least one endogenous counterpart (e.g., endogenous MHC Class I or Class II molecule and/or endogenous assisting molecules as described above) to the exogenous MHC Class I or Class II molecule and assisting molecule components that are introduced into such host cells. Furthermore, aAPCs preferably retain those deficiency and poikilothermic properties that were possessed by the selected host cells prior to their modification to generate the aAPCs. In preferred embodiments, selected host cells either constitute or are derived from a transporter associated with antigen processing (TAP)-deficient cell line, such as an insect cell line.

Preferred selected host cells are poikilothermic insect cells. Exemplary insect cell lines from which selected host cells may be selected include, for example, those derived from moth (ATCC CCL 80), army worm (ATCC CRL 1711), mosquito larvae (ATCC lines CCL 125, CCL 126, CRL 1660, CRL 1591, CRL 6585, CRL 6586) and silkworm (ATCC CRL 8851). In especially preferred embodiments, the cell line is a *Drosophila* cell line, such as a Schneider 2 cell line (see, e.g. Schneider, 1972, *J. Embryol. Exp. Morph.*, Vol 27, pp. 353-365), a cell line derived from *Spodoptera*, such as SF-9 cells or SF-21 cells, or a cell line derived from *Trichoplusia*, such as Tn5 cells, H5 cells, and High-Five™ (Invitrogen) cells.

The selected host cells are modified in order to express exogenous MHC Class I or MHC Class II molecules, and preferably more than one of the above-described exogenous assisting molecules, by methods which comprise the introduction of xenogenic nucleic acid into the host cells, thereby generating the aAPCs. Thus, the aAPCs, once generated by modification of selected host cells, may express either exogenous MHC Class I or exogenous MHC Class II molecules selected from the HLA molecules described above, in addition to from one to fifteen or more exogenous assisting molecules selected from co-stimulatory and adhesion molecules, as suitable for the desired cell therapy. In certain preferred embodiments, host cells are modified to express exogenous HLA-A2 molecules in addition to exogenous B7.1 (CD80), B7.2 (CD86), ICAM-1 (CD54), and LFA-3 (CD58). In other preferred embodiments, host cells are modified to express exogenous HLA-A2 molecules in addition to exogenous B7.1 (CD80), ICAM-1 (CD54), LFA-3 (CD58), and CD70.

The xenogenic nucleic acid may be a DNA sequence or RNA sequence, or may comprise both a DNA sequence and a RNA sequence. Preferably, the xenogenic nucleic acid is a DNA sequence.

The xenogenic nucleic acid is preferably incorporated into one or more vectors that are suitable for introduction into the selected host cells, preferably by transfection. A vector may be a suitable nucleotide sequence comprising at least one xenogenic nucleic acid sequence that encodes at least a portion of an exogenous molecule, operatively linked to vector sequences that facilitate expression of the so-linked xenogenic nucleic acid sequence. The xenogenic nucleic acid sequence to be operatively linked to vector sequences encodes at least a portion of a mammalian MHC molecule. Preferably, an entire protein-coding sequence of the MHC molecule is inserted into the vector and expressed. In embodiments in which a portion of an MHC molecule is utilized, such as an extracellular portion, such a portion may be prepared by, for example, insertion of a sequence that directs termination of translation (i.e., a stop codon) at the end of the sequence encoding the extracellular portion. In such embodiments, the extracellular portion is preferably altered so that it may be at least partially retained within the membrane of the modified cells once such cells express the extracellular portion. In preferred embodiments, the MHC molecule that is used is a full-length MHC Class I molecule.

In preferred embodiments in which a vector encoding MHC Class I molecule is employed, a second vector encoding at least a portion of a mammalian β2 microglobulin molecule operatively linked to the second vector may be used for expression of the β2 microglobulin molecule, or a portion thereof. Alternatively, single vector including nucleotide sequences encoding a Class I MHC molecule and a β-2 microglobulin may be used.

In further preferred embodiments, at least one additional vector, in addition to an MHC molecule-encoding vector and a β2-microglobulin-encoding vector, is employed, which encodes at least a portion of an assisting molecule operably linked to the vector. In still further preferred embodiments, a plurality of additional vectors are employed, each vector encoding an assisting molecule selected from co-stimulatory molecules, such as B7-1 (previously known as B7 and also known as CD80) and B7-2 (also known as CD86), and adhesion molecules, which include ICAM molecules, such as ICAM-1, ICAM-2, ICAM-3, and LFA-3. Any suitable combination of co-stimulatory and adhesion molecules may be employed in the generation of aAPCs.

Additionally, in certain preferred embodiments, β2-microglobulin molecules are obtained from β2-microglobulin host cells, which are distinct from the host cells that are modified to become aAPCs. In such embodiments, a vector encoding the β2-microglobulin molecule is introduced into the β2-microglobulin host cells and expressed, and a sample of the expressed β2-microglobulin molecules is collected. Alternatively, a sample of β2-microglobulin molecules may be derived from an organism that expresses endogenous β2-microglobulin. aAPCs expressing exogenous MHC Class I molecules may then be incubated with the sample of β2-microglobulin molecules.

To obtain a desired level of expression of nucleic acid sequence, the nucleic acid sequence is inserted into a vector containing a promoter to direct transcription, a transcription/translation terminator, and, if for a nucleic acid sequence encoding a protein, a ribosome binding site for translational initiation. Exemplary bacterial promoters are described in Sambrook et al., supra; and Ausubel et al., supra. Illustrative bacterial expression systems for expressing constituent proteins include *E. coli, Bacillus* sp., and *Salmonella* (Palva et al., 1983, *Gene* 22:229-235; Mosbach et al., 1983, *Nature* 302:543-545). Kits for such expression systems are commercially available. Suitable eukaryotic expression systems for mammalian cells, yeast, and insect cells are also known in the art or available.

In addition to a promoter, each vector preferably contains a transcription unit or expression cassette that contains all the additional elements required for the expression of xenogenic nucleic acid in host cells. An exemplary vector contains a promoter operably linked to xenogenic nucleic acid, and signals required for efficient polyadenylation of the transcript, ribosome binding sites, and translation termination. Xenogenic nucleic acid may be linked to a cleavable signal peptide sequence to promote secretion of the encoded protein by the transfected cell. Exemplary such signal peptides include the signal peptides from tissue plasminogen activator, insulin, and neuron growth factor, and juvenile hormone esterase of *Heliothis virescens*. Additional or alternative elements, e.g., enhancer elements, endogenous promoter elements, introns with or without functional splice donor and acceptor sites, translation termination elements, or polyadenylation signals, all or some of which may be endogenous elements of a selected xenogenic nucleic acid, may be included in the cassette or in the vector.

Exemplary vectors suitable for expression of xenogenic nucleic acid in bacterial, mammalian and/or insect host cells include: pRmHa vectors, including pRmHa-1, pRmHa-2, and pRmHa-3 (see, e.g., International Publication No. WO 96/27392 and U.S. Pat. Nos. 6,225,042 and 6,355,479); pBR322-based vectors, pSKF, pET23D, pCDM8 (Seed, 1987, *Nature*, Vol. 329, pg. 840) and pMT2PC (Kaufman et al., 1987, *EMBO J*, Vol. 6, pp. 187-195), pMAMneo (Clontech), pcDNA3 (Invitrogen), pMC1neo (Stratagene), pCM-VSPORT, pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), pMSCV, and 1ZD35 (ATCC 37565), pUC8, pUC9, pUC18, pBR322, and pBR329 (BioRad Laboratories), pPL and pKK223 (Pharmacia), and pBS (Stratagene) and M13 mp19 (Stratagene). Preferred vectors for use in preparing the aAPCs include vectors containing regulatory elements from eukaryotic viruses, such as SV40 vectors, papilloma virus vectors, vaccinia virus vectors, baculovirus, and vectors derived from Epstein-Barr virus. Such vectors allow expression of inserted xenogenic nucleic acid under the direction of the CMV promoter, SV40 early promoter, SV40 late promoter, metallothionein promoter, murine mammary tumor virus promoter, Rous sarcoma virus promoter, polyhedrin promoter, or another promoter effective for expression in eukaryotic cells.

A variety of recombinant baculovirus expression vectors have been developed for infection into host cells derived form several insect species, such as *Aedes aegypti, Bombyx mori, Drosophila melanogaster, Spodoptera frugiperda*, and *Trichoplusia ni* (see, e.g., International Publication No. WO 89/046699; Carbonell et al., 1985, *J. Virol*. Vol. 56, pg. 153; Wright, 1986, *Nature*, Vol. 321, pg. 718; Smith et al., 1983, *Mol. Cell. Biol*., Vol. 3, pg. 2156; and Fraser, et al., 1989, *Cell. Dev. Biol*., Vol. 25, pg. 225). Preferred virus-derived vectors include baculovirus-based vectors, such as BaculoGold™ (BD Biosciences), BacPAK6 (BD Biosciences), ProEasy™ (BD Biosciences), and pDSVE.

To employ a vector comprising xenogenic nucleic acid that encodes MHC Class I molecules, MHC Class II molecules, co-stimulatory molecules, or assisting molecules, or a combination of these, a variety of host-expression vector systems available in the art may be utilized. Such host-expression systems represent vehicles by which the coding sequences of interest may be produced and subsequently purified, but also represent cells which may, when transformed or transfected with the appropriate nucleotide coding sequences, express the molecules. These include, for example, microorganisms such as bacteria (e.g., *E. coli, B. subtilis*) transformed with recombinant bacteriophage DNA, plasmid DNA or cosmid DNA expression vectors containing MHC coding sequences; yeast (e.g., *Saccharomyces, Pichia*) transformed with recombinant yeast expression vectors containing MHC coding sequences; insect cell systems infected with recombinant bacterial expression vectors containing MHC coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing MHC coding sequences; or mammalian cell systems (e.g., COS, CHO, BHK, HEK 293, 3T3 cells) harboring recombinant expression vectors containing promoters derived from the genome of mammalian cells (e.g., metallothionein promoter) or from mammalian viruses (e.g., the adenovirus late promoter; the vaccinia virus 7.5K promoter, Semliki forest virus promoter). Furthermore, nucleic acid sequence encoding polypeptide tags may also be inserted into selected vectors such that the exogenous polypeptides expressed therefrom contain the encoded polypeptide tag, allowing for convenient methods of isolation and/or detection. Exemplary tags include c-myc tag, hemoglutinin (HA)-tag, 6x-His tag, maltose binding protein tag, VSV-G tag, FLAG tag, and V5 tag.

Preferred expression systems for expression of exogenous proteins are expression systems comprising use pRmHa vectors, such as pRmHa-1, pRmHa-2, and pRmHa-3 (Bunch et al., 1988, *Nucl. Acids Res*., Vol. 16, pp. 1043-1061), which are introduced into host cells, such as insect cells, preferably *Drosophila* cells.

In particularly preferred embodiments, the expression vectors are inducible vectors. aAPCs that comprise such inducible expression vectors may first require stimulation by an inducing agent, such as $CuSO_4$, for a predetermined period of time to effect appreciable exogenous protein expression. Preferably, MHC molecule expression is driven by an inducible expression vector encoding such MHC molecule. After a suitable induction period, e.g., about 12-48 hours, selected peptide (which may be prepared as discussed below) may be added at a predetermined concentration (e.g., about 100 μg/ml). After a further incubation period, e.g., for about 12 hours at 27° C., the culture is ready for use in the activation of $CD8^+$ cells. While this additional incubation period may be shortened or perhaps omitted, the culture is preferably allowed to incubate for a time prior to addition of naive T cells to enhance its resilience to temperature challenge. For example, cultures to which selected peptide has been added are capable of expressing significant amounts of selected peptide-loaded Class I MHC molecules even when incubated for extended periods of time at 37° C.

Exemplary procedures for introducing foreign nucleotide sequences into host cells may be used to introduce the xenogenic nucleic acid into selected host cells include the use of reagents such as Superfect (Qiagen), liposomes, calcium phosphate transfection, polybrene, protoplast fusion, electroporation, microinjection, plasmid vectors, viral vectors, biolistic particle acceleration (e.g., the Gene Gun), or any other appropriate method for introducing cloned genomic DNA, cDNA, synthetic DNA, RNA or other foreign genetic material into a host cell (see, e.g., Sambrook et al., MOLECULAR CLONING: A LABORATORY MANUAL, Second Edition, Cold Spring Harbor Laboratory, Cold Spring Harbor, N.Y., (1989)). For stable transfection of host cells, it will be apparent that, depending on the expression vector and transfection technique used, only a small fraction of cells may integrate the foreign DNA into their genome. To identify and select these integrants, a gene that encodes a selectable marker (e.g., for resistance to antibiotics) may be introduced into the host cells along with the gene of interest. Preferred selectable markers include those conferring resistance to drugs, such as geneticin (G418), puromycin, hygromycin, and methotrexate. Cells stably transfected with the introduced nucleic acid may be identified by drug selection (e.g., cells that have incorporated the selectable marker gene will survive, while the other cells die).

At least a portion of xenogenic nucleic acid associated with the aAPCs, and in preferred embodiments, xenogenic nucleic acid and nucleic acid endogenous to the host cells from which the aAPCs derive, are inactivated by crosslinking subsequent to, or concomitant with, the expression of such exogenous molecules, so that essentially no cell growth, replication or expression of nucleic acid occurs after the inactivation. Preferably, the inactivation, while rendering nucleic acid incapable of further appreciable replication or expression, does not appreciably affect the activity of exogenous protein that is expressed on the surface of aAPCs prior to the inactivation.

The aAPCs are inactivated with an agent so as to effect nucleic acid (DNA or RNA) crosslinking. Exemplary crosslinking agents are described in U.S. Patent Application Publication No. US 2005/0054572; *Biodrugs*, Vol. 17(1), pp. 66-68 (2003) (amotosalen and light; INTERCEPT system);

Schneider et al., *Photochem. Photobiol.*, Vol. 67(3), pp. 350-357 (1998) (methylene blue and light); and U.S. Pat. No. 7,067,251 (psoralen and UVA). Crosslinking agents that are or become available in the art may be selected as desired by the artisan through routine experimentation to inactivate nucleic acid associated with the aAPCs in accordance with the invention. For example, to select a suitable crosslinking agent the artisan may take into account certain properties associated with a particular crosslinking agent, such as the nature of crosslinks produced by a particular crosslinking agent, its relative toxicity, potency, stability, reactivity, and other similar properties. Furthermore, plural crosslinking agents may be employed to inactivate aAPCs. Additionally, the treatment with the crosslinking agent may be concomitant with or subsequent to exogenous molecule expression and presentation on the APC cell surface. Preferred crosslinking agents possess a high affinity for nucleic acid (e.g., DNA and RNA) or both nucleic acid and polypeptide and interact with such molecules so that an adduct may be produced between the selected crosslinking agent and the nucleic acid or nucleic acid and polypeptide. Such a crosslinking agent may participate in either intrastrand or interstrand adduct formation. In the case of interstrand adduct formation, the nucleic acid component of the adduct comprises two DNA strands, two RNA strands, a DNA strand and an RNA strand, a DNA strand and a polypeptide, or an RNA stand and a polypeptide. In the case of intrastrand adduct formation, the nucleic acid component of the adduct comprises one DNA strand or one RNA strand. Preferably, the nucleic acid component of the adduct comprises DNA.

Illustrative crosslinking agents include members of the psoralen family of molecules and derivatives thereof (e.g., Lin et al., *Transfusion*, Vol. 37(4), pp. 423-435 (1997)); anthraquinones and anthraquinone derivatives (e.g., Kang et al., *Nucleic Acids Res.*, Vol., 24(20), pp. 3896-3902 (1996)); mitomycins, such as mitomycin C and mitomysin D (e.g., Tomasz, "The mitomycins: natural cross-linkers of DNA." In MOLECULAR ASPECTS OF ANTICANCER DRUG-DNA INTERACTIONS. VOLUME 2 (Neidle S and Waring M, eds.), pp. 313-349 (1994) and Warren et al., *Environ. Mol. Mutagen.*, Vol. 31(1), pp. 70-81 (1998)); nitrogen mustards, such as melphalan and chlorambucil (e.g., Dronkert et al., *Mutat. Res.*, Vol. 486(4), pp. 217-247 (2001) and Sancar et al., *Annu. Rev. Biochem.*, Vol. 73, pp. 39-85 (2004)); anthracyclines, such as adriamycin, daunomycin, epirubicin, and idarubicin (see e.g., Cutts et al., *Mol. Cancer. Ther.*, Vol. 2(7), pp. 661-670 (2003) and Sancar et al., *Annu. Rev. Biochem.*, Vol. 73, pp. 39-85 (2004)); platinum-containing coordination compounds, such as cisplatin, carboplatin, nedaplatin, and oxaliplatin (see e.g., Reedijk, *Proc. Natl. Acad. Sci. USA*, Vol. 100(7), pp. 3611-3616 (2003), Frankenberg-Schwager et al., *Toxicology*, Vol. 212, pp. 175-184 (2005), and Dronkert et al., *Mutat. Res.*, Vol. 486(4), pp. 217-247 (2001)) riboflavins; other aromatic compounds or dyes, such as thiazole orange dyes, methyl green dyes, ethidium bromide, and ethidium dimer (see e.g., Tuite et al., *Eur. J. Biochem.*, Vol. 243(1-2), pp. 482-492 (1997), Faridi et al., *J. Biomol. Struct. Dyn.*, Vol. 15(2), pp. 321-332 (1997), and Sancar et al., *Annu. Rev. Biochem.*, Vol. 73, pp. 39-85 (2004)); and the like.

Preferably, the crosslinking agent is photoactivatable. Accordingly, in preferred embodiments crosslinking is performed by incubating the aAPCs with a photoactivatable crosslinking agent and exposing the incubated aAPCs to a photoactivating dose of a suitable wavelength of radiation for a sufficient time to inactivate the aAPCs, e.g., by causing the crosslinking agent to form an adduct with nucleic acid associated with aAPCs. In preferred embodiments, the crosslinking achieves inactivation of both xenogenic nucleic acid and endogenous nucleic acid associated with aAPCs, so that they are killed or rendered essentially incapable of further replication or proliferation. Preferably, the crosslinking yields aAPCS that are inactivated and essentially free of contaminating microorganisms, such as bacteria and viruses, without substantially decreasing the antigen-presenting cell function of the aAPCs. Once thus inactivated the aAPCs are essentially metabolically inactive but retain the ability to present functional exogenous molecules—which were expressed and presented prior to the inactivation—on their surface, present selected peptide to naïve T cells, and activate naïve T cells to which the peptides have been presented.

Inactivation and sterility can be confirmed by, for example, infected cell viability assays; viral infectivity assays; viral activity assays; endogenous viral protein detection assays; endogenous viral nucleic acid detection assays; PCR-based assays or reverse-transcriptase (RT) PCR-base assays; xenogenic nucleic acid detection assays; flow cytometry; and/or FACS analysis (see, e.g., Belanger et al., 2000, *Transfusion* 40:1503, 2000). For example, insect cells, which may contain associated viral nucleic acid and other microbial nucleic acid in culture media, may be transfected with xenogenic nucleic acid encoding exogenous molecules and then subjected to the crosslinking. Supernatant obtained from the so-subjected cells may then be assayed using methods known or available in the art to determine the amount of plaque forming units (PFUs), which is a direct indication of viral nucleic acid activity. Similar methods may be employed to determine the activity of other non-viral microbial nucleic acid. Inactivated aAPCs of the invention preferably display essentially no PFUs. Suitable other assays known or available in the art, such as immunoassays to detect the presence of a viral coat protein, may also be used to confirm the absence of virus replication and transplantation of viral protein products.

In especially preferred embodiments, xenogenic nucleic acid that is associated with or derived from other components of the aAPCs, such as culture media, blood or blood products, and the like, is inactivated upon exposure to a photoactivatable crosslinking agent. Photoreaction is capable of generating broad safety margins in the disinfection of microbial products under gentle, physiologic conditions.

More preferably, the photoactivatable crosslinking agent is a member of the psoralen family of molecules, such as those illustrated in International Publication Nos. WO 91/06665 and WO 96/39820, Lin et al., 1997, *Transfusion*, Vol. 37(4), pp. 423-435, and Belanger et al., *Transfusion* 40:1503, 2000. Such crosslinking agents may be photoactivated by exposing them to a photoactivating dose of radiation. Methods for testing, manipulating, and optimizing, parameters such as crosslinking agent amount and concentration and radiation intensity and time duration may be routinely selected in light of guidance in the art (see, e.g., International Publication Nos. WO 96/39820 and WO 91/06665). The psoralen photoreaction is advantageous for inactivating both known and unknown viruses in active products. Psoralen-inactivated viruses have already proven useful as non-infectious antigens for use in immunoassays and as experimental vaccines (Hanson, *Blood Cells* 18:7, 1992).

Suitable devices that may be employed to deliver a photoactivating dose of radiation, and thereby achieve crosslinking, may be selected or designed based on teachings in the art, e.g., as exemplified in International Publication Nos. WO 96/39820 and WO 91/06665. Such illustrative devices may be suitably modified so that they are tailored to the needs of a particular embodiment of the invention. For example, devices having a source of electromagnetic radiation that is integrated into a photoactivation unit may comprise: means for providing appropriate wavelengths of electromagnetic radiation to cause photoactivation of at least one crosslinking agent; means for supporting at least one sample comprising the aAPCs, preferably a plurality of such samples, in a fixed relationship with the radiation-providing means during photoactivation; and means for maintaining the temperature of the samples within a desired temperature range during photoactivation. Thus, in an exemplary embodiment crosslinking may be performed by steps comprising: supporting a plurality of sample containers, each containing an aAPC composition and a photoactivatable crosslinking agent, in a fixed relationship with a fluorescent source of electromagnetic radiation; irradiating the plurality of sample containers simultaneously with electromagnetic radiation to cause photoactivation of the crosslinking agent; and maintaining the temperature of the composition in each container within a desired temperature range during photoactivation.

In especially preferred embodiments the crosslinking agent is a psoralen derivative. A psoralen derivative photoactivated by long-wave UV irradiation has been used in various applications to inactivate deoxyribonucleic acid and ribonucleic acid viruses (see, e.g., Brockstedt et al., *Nat. Med.*, Vol. 11(8), pp. 853-860 (2005); Lubaki et al., *AIDS Res. Hum. Retrovirusus*, Vol. 10(11), pp. 1427-1431 (1994)) and psoralens have been described as forming covalent monoadducts and crosslinks with pyrimidine bases of DNA and RNA upon illumunation with UVA light (Redfield et al., *Infect. Immun.*, Vol. 32(3), pp. 1216-1226). Additionally, Therakos has clinically tested a psoralen/UV treatment for lymphoma patients. Exemplary psoralen derivatives, which are compounds having a chemical structure comprising the psoralen core or motif, are shown below:

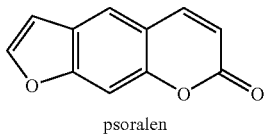
psoralen

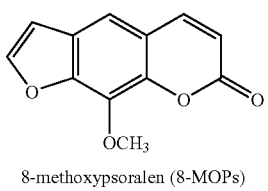
8-methoxypsoralen (8-MOPs)

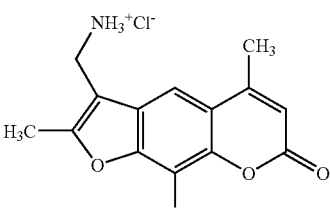
4'-(aminomethyl)-4,5', 8-psoralen

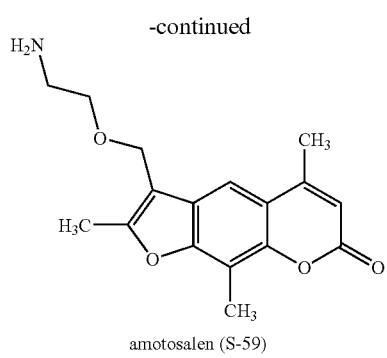
amotosalen (S-59)

Preferably, a clinical or similar high-purity grade of a psoralen derivative is employed for crosslinking nucleic acid associated with aAPCs. The psoralen derivative is contacted with aAPCs at a suitable concentration, e.g., from about 0.1 µg/ml to about 100 µg/ml, more preferably of from 1 µg/ml to 55 µg/ml, such as 1, 5, 10, 15, 20, 30, 40 or 55 µg/ml. The psoralen-treated aAPC composition is subsequently exposed to (irradiated with) UVA, which is long-wave (from about 320 nm to about 400 nm) ultraviolet radiation, for a time sufficient to achieve the desired degree of inactivation. For example, a UVA exposure of from about 1 minute to about 60 minutes, such as 1, 3, 4, 5, 10, 15, 20, 30, 45, 60 minutes, may be selected. The UVA intensity during this exposure is selected in view of the chosen exposure time period to achieve the desired degree of inactivation, for example, from about 0.1 to about 100 Joule/cm$^2$ (J/cm$^2$) and preferably, such as 1, 5, 10, 15, or 20, 40, 50 or 100 J/cm$^2$. Although crosslinking treatment with 8-MOPs plus 1 Joule/cm$^2$ for 2 minutes is sufficient to inactivate *Drosophila* cells, preferably the crosslinking also is performed so as to inactivate any viral contaminants while maintaining or enhancing APC function (in comparison with untreated APCs). In an exemplary embodiment, the dose of a psoralen derivative (5 mcg/ml; 8-MOPs) and UVA exposure (irradiation at 320-380 nm for 5 minutes) is similar to that used to inactivate HIV-1-infected cells (see Watson et al., *AIDS Res Hum Retroviruses* 6:503, 1990). This photoreaction is sufficient to inactivate Baculovirus isolated from infected Sf9 cells treated with psoralen/UV after infection. The viral stock obtained in the supernatant does not contain infectious virus, where control viral infected Sf9 cells contain significant amounts of PFUs after a single cycle of infection (8×10$^8$ PFU/ml). The photoreaction prevents the virus from replicating in the indicator cell line and producing infectious particles containing nucleic acid. In another exemplary embodiment, 2 mcg/ml of clinical-grade UVADEX® (8-MOPs) and UVA irradiation at 5 Joule/cm$^2$ for 10 minutes are used to inactivate 10$^8$ pfu insect virus.

An immunoassay for the presence of a viral coat protein is preferably performed to confirm the absence of virus replication and translation of viral protein products. Tests may be performed to confirm that psoralen/UV treatment of *Drosophila* cells cultured at 27° C. do not replicate, and that cell counts are negligible after 14 days in culture. The treatment prevents subsequent replication of the *Drosophila* cells, which remain inactive until they are lysed from lack of growth.

Various UVA devices emitting ultraviolet radiation in the 320-400 nm range are available or may be readily constructed using a suitable UVA-emitting source or broader-range ultraviolet radiation source with a filter or other means for restricting the radiation wavelength to within the UVA range. Such devices are said to have low end and high end wavelength "cutoffs", which do not allow wavelengths below or above such wavelength cutoffs to irradiate the psoralen-treated aAPCs. Such devices are also preferably capable of delivering substantially precise wavelengths of radiation, which have half-bandwidth distances of about 10 nm, more preferably about 8 nm, more preferably about 6 nm, more preferably no greater than 5 nm. A preferred wavelength of radiation used to photoactivate a crosslinking agent is about 365 nm with a 5 nm half-bandwidth. An exemplary device comprises an emitting source that comprises a high-intensity long-wavelength UV lamp equipped with a mercury flood bulb. While the position or orientation of the radiation-emitting source of such a device may be suitably selected, preferably the UVA source is positioned above the sample to be irradiated. Other exemplary UVA devices include modified irradiation systems such as model 4R4440 from Baxter Biotech (see also, Lin et al., 1997, *Transfusion*, Vol. 37(4), pp. 423-435) and those disclosed in International Publication No. WO 96/39820.

It may be desirable to admix the aAPCs and the crosslinking agent before or during the photoactivation process, which may be performed with, for example, a shaker that is positioned so that the aAPC composition and crosslinking agent may be thoroughly admixed. Furthermore, it may be desirable to carry out the photoactivation under essentially anaerobic conditions. Exemplary methods that may be employed to effect essentially anaerobic photoactivation are exemplified by Lin et al., 1989, *Blood*, Vol. 74, pp. 517-525, and Lin et al. 1997, *Transfusion*, Vol. 37, pp. 423-435.

In one preferred embodiment, a freeze-thaw cycle is performed before, during, or after the crosslinking. In an exemplary freeze-thaw cycle, the aAPCs may be frozen by contacting a suitable receptacle containing the aAPCs with an appropriate amount of liquid nitrogen, solid carbon dioxide (i.e., dry ice), or similar low-temperature material, such that freezing occurs rapidly. The frozen aAPCs are then thawed, either by removal of the aAPCs from the low-temperature material and exposure to ambient room temperature conditions, or by a facilitated thawing process in which a lukewarm water bath or warm hand is employed to facilitate a shorter thawing time. Additionally, aAPCs may be frozen and stored for an extended period of time prior to thawing. Frozen aAPCs may also be thawed and then lyophilized before further use. Preferably, preservatives that might detrimentally impact the freeze-thaw procedures, such as dimethyl sulfoxide (DMSO), polyethylene glycols (PEGs), and other preservatives, are absent from media containing aAPCs that undergo the freeze-thaw cycle, or are essentially removed, such as by transfer of aAPCs to media that is essentially devoid of such preservatives.

Various advantages may be achieved through practice of the invention. For example, the ability of psoralen/UV-treated cells, and those cells psoralen/UV-treated and frozen and thawed for 2 cycles, are better APCs than viable, live untreated *Drosophila* cells. The ability to maintain or even enhance the APC function of *Drosophila* cell line 668 with the psoralen/UV and psoralen/UV/freeze/thaw protocol help ensure that the *Drosophila* cells are inactivated and lysed prior to exposure to human CD8 cells. This adds a significant safety feature without diminishing the unique stimulation capacity of the aAPCs. The CD8 cells which are specifically stimulated by the psoralen/UV and psoralen/UV/frozen/thawed cells grow as efficiently as those stimulated with viable, live *Drosophila* cells. Also, the antigen-specific nature of the CD8 CTLs generated at the end of the ex vivo culturing cycle is greater than that detected with the untreated APC cells. The inventive method for viral and host cell nucleic acid inactivation prevents cell growth and viral replication in treated cells. The ability to maintain the important APC function of *Drosophila* cells while ensuring the safety of the cell therapy product is a very desirable result and should help alleviate concerns by better ensuring its safety, such that the cell therapy may now be considered a "dead" non-human cell rather than a xenotransplantation product.

In preferred embodiments MHC molecules encoded by xenogenic nucleic acid are expressed by the aAPCs as empty molecules. Such empty molecules are essentially devoid of any bound antigenic peptide or immunogenic peptide or fragments of such peptides. As such, the aAPCs may be loaded with one or more peptide species selected for loading, which "selected peptide" may comprise one or more antigenic peptide species, immunogenic peptide species, or fragments of such peptide species. In some embodiments, the empty MHC molecules expressed on the surface of the aAPCs are loaded with one peptide species. In other preferred embodiments, selected peptide comprising a plurality of species, such as from two to six or more species, is used to load empty MHC molecules. MHC molecule loading with the selected peptide may be performed at a suitable time after expression of exogenous protein on the surface of aAPCs has occurred. MHC molecule loading with selected peptide also may be performed prior to, concomitant with, or subsequent to inactivation of xenogenic nucleic acid as described above.

As mentioned above, the aAPCs are loaded with selected peptide. The exposure of the aAPCs to the selected peptide may be performed concomitant with, or subsequent to, expression of the above-described exogenous molecules on the surface of the modified cells. As a result of this exposure, the aAPCs are loaded with selected peptide, preferably so that the selected peptide occupies antigen or immunogen binding sites on MHC molecules expressed on the surface of aAPCs, which binding sites were devoid of bound peptide prior to exposure to the selected peptide. Once loaded, the selected peptide is capable of being presented to naïve T cells in a manner that elicits activation of the naïve T cells.

The selected peptide employed for loading empty exogenous MHC molecules is selected in accordance with the particular class of such MHC molecule(s) to be expressed by the aAPCs. Thus, in embodiments in which aAPCs are desired to express empty MHC Class I molecules, selected peptide that binds to such empty MHC Class I molecules is contacted with such aAPCs so that Class I molecules are loaded with such selected peptide. In embodiments in which the aAPCs are desired to express empty MHC Class II molecules, selected peptide that binds to such empty MHC Class II molecules is contacted with such aAPCs so that Class II molecules are loaded with such selected peptide. In embodiments in which both MHC Class I and MHC Class II molecules are to be expressed by aAPCs, both Class I-binding selected peptide and Class II-binding selected peptide may be used to contact the APCs so that both Class I and Class II molecules are loaded with selected peptide. In embodiments in which one peptide species is selected, that selected peptide species comprises a plurality of peptide molecules, each of which is identical to the other in amino acid composition and sequence. In embodiments in which two or more peptide species are selected, each of the two or more selected peptide species independently comprises a plurality of peptide molecules, each of which is identical to the other in amino acid composition and sequence. These two or more species are each used to contact the aAPCs, either simultaneously or at distinct instances. In each of these embodiments, multi-antigenic or multi-immunogenic MHC-peptide complexes are produced on the aAPCs. Selected peptide loading onto empty MHC molecules preferably occurs under conditions that approximate biological binding conditions, which may be approximated in vitro, ex vivo, or in vivo.

Exemplary peptide species that may be selected include the following, where the protein from which each peptide is derived and the sequence identifier assigned to each peptide are indicated in parentheses: SILSLKEAST (C-Lectin; SEQ ID NO:1), KMASRSMRL (C-Lectin; SEQ ID NO:2), ALALAALLVV (Pec 60; SEQ ID NO: 3), ALLVVDREV (Pec60; SEQ ID NO: 4), YMNGTMSQV (Tyrosinase; SEQ ID NO:5), YMDGTMSQV (Tyrosinase; SEQ ID NO:6), ITDQVPFSV (gp100; SEQ ID NO:7), YLEPGPVTA (gp100; SEQ ID NO:8), AAGIGILTV (MART-1; SEQ ID NO:9), ELAGIGILTV (MART-1; SEQ ID NO:10), CLTSTVQLV (Her-2/neu; SEQ ID NO:11), HLYQGCQVV (Her-2/neu; SEQ ID NO:12), KIFGSLAFL (Her-2/neu; SEQ ID NO:13), IISAVVGIL (Her-2/neu; SEQ ID NO:14), PLTSIISAV (Her-2/neu; SEQ ID NO:15), VMAGVGSPYV (Her-2/neu; SEQ ID NO:16), VLVKSPNHV (Her-2/neu; SEQ ID NO:17), ELVSEFSRM (Her-2/neu; SEQ ID NO:18), YLSGANLNL (CEA; SEQ ID NO:19), GPLTPLPV (AES; SEQ ID NO:20), SLLMWITQC (NY-ESO-1; SEQ ID NO:21), KALFAGPPV (CA-125; SEQ ID NO:22), YLETFREQV (CA-125; SEQ ID NO:23), GLQSPKSPL (CA-125; SEQ ID NO:24), VLLKLRRPV (CA-125; SEQ ID NO:25), ELYIPSVDL (CA-125; SEQ ID NO:26), SLLMWITQV (NY-ESO-1; SEQ ID NO:27), ILAKFLHWL (Telomerase; SEQ ID NO:28), STAPPVHNV (MUC-1; SEQ ID NO:29), FLWGPRALV (MAGE-3; SEQ ID NO:30), FMWGNLTLA (CA-125; SEQ ID NO:31), RLVDDFLLV (Telomerase; SEQ ID NO:32), HLSTAFARV (G250; SEQ ID NO:33), QLSLLMWIT (NY-ESO-1; SEQ ID NO:34), ELWTHSYKV (FBP; SEQ ID NO:35), KVAELVHFL (MAGE-3; SEQ ID NO:36), YIFATCLGL (MAGE-3; SEQ ID NO:37), HLYIFATCL (MAGE-3; SEQ ID NO:38), MLMAQEALAFL (CAMEL; SEQ ID NO:39), STLEKINKT (SSX-4; SEQ ID NO:40), KASEKIFYV (SSX-2; SEQ ID NO:41), SLLMWITQCFL (NY-ESO-1; SEQ ID NO:42), ELTLGEFLKL (Survivin; SEQ ID NO:43), LTLGEFLKL (Survivin; SEQ ID NO:44), SLLEKREKT (SP17; SEQ ID NO:45), TLGEDDPWL (SART-1; SEQ ID NO:46), KLGLKPLEV (SART-1; SEQ ID NO:47), YLWTSAKNT (SCP-1; SEQ ID NO:48), STAPPAHGV (MUC-1; SEQ ID NO:49), GMGSEELRL (LIVIN; SEQ ID NO:50), SLGSPVLGL (LIVIN; SEQ ID NO:51), YLFFYRKSV (hTRT; SEQ ID NO:52), CQQEETFLL (CA-125; SEQ ID NO:53), TLAKFSPYL (PRAME; SEQ ID NO:54), NLTHVLYPV (PRAME; SEQ ID NO:55), STFKNWPFL (Survivin; SEQ ID NO:56), SLLQHLIGL (PRAME; SEQ ID NO:57), FLDQRVFFV (gp100; SEQ ID NO:58), FLDQRVFVV (gp100; SEQ ID NO:59), FLDQVAFVV (gp100; SEQ ID NO:60), GLDREQLYL (MUC-16; SEQ ID NO:61), VMQHLLSPL (MUC-16; SEQ ID NO:62), QQTHGITRL (MUC-16; SEQ ID NO:63), LQPLSGPGL (MUC-16; SEQ ID NO:64), TLDRDSLYV (MUC-16; SEQ ID NO:65), QLYLELSQL (MUC-16; SEQ ID NO:66), KVLEYVIKV (MAGE-1; SEQ ID NO:67), KVADLVGFL (MAGE-1; SEQ ID NO:68), KTWGQYWQV (SEQ ID NO:70) and VLDGLDVLL (SEQ ID NO: 71). Preferred peptides include Topoisomerase II, Integrin β8 subunit precursor, MUC-1, MAGE-B2, STAT 1, γ-Catenin, and H-RYK (RTK 6). Other suitable peptides may be routinely selected. See, e.g., U.S. Patent Application Publication No. 2003/0022820 for some illustrative peptide species.

Selected peptide species may be presented to the cells and loaded onto aAPCs via a variety of means and techniques now known or that become available in the art. The peptides may be presented in a manner that allows them to enter an intracellular pool of peptides. For example, peptides may be presented via osmotic loading. Preferably, peptides are added to the aAPC system culture medium. The peptides may be added to the culture medium in the form of an intact polypeptide or protein that is subsequently degraded via cellular processes, such as enzymatic degradation. Alternatively, the intact polypeptide or protein may be degraded via some other means, such as chemical digestion (e.g., cyanogen bromide) or proteases (e.g., trypsin and chymotrypsin) prior to addition to the aAPC system culture medium. Alternatively, an entire protein or polypeptide sequence may be cloned into an appropriate vector and inserted into a prokaryotic cell, whereby the cell generates significant amounts of the antigenic polypeptide that are then harvested, purified, and digested into peptides that are then added to the aAPC system culture medium. Purification of proteins or peptides may be achieved through various suitable techniques that are known or become available in the art, such as immunoaffinity chromatography, affinity chromatography, protein precipitation, buffer exchanges, ionic exchange chromatography, hydrophobic interaction chromatography, or size exclusion chromatography.

In preferred embodiments, aAPCs are inactivated at a point subsequent to the expression of exogenous MHC and assisting molecules, presentation of such molecules on the surface of the aAPCs, and loading of presented MHC molecules with selected peptide. Accordingly, such inactivated and selected peptide loaded aAPCs, while rendered essentially incapable of proliferating or replicating, retain selected peptide presentation function, and preferably also retain naïve T cell activation function. Furthermore, fragments of aAPCs fragments, such as intact cell membranes and fragments of cell membranes, which contain selected peptide-loaded MHC and assisting molecules, may be optionally employed to activate naïve T cells. Any suitable method known or available in the art may be employed to prepare, isolate, and manipulate such aAPC fragments.

As the aAPCs prepared and inactivated as described above present exogenous empty MHC molecules, a sufficient amount of selected peptide advantageously may be added to the aAPCs such that a high density of selected peptide-MHC complexes on the aAPC surface is achieved, which high density is substantially greater than a density observed with wild type mammalian APCs. A naïve T cell/inactivated aAPC culture may be maintained for as long a time as is appropriate to activate and enrich for a therapeutically effective population of CTLs. For example, the naïve T cell/inactivated aAPC culture time duration is from about one day to about ten days, such as from two to nine days, three to eight days, or four to six days.

In a preferred embodiment, aAPCs or aAPC fragments as prepared and inactivated as described above possess enhanced APC function relative to APC function possessed by APCs that have not been so inactivated. Enhanced APC function may be reflected by a greater measure of CTL activity in CTLs that are activated by contacting the inactivated aAPCs relative to a measure of CTL activity in CTLs that are activated by contacting APCs that are not inactivated. The CTL activity may measured by one or more parameters of CTL activation, such as a degree of cell surface protein expression by one or more proteins indicative of CTL cell activation (such as CD69 cell surface expression), a degree of differentiation, a degree of specific cytotoxic killing ability, a degree of specific cell lysis, or a degree of CTL-associated cytokine production. Furthermore, activated T cells may be detected or isolated by peptide-MHC (pMHC) tetramer staining, wherein detected activated T cells are specific for selected peptide presented by the aAPCs. In a preferred embodiment, inactivation is attained by complexing the aAPCs with a psoralen derivative and exposing the complex to UVA so as to achieve enhanced CD69 expression.

Activated T cells may be separated from the aAPCs using a suitable technique known or available in the art. For example, monoclonal antibodies specific for the aAPCs, for the peptides loaded onto the aAPCs, or for the activated T cells (or a portions thereof) may be employed to bind an appropriate complementary ligand. Antibody-tagged cells may then be extracted from the aAPC/activated T cell admixture by a suitable technique, such as an immunoprecipitation or immunoassay method. Alternatively, a separation step may be omitted completely and the inactivated aAPCs may be left in culture with the activated T cells.

In a preferred embodiment, naïve CD8+ T cells are selected for activation, and desired amounts of resulting CTLs are employed to prepare a cell therapy product for therapeutic administration. Preferably, prior to administration one or more quality assurance tests are performed on the activated T lymphocytes or cell therapy. In preferred embodiments, the quality assurance testing comprises performing one or more tests to confirm: HLA match between patient and T lymphocytes; flow cytometry analysis ($CD8^+$, $TCR^+$); sterility (no bacterial or fungal growth); gram-stain negative for bacteria; mycoplasma negative for PCR/ELISA; no residual *Drosophila* DNA; absence of insect virus cDNA; viability (>72% viable); and cytolytic activity by CTL assay.

To treat a subject, an effective amount of a cell therapy product according to the invention is administered to a subject suffering from or diagnosed as having such a disease, disorder, or condition. An "effective amount" is an amount or dose sufficient to generally bring about a desired therapeutic or prophylactic benefit in patients in need of such treatment. Effective amounts or doses of the cell therapy products of the present invention may be ascertained by routine methods such as modeling, dose escalation studies or clinical trials, and by taking into consideration routine factors, e.g., the mode or route of administration or product delivery, the pharmacokinetics of the cell therapy product, the severity and course of the disease, disorder, or condition, the subject's previous or ongoing therapy, the subject's health status and response to drugs, and the judgment of a treating physician. As exemplary dosage amounts, cell populations may comprise from about $1 \times 10^6$ to about $1 \times 10^{12}$ activated T cells, such as $1 \times 10^8$ to $1 \times 10^{11}$ or $1 \times 10^9$ to $1 \times 10^{10}$ activated T cells for an adult human.

The cell therapy product is prepared as a therapeutic composition comprising activated T cells and a vehicle suitable for the maintenance of the activated T cells until they are infused into the subject, such as a pharmaceutically acceptable diluent or solvent. In a preferred embodiment, the cell therapy product comprises from about $1 \times 10^9$ to about $10 \times 10^9$ CTLs in a solution comprising Lactated Ringer's Injection Solution, USP (76% (v/v), 5% dextrose normal saline (D5NS; 4% (v/v)), and 25% human serum albumin (HSA; 20% (v/v)).

Any suitable technique for administering compositions comprising cellular components into a subject may be employed. For example, administration of activated CTLs cells via intravenous infusion may be employed. Multiple infusions may be required or indicated, and these infusions may occur over a period of several weeks or longer. Exemplary techniques are described in, for example, U.S. Pat. Nos. 4,844,893 and 4,690,915.

Optionally, the cell therapy products or preparations may be supplemented to include other immunomodulatory, preferably immunostimulatory, components in addition to selected peptide-loaded aAPCs. Such additional components may be added prior to, concomitant with, or subsequent to contacting naïve T cells with the peptide-loaded aAPCs. The selection of desired time points and dosage concentrations and frequencies at which such supplemental immunomodulatory, preferably immunostimulatory, components are added may be selected according to relevant considerations, such as desired proliferation rate, expansion rate, cell number, longevity, or immunogenicity. Supplemental or immunostimulatory components may be, for example, one or more leukocytes other than non-naïve T cells, cytokines, lymphokines, chemokines, and antibodies. Exemplary leukocytes that may be selected include adherent cells, such as non-CD8 adherent cells, $CD14^+$ adherent cells, monocytes, macrophages, helper T cells, memory T cells, and other leukocytes that may impart an immunomodulatory, preferably immunostimulatory, effect or stimulus. Such leukocytes may be of autologous or heterologous origin. In a preferred embodiment, selected leukocytes are of autologous origin. Exemplary cytokines include interleukins, such as IL-1, IL-2, IL-3, IL-4, IL-5, IL-6, IL-7, IL-8, IL-9, IL-11, IL-12, IL-15, IL-17, IL-21, interferons, such as γ-interferon, and tumor necrosis factors (TNFs), such as TNF-α (see, e.g., Tizard I., IMMUNOLOGY: AN INTRODUCTION, $3^{rd}$ Edition, pp. 129-143, (1992) or CD70 (see for example, Gen Bank accession number L08096 and NCBI accession number NM_001252), LT, 4-1 BBL and OX40L; U.S. Patent Application Publication No. 2002/0119121; and International Publication No. WO 2002/022648). The cytokines may be of recombinant or natural origin. In a preferred embodiment, selected cytokines are of recombinant origin. Exemplary antibodies include monoclonal anti-CD3 antibodies, such as that marked as ORTHOCLONE OKT®3 (muromonab-CD3).

In an especially preferred embodiment, autologous non-CD8, $CD14^+$ adherent cells, IL-2, IL-7, and monoclonal anti-CD3 antibody preparation (OKT®3) are employed as additional immunostimulatory components in cell therapy preparation methods. In such embodiments, naïve T cells that have been subjected to primary stimulation with selected peptide-loaded aAPCs are subjected to restimulation by contacting them with effective amounts of recombinant IL-2 and recombinant IL-7 (e.g., about 1-100 Units/ml IL-2 and preferably 1, 10, 15, 20, 50 or 100 Units/ml IL-2 and about 1-100 Units/ml IL-7, and preferably 1, 10, 15, 20, or 50 Units/ml IL-7), and then contacting them with an effective amount of autologous, selected peptide-loaded, non-CD8, $CD14^+$ adherent cells (e.g., about one non-CD8, $CD14^+$ adherent cell for every four primary-stimulated naive T cells). Preferably, the time duration of the IL-2/IL-7 and $CD14^+$ adherent cell contact is about two days and from about three to about four days, respectively, and each restimulation is repeated in sequence at least once. After at least two restimulation regimens, a non-specific T cell expansion regimen comprises contact with IL-2 and anti-CD3 (e.g., OKT®3) for about two to about five days.

In other preferred embodiments, autologous $CD4^+$ helper T cells and IL-2, IL-7, IL-12, IL-15, IL-17, or IL-21 are contacted with naïve T cells prior to, concomitant with, or subsequent to primary stimulation or restimulation. Preferably IL-2 is used in combination with at least one of IL-7, IL-15 or IL-21. Where IL-15 is used, preferred effective amounts of IL-15 are about 1-100 ng/ml and preferably 1, 10, 20, 25, 40, or 50 ng/ml IL-15. Similarly, where IL-21 is used, preferred effective amounts of IL-15 are about 1-100 ng/ml and preferably 1, 10, 20, 25, 40, or 50 ng/ml IL-21. In such preferred embodiments, naïve T cells may be directed to become memory T cells. Such a $CD4^+$ helper T cell regimen may be employed in addition to or in lieu of any of the restimulation or non-specific T cell expansion procedures described above, rendering memory T cells that may tolerate multiple rounds of restimulation ex vivo. Additionally, a cell therapy product comprising such memory T cells, when administered to a subject, may then be expanded and stimulated in vivo when encountered with selected peptide and other activating cues. Processes generally relating to the preparation of helper T cells and their incorporation into IL-2, IL-7, IL-12, IL-15, IL-17, and/or IL-21 assisted stimulation or expansion of naïve T cells to become memory T cells or CTLs may be found in, e.g., U.S. Patent Application Publication No. 2002/0119121 and International Publication No. WO 2002/022648.

In order to treat a subject, a cell therapy product is preferably administered to the subject from whom the pheresis product used to prepare the cell therapy product was originally obtained. Therefore, a subject who is treated with a cell therapy product is preferably administered a cell therapy product that comprises autologous activated T cells, and more preferably that comprises CTLs.

Exemplary diseases, disorders, or conditions that may be treated with a cell therapy product in accordance with the invention include, for example, include immune disorders, such as immune deficiency disorders, autoimmune disorders, and disorders involving a compromised, insufficient, or ineffective immune system or immune system response; infections, such as viral infections, bacterial infections, mycoplasma infections, fungal infections, and parasitic infections; and cancers, such as malignant melanoma, multiple myeloma, prostate cancer, lymphoma, non-Hodgkin's lymphoma, leukemia, acute lymphoblastic leukemia, acute myeloid leukemia, chronic lymphocytic leukemia, chronic myeloid leukemia, Burkitt's lymphoma, thyroid cancer, uterine cancer, kidney cancer, ovarian cancer, lung cancer, breast cancer, liver cancer, pancreatic cancer, prostate cancer, colon cancer, skin cancer, stomach cancer, cervical cancer, head and neck cancer, glioma, and brain tumor.

Treatment of a disease, disorder, or condition with a cell therapy product in accordance with the invention may occur before, concomitant with, or after other treatment with other therapeutic products or regimens. Exemplary additional regimens, components, or modalities that may be used in conjunction with administration of the inventive cell therapy product include, for example: immunostimulatory, immunosuppressive and other immunotherapy regimens, such as cytokine, lymphokine, chemokine, interleukin, or interferon administration; lymphodepleting and myeloblative regimens, such as denileukin diftitox (DAB-IL2) or cladribine administration; and traditional chemotherapy and radiation treatments. In a preferred embodiment, a lymphodepleting treatment regimen, such as that disclosed in U.S. Provisional Application No. 60/778,516, is employed in conjunction with treatment with the cell therapy product.

Accordingly, naïve T cells advantageously may be obtained from a subject suffering from a condition or disease treatable with the inventive cell therapy product prior to the initiation of another treatment or therapy that may interfere with, attenuate, or limit the activation of the naïve T cells. For example, in the treatment of an individual with a neoplasia or tumor, a lympapheresis product comprising naïve T cells may be obtained prior to the initiation of chemotherapy or radiation treatment and kept in culture. The naïve T cells may then activated in accordance with the present invention, thereby providing a cell therapy product, which may be infused into the subject prior to, concomitant with, or after other treatment regimens.

Other embodiments, features, and advantages of the invention are further illustrated by reference to the following examples.

EXAMPLES

Materials

Tyrosinase Peptide-YMNGTMSQV.    (SEQ ID NO: 5)

A tyrosinase peptide (tyr 369-377), corresponding to amino acids 369-377 of human tyrosinase, is manufactured and purified using GLP compliance standards (Synpep Corporation). The peptide powder as received from the manufacturer (Synpep Corporation) is dissolved in dimethylsulfoxide (DMSO) to achieve a stock peptide solution at a concentration of 10 mg/mL, and is stored at −72° C. to −88° C. prior to use. This stock peptide solution is mixed in equal parts with other peptide stock solutions (also at a concentration of 10 mg/ml) to generate combination peptide solutions for use in loading xAPCs. The combination peptide solutions are aliquoted into sterile vials in a Class 10,000 clean room under aseptic conditions in a Class II biosafety cabinet.

Tyrosinase Peptide - YMDGTMSQV    (SEQ ID NO: 6)

A deamidated form of the tyr 369-377 peptide described above, which contains an aspartic acid residue in place of an asparagine residue at position three of the peptide, is manufactured and purified using GLP compliance standards (Synpep Corporation). This deamidation form is called tyr 369-377d. The peptide powder received from the manufacturer is dissolved in dimethylsulfoxide (DMSO) to achieve a stock peptide solution at a concentration of 10 mg/mL, and is stored at −72° C. to −88° C. prior to use.

MART-1 Peptide - AAGIGILTV    (SEQ ID NO: 9)

A MART-1 peptide (MART-1 27-35), corresponding to amino acids 27-35 of human MART-1, is manufactured and purified using GLP compliance (Synpep Corporation). The peptide powder is dissolved in dimethylsulfoxide (DMSO) to achieve a stock peptide solution at a concentration of 10 mg/mL, and is stored at −72° C. to −88° C. prior to use.

gp100 Peptide - ITDQVPFSV    (SEQ ID NO: 7)

A gp100 peptide (gp100 209-217), corresponding to amino acids 209-217 of human gp-100, is manufactured and purified using GLP compliance standards (Synpep Corporation). The peptide powder is dissolved in dimethylsulfoxide (DMSO) to achieve a stock peptide solution at a concentration of 10 mg/mL, and is stored at −72° C. to −88° C. prior to use.

gp100 Peptide - KTWGQYWQV    (SEQ ID NO: 70)

A gp100 peptide (gp100 154-162), corresponding to amino acids 154-162 of human gp100, is manufactured and purified using GLP compliance standards. The peptide powder as received from Synpep Corporation is dissolved in dimethylsulfoxide (DMSO) to achieve a stock peptide solution at a concentration of 10 mg/mL, and is stored at −72° C. to −88° C. prior to use.

```
gp100 Peptide - YLEPGPVTA         (SEQ ID NO: 8)
```

A gp100 peptide (gp100 280-288), corresponding to amino acids 280-288 of human gp100, is manufactured and purified using GLP compliance standards by Synpep Corporation. The peptide powder is dissolved in dimethylsulfoxide (DMSO) to achieve a stock peptide solution at a concentration of 10 mg/mL, and is stored at −72° C. to −88° C. prior to use.

Each of the aforementioned peptides, as well as the CD8 alpha chain peptide (AAEGLDTQRFSG; SEQ ID NO:83) described below was generated according to the method of Merrifield (Merrifield, *J. American Chemical Society*, Vol. 85, pp. 2149-2154 (1963)) using BOC-chemistry on ABI #430 (HOBt-DCC chemistry) or ABI #431 (HBTV chemistry) peptide synthesizers. Cleavage of protected peptides from the resin was done with 90% hydrogen fluoride 10% anisole at −4° C. for one hour. Peptides were purified by C18 reversed-phase HPLC using a mixture of 0.1% trifluoroacetic acid (TFA) in $H_2O$ and 0.1% TFA in acetonitrile. Purified peptides were analyzed by analytical HPLC coupled with electrospray mass spectrometry and by amino acid analysis. These peptides were used as trifluoroacetate salts.

Isolex 300i Disposable Tubing Set

The Isolex 300i Disposable Tubing Set is a single-use, sterile, nonpyrogenic, closed fluid path system (Baxter) used with the Isolex 300i Magnetic Cell Selection System, and is stored at room temperature (RT) prior to use. It contains a spinning membrane assembly, transfer bags, tubing manifolds, collection bags, and primary and secondary separation containers and tubing connectors to allow for aseptic connections. Isolex disposable tubing sets are sterilized by gamma irradiation.

```
                                  (SEQ ID NO: 83)
CD8 Alpha Chain Peptide - AAEGLDTQRFSG
```

CD8 alpha light chain peptide (AAEGLDTQRFSG; SEQ ID NO:83) is purified and manufactured under GLP compliance standards. The CD8 alpha chain peptide is used in $CD8^+$ T cell isolation processes to release $CD8^+$ T cells captured using an anti-CD8 (37B1A) antibody and the Isolex 300i Magnetic Cell Selection System. Each lot of peptide is manufactured by Synpep Corporation to meet pharmaceutical grade standards, and is tested for peptide sequence, purity, molecular weight, and appearance. The CD8 alpha chain peptide, received as a powder, is further processed to create a stock solution of 10 mg/ml. This stock solution is diluted in DPBS, filtered through a 0.2-μm filter, aliquoted into sterile vials, and stored at −72° C. to −88° C. prior to use. Vialing of the peptide reagent is performed in a Class 10,000 clean room under aseptic conditions in a Class II biosafety cabinet.

Dulbecco's Phosphate Buffered Saline (DPBS), 1× Concentration

Sterile, non-pyrogenic Dulbecco's phosphate buffered saline (DPBS) solution (Invitrogen Corporation) is stored at RT prior to use. DPBS is used for the following procedures: running the Isolex 300i Magnetic Cell Selection System during the selection of $CD8^+$ T cells and $CD8^-$ T cells; washing non-adherent cells during restimulation steps and washing unbound OKT3 monoclonal antibody during non-specific expansion; and diluting human β2 microglobulin, IL-7, CD8 peptide, and OKT3.

Anticoagulant Sodium Citrate Solution

A sterile, nonpyrogenic anticoagulant sodium citrate solution, USP (Baxter Fenwal), is stored at room temperature (RT) prior to use. Sodium citrate solution is used as a buffer additive for running the Isolex 300i Magnetic Cell Selection System for selection of $CD8^+$ T cells and $CD8^-$ T cells.

Non-vented T-75 Flasks

Non-vented T-75 flasks are used to grow host cells and xAPCs. The treated cell culture flasks have a surface area of 75 $cm^2$ and are sterile, non-pyrogenic, and made of a clear polystyrene material. The T-75 flasks are sterilized by gamma irradiation and certified to meet sterility assurance of $10^{-5}$ and the presence of pyrogens at <0.5 EU/mL. The T75 flasks are stored at RT when not in use.

Schneider's *Drosophila* Medium (1× Concentration)

Schneider's *Drosophila* medium is a culture medium used for culturing *Drosophila* cells. Each lot of medium is tested by the supplier (Invitrogen Corporation) for osmolarity, pH, sterility, and the ability to sustain the growth of *Drosophila* cells. Schneider's *Drosophila* medium is stored at 2° C. to 6° C. prior to use.

Geneticin (G418) (50 mg/mL)

Geneticin (Invitrogen Corporation) is a selective antibiotic used in the culture of *Drosophila* cells for maintaining expression of exogenous molecules encoded by xenogenic nucleic acid. Geneticin is supplied as a sterile stock solution, and is stored at 2 to 6° C. prior to use.

HYQ SFX Insect Medium (1× Concentration)

Hyclone's SFX Insect Medium (Hyclone Corporation) is a serum-free culture medium used during the peptide loading of xAPCs, and is stored at 2° C. to 6° C. prior to use. This medium does not contain products of bovine origin.

Copper (II) Sulfate Pentahydrate ($CuSO_4$)

Copper sulfate pentahydrate is used for induction of modified host cells to express human HLA, co-stimulatory, and adhesion molecules. The reagent is received as a crystalline powder. The stock solution is formulated by dissolving the $CuSO_4$ in endotoxin-free sterile water to achieve a concentration of 200 mM and aseptically filtering the solution through a 0.2-μm filter into a sterile container in a Class II biosafety cabinet. The filtered stock solution is stored at 2° C. to 6° C. prior to use.

Calcium Chloride Hydrate (1M)

Calcium chloride hydrate is used for clotting of autologous plasma obtained from the lymphapheresis product to generate autologous serum used in $CD8^+$ T cell isolation or activation processes. Calcium chloride hydrate is received as a crystalline powder, is compounded into a stock solution, and stored at 2° C. to 6° C. prior to use. The stock solution is formulated by dissolving calcium chloride in endotoxin-free sterile water and aseptically filtering through a 0.2-μm filter into a sterile container in a Class II biosafety cabinet.

Distilled Water

Cell culture grade distilled water, which is obtained by membrane-filtering and endotoxin-screening (Invitrogen Corporation), is used as a solvent for the preparation of stock solutions of copper sulfate, calcium chloride, and interleukin-2 (IL-2) and is used at RT prior to use.

Acetic Acid (17.4M)

Acetic acid used for the preparation of stock solutions of IL-2 is obtained from Sigma Corporation and stored at RT prior to use.

FICOLL-PAQUE® Plus (1× Concentration)

Following isolation of CD8+ T cells and CD8− T cells with the Isolex 300i Magnetic Cell Selection System, mononuclear cells from the non-CD8+ fraction are further fractionated using FICOLL-PAQUE® Plus, a Ficoll reagent without any animal components available from Amersham Pharmacia Biotech used to remove dead cells, neutrophils, and red blood cells. The reagent is stored at RT prior to use.

PENTASPAN® (1× Concentration)

PENTASPAN® (B. Braun Medical Inc) is a sterile solution of 10% pentastarch in 0.9% sodium chloride for clinical use (NDC 0264-1972-10), and is stored at RT prior to use. It is used as a cryoprotectant in the cryopreservation of isolated CD8− T cells and CD8+ T cells.

Dimethyl Sulfoxide (DMSO), 1× Concentration

DMSO is used as a cryoprotectant in the cryopreservation of isolated CD8− T cells and CD8+ T cells. The DMSO solution, available from Sigma-Aldrich, is stored at RT prior to use.

RPMI Culture Medium (1× Concentration)

RPMI culture medium (Invitrogen Corporation), which is serum- and antibiotic-free, is used to grow T cells. RPMI culture medium is stored at 2 to 6° C. prior to use.

L-Glutamine (200 mM; 100× Concentration)

L-Glutamine (USP), 200 mM, available from Invitrogen Corporation, is used as an RPMI culture medium supplement, and is stored at −80° C. prior to use.

MEM Sodium Pyruvate Solution (100 mM; 10× Concentration)

MEM sodium pyruvate solution (100 mM), available from Invitrogen Corporation, is used to supplement RPMI medium, and is stored at 2 to 6° C. prior to use.

Non-Essential Amino-Acids (10 mM; 100× Concentration) Non-essential amino-acids from Invitrogen Corporation used to supplement RPMI medium are stored at 2 to 6° C. prior to use.

HEPES Buffer Solution, (1M; 200× Concentration)

HEPES buffer solution (Invitrogen Corporation), used to supplement RPMI medium, is stored at 2° C. to 6° C. prior to use.

T-75 Flasks—Vented

Vented T-75 flasks are used in the stimulation and restimulation of CD8+ T cells. The treated cell culture flasks have a surface area of 75 cm², are sterile, non-pyrogenic, and made of a clear polystyrene material. Flasks are stored at RT prior to use. Each flask had a vented polyethylene cap with a PTFE 0.2-μm hydrophobic air vent. The T-75 flasks are sterilized by gamma irradiation.

X-Vivo 10-Cell Medium (1× Concentration)

X-vivo 10-cell culture medium, supplied by BioWhittaker, is stored at 2° C. to 6° C. prior to use. This medium, which is serum-, phenol red-, and antibiotic-free, is used during the phase of non-specific expansion of T cells activated by exposure to peptide-loaded xAPCs.

Leibovitz's L-15 Medium Without Glutamine (1× Concentration)

Leibovitz's L-15 medium (without L-glutamine), a cell culture medium available from Sigma-Aldrich, is stored at 2° C. to 6° C. prior to use during peptide-loading steps of the T cell activation process.

T-225 Flasks—Vented

Vented T-225 flasks are used in OKT®3-stimulation of T cells during non-specific cell expansion of T cells. The treated cell culture flasks have a surface area of 225 cm², are made of clear polystyrene material sterilized by gamma irradiation. Each flask has a vented polyethylene cap with a PTFE 0.2-μm hydrophobic air vent. Flasks are stored at RT prior to use.

3-Liter Lifecell Tissue Culture Bags

Sterile single-use Lifecell bags with 300 mL capacity are stored at RT prior to use.

0.9% Sodium Chloride Injection

A 0.9% sodium chloride solution, USP, available from Baxter Fenwal Laboratories, is used for cell washing procedures during harvesting of T cells. The solution, which is sterile, non-pyrogenic, and free of animal components, is stored at RT prior to use.

5% Dextrose and 0.9% Sodium Chloride Solution

An injectable solution of 5% dextrose and 0.9% sodium chloride, USP (Baxter Fenwal Laboratories), is obtained as a sterile, non-pyrogenic solution free of animal components. The solution, which is used as a storage buffer for activated T cells, is stored at RT prior to use.

0.9% Lactated Ringer's Solution

A 0.9% Lactated Ringer's solution, USP (Baxter Healthcare Laboratories), which is a sterile, low-endotoxin solution of calcium chloride, potassium chloride, sodium chloride, and sodium lactate in water for injection (free of animal components), is stored at RT prior to use in harvesting and suspending T cells.

Final Product Bag

The final product bags used to contain the activated and processed T cells are single-use, sterile infusion bags with a 1000-mL capacity comprised of biocompatible plastic. Bags are stored at RT prior to use and available from Baxter Fenwal Laboratories.

1.8-mL NUNC® Cryotubes

NUNC® cryotubes (1.8 mL) may be used to freeze down host cells, xAPCs, and surplus CD8+ T cells generated during the activation process.

Human Peripheral Blood Lymphocytes

Lymphapheresis products are collected from human subjects diagnosed with melanoma and are stored at room temperature prior to use for the generation of an autologous, patient-specific cell product.

Autologous Human Serum

Autologous human serum is used as a protein source for culturing of isolated T cells. Autologous human plasma is prepared from lymphapheresis product by adding calcium chloride to achieve fibrin clotting and then collecting the liquid serum phase. The collected liquid serum phase is stored at 4° C. for short-term storage and at −80° C. for long-term storage.

*Drosophila* Master Cell Bank

A *Drosophila* xAPC line derived from the xenogenic *Drosophila* clone B, which is used as a seed stock to create a continuous *Drosophila* xAPC culture, is obtained as described below.

Fetal Bovine Serum

Fetal bovine serum (FBS), which is used as a protein source for the growth of host cells or xAPCs cells, is stored at −80° C. The FBS, available from Gemini Bioproducts, is processed from bovine fetal blood from animals of United States origin. The maternal animals from which the blood is derived are free of infectious and contagious diseases and injurious parasites.

Anti-CD8 Monoclonal Antibody (37B1A), 10.0 mg/mL

Anti-CD8(37B1A) is a murine monoclonal antibody (mAb) directed against the CD8 antigen of T cells, which is used to select CD8+ T cells with the Isolex 300i Magnetic Cell Selection System. The concentrate solution is diluted in sterile DPBS for use in CD8+ T cell isolation or activation processes. The bulk solution is filtered through a 0.2-μm filter and then aliquoted into single-use vials in a Class 10,000 clean room under aseptic conditions in a Class II biosafety cabinet. Aliquots are stored at −80° C. prior to use.

The anti-CD8 (37B1A) mAb was generated by fusing the splenocytes of a pathogen-free Harlan Sprague Dawley Balb/c mouse immunized with a CD8 alpha light chain peptide (AAEGLDTQRFSG; SEQ ID NO:83) with the non-secreting myeloma cell line P3X63Ag8.653 (American Type Culture Collection CRL-1580). A report from Anmed/Biosafe, Inc. indicated that cell line CRL-1580 was negative for the presence of indigenous murine viruses and Mycoplasma. Hybridomas were grown in Dulbecco's Modified Eagle Medium (DMEM) supplemented with 10% heat-inactivated Defined Fetal Bovine Serum (Hyclone SH 30070, lot AJA9530) which was negative for bacteria, fungi, viruses, and mycoplasma. The clone 37B1 was selected for its ability to produce an antibody that stained human CD8+cells (assessed by flow cytometry). This hybridoma was later subcloned by a limiting dilution technique. A subclone, 37B1A, was expanded, frozen, and stored at −140° C.

To generate purified 37B1A mAb, an aliquot of frozen cells was thawed and expanded in DMEM medium supplemented with 10% Defined Fetal Bovine Serum. The percentage of serum in the medium was progressively reduced and the cells adapted to culture in serum-free medium (Gibco-BRL 12045-076). Scale-up of the cells was achieved in a hollow fiber device (Cellmax), following the manufacturer's instructions. Growth of the cells was achieved using the same serum-free medium (Gibco-BRL 12045-076, lot 1066388) used for adaptation. Conditioned medium was collected and monoclonal antibody purified by chromatography on a Protein G Sepharose 4 Fast Flow column (Pharmacia) following the manufacturer's instructions. Cells used for scale-up were confirmed to be mycoplasma-negative when tested by PCR-ELISA method (Boehringer-Mannheim cat. No. 1 663 925). The antibody was eluted from the Protein G column with a low pH buffer (0.1 M citrate, pH 3.0) and then neutralized by adding Tris base. The protein G-purified antibody was then heat-inactivated for 30 minutes at 56° C.

High molecular weight contaminants, such as aggregated antibody, were removed by gel filtration on Sephacryl S300 High Resolution (Pharmacia) following the manufacturer's instructions. 37B1A mAb was further purified by ion-exchange chromatography on a Q Sepharose Fast Flow column (Pharmacia) following the manufacturer's instructions. After ion-exchange chromatography, purified 37B1A mAb was dialyzed against Dulbecco's Phosphate Buffer Saline (DPBS), sterilized by membrane filtration (0.2 μm filter), adjusted to a concentration of 10.0 mg/ml by adding sterile DPBS, and frozen in aliquots stored at −80° C.

Stock 37B1A hybridoma cells were tested and found negative for retroviral agents. Additionally, to ensure the absence of mycoplasma, bacteria, and endotoxin, testing is conducted on each batch of the murine anti-CD8 monoclonal antibody used in clinical preparations. Purified 37B1A mAb batches are tested for purity (SDS PAGE), sterility, endotoxin content (chromogenic LAL), mycoplasma contamination (PCR ELISA) and human CD8+ cell affinity (flow cytometry).

DYNABEADS® M-450 Sheep Anti-Mouse (SAM) IgG

DYNABEADS® M-450 (SAM) IgG are sterile paramagnetic beads coated with polyclonal sheep anti-mouse IgG that bind the primary mouse IgG. DYNABEADS®, available from Baxter Oncology Inc., are stored at 4° C. prior to use in T cell isolation using the Isolex 300i Magnetic Cell Selection System.

Recombinant Human Beta-2 Microglobulin (β2M)

Human beta-2 microglobulin (β2M) is a human plasma protein produced by recombinant DNA technology that is received as a concentrate and then diluted in sterile DPBS to achieve a concentration of 1.0 mg/mL. The bulk solution is then filtered through a 0.2-μm filter, aliquoted into sterile vials and stored at −80° C. prior to use during the preparation and peptide-loading of xAPCs and peptide loading of adherent cells.

Recombinant Human Interleukin-7 (IL-7), 30,000 U/mL (1,000× Concentration)

Recombinant Human Interleukin-7 (IL-7) is a lymphokine produced in *E. coli* and purified by the supplier (PeproTech) using high performance liquid chromatography (HPLC) but not antibody. IL-7, received as a powder, is diluted in sterile DPBS containing 1% human serum albumin. The bulk solution is then filtered through a 0.2-μm filter, aliquoted into sterile vials, and stored at −80° C. prior to use.

Recombinant Human Interleukin-2 (IL-2) (Proleukin®), 20,000 U/mL (1,000× Concentration)

Recombinant human interleukin-2 (IL-2) is a lymphokine approved for clinical use produced by recombinant DNA technology and supplied by Chiron Corporation. IL-2, received as a powder, is diluted in IL-2 diluent (0.5% human serum albumin in 50 mM acetic acid), filtered through a 0.2-μm filter, aliquoted into sterile vials, and then stored at −80° C. prior to use.

Orthoclone OKT®3 Sterile Solution, 1.0 mg/mL (OKT3)

Orthoclone OKT®3, a murine monoclonal antibody specific for the CD3 antigen of T cells supplied in ampoules as a sterile solution approved for clinical use (available from Ortho Biotech), is aliquoted into single-use vials under sterile conditions and stored frozen at −80° C. prior to use in the activation of T cells. OKT3 product information, including dosage and administration and references to methods of preparation, is given in, for example, Reinherz et al., Cell, 19(4):821-827 (1980); Chatenoud et al., J. Immunology, 137(3):830-838 (1986); and Physicians' Desk Reference, pp. 1553-1554 (1990).

25% Human Serum Albumin (HSA)

25% HAS, USP (Baxter Fenwal Laboratories; the plasma source for each lot tested to be negative for HIV-1 HIV-2, HCV, and HBV), is stored at RT prior to use as a source of buffered protein during the following T cell preparation and activation steps steps: purification of CD8+ T cells and CD8− T cells; peptide-loading of adherent cells; and final formulation of activated T cells.

Preparation of aAPCs

Cell Lines from which aAPCs Derive

Xenogenic APC lines were generated from Schneider SC2 cells (SC2 cells), which were originally established in 1969 from several hundred 20- to 24-hr old Oregon-R (wild type) *Drosophila melanogaster* (Oregon-R) embryos (American Type Culture Collection (ATCC)CRL-1963) according to published procedures (Schneider, *J. Embryol. Morph.* 27:353-365, 1972), and deposited in the ATCC (CRL10974). In order to generate xAPCs, S2 cells were transfected with vectors derived from plasmid vector pRMHa-3 (see U.S. Pat. No. 6,225,042 regarding construction and use of pRMHa plasmid vectors). One xAPC line, designated herein as clone A, was transfected with vectors encoding HLA-A2.1 Class I, B7.1 and ICAM-1. A second xAPC line, designated herein as clone B, was transfected with vectors encoding HLA-A2.1

Class I, B7.1, B7.2, ICAM-1, and LFA-3. A third xAPC cell line, designated herein as clone C, was transfected with vectors encoding HLA-A2.1 Class I, B7.1, ICAM-1, LFA-3, and CD70. Thus, clone A expresses HLA-A2, B7.1, and ICAM-1, clone B expresses HLA-A2.1 Class I, B7.1, B7.2, ICAM-1 and LFA-3, and clone C expresses HLA-A2.1 Class I, B7.1, ICAM-1, LFA-3, and CD70.B7.2 and LFA-3.

aAPC Cell Line Maintenance, Induction, and Peptide-Loading

Independent continuous cultures of clone A- and clone B-descended cells were maintained in Schneider's medium supplemented with 10% fetal calf serum and 500 µg/ml geneticin (G418), and were split twice a week with fresh media added during each split to adjust cell density to approximately $1 \times 10^6$ cells/mL. Approximately one day prior to induction (Day −2 to −4; where Day 0 is defined as the day cells are tested for expression of exogenous molecules and are loaded with peptide), 3×T75 flasks were inoculated with a volume of cell suspension maintained in stock cultures equivalent to $1.5 \times 10^7$ cells/flask. Complete Drosophila-SFM medium without G418 was added to bring the volume up to 15 ml/flask. Flasks were then incubated in a chamber at approximately 27° C. On approximately Day −1 to −3, cells were induced by addition of copper sulfate ($CuSO_4$) to a final concentration of 1.0 mM (1:200 dilution of 200 mM stock of $CuSO_4$; 75 µl of $CuSO_4$ for each T75 flask containing 15 ml of cell suspension) and returned to the 27° C. chamber. The induction time lasted for approximately 24 to 72 hours.

On Day 0, flasks containing induced cell cultures were checked visually and microscopically for evidence of contamination. Uncontaminated flasks were pooled and viable cells counted. Samples of pooled cell cultures of approximately $6 \times 10^6$ cells evaluated by flow cytometry using fluorescence assisted cell sorter (FACS) analysis to determine the level of expression of exogenous molecules. Cell cultures (approximately $1 \times 10^7$ cells/mL) were then tested to verify expression of exogenous HLA-A2.1, B7.1 and ICAM-1 (for clone A cells) or HLA-A2.1, B7.1, B7.2, ICAM-1 and LFA-3 (for clone B cells) prior to peptide loading. Once expression of exogenous molecules was verified, each cell culture was washed by splitting each culture into two sterile 50-ml conical tubes. Each tube was then filled with HYQ SFX-Insect medium and centrifuged at 1,700 rpm (600×g) for approximately seven minutes to pellet the cells. Supernatants were discarded, and the tubes containing cell pellet were again centrifuged at 1,700 rpm (600×g) for approximately one minute. Supernatants were removed with a fine-tipped pipette. Pellets from each split cell culture were then recombined and resuspended in 8 mL of SFX Insect medium to a cell density of approximately $1 \times 10^7$ cell/mL. Approximately 40 µL of a β2 microglobulin stock solution at 1.0 mg/mL and 24 µL of 1:50 dilution of a stock peptide combo solution at 1.67 mg/mL for each peptide was added to each resuspended culture. Thus, each cell culture suspension contained β2 microglobulin at a final concentration of approximately 5 µg/mL and each selected peptide to be loaded onto xAPCs at a final concentration of approximately 0.1 µg/mL per peptide. Cell cultures were incubated in the suspension containing β2 microglobulin and peptides for at least four hours and no more than eight hours, with swirling every 30 minutes at room temperature. After the peptide incubation period, approximately 1-mL aliquots of each cell culture were distributedseparately into eight polypropylene tubes (Falcon 2006). Any residual cell culture suspension was discarded.

Procedures

Example 1

Characterization of Drosophila aAPCs

Testing for Mycoplasma and Adventitious Viruses

Testing was conducted by BioReliance for mycoplasma and adventitious viral contamination. The Drosophila xAPC master cell bank was determined to be free of mycoplasma and adventitious viruses according to a standard safety-testing panel, as outlined in Table I: As used herein the term "essentially free from contamination" refers to cell cultures which are essentially free from contaminating agents including nucleic acids, bacteria, viruses and mycoplasma, particularly live bacteria, infections viruses and mycoplasma.

TABLE I

Testing of Drosophila xAPCs

| Target | Test | Specification |
|---|---|---|
| Microbial Contamination | Mycoplasma | Negative |
| Adventitious viruses | In Vitro (14 day and 42 days) Indicator cell lines: MRC-5 Vero BHK | Negative |
|  | In Vivo Adult and suckling mice Guinea pigs Embryonated hen's eggs | Negative |
| Retroviruses | Electron microscopy (TEM) | Negative |
|  | Reverse Transcriptase | Negative |

Adventitious viral contaminants were not detected when the Drosophila xAPC cell line was inoculated onto indicator cells, and the cells were observed for 14 days for cytopathic effect, hemadsorption, and hemagglutination. The incubation time of the assay was extended to a total of 42 days so that it was greater than the 31 day ex vivo culture time of $CD8^+$ effector cells during the manufacture of the cell therapy product described below. Adventitious viral contaminants were not detected in Drosophila xAPCs during this extended assay incubation duration time Co-culture of Drosophila xAPCs with insect indicator lines (Drosophila melanogaster and Aedes albopictus) resulted in the transmission of both Drosophila X and HPS-1-like viruses present in Drosophila xAPCs to the Drosophila line, but not to the mosquito line used. Both the Drosophila and mosquito lines used as indicator cells were positive for nodavirus, making it impossible to assess transmission of nodavirus from Drosophila xAPCs to the indicator cell lines used.

Testing for Retroviral-reverse Transcriptase.

Testing to confirm the absence of retroviral-reverse transcriptase (RRT) activity was performed on Drosophila xAPCs at BioReliance. The xAPC line was tested for the presence of $Mn^{++}$- and $Mg^{++}$-dependent retroviral reverse transcriptase. No evidence for the presence of these retroviral reverse transcriptases was detected.

Transmission electron microscopy (TEM) performed on Drosophila xAPCs by a service laboratory revealed the presence of viral-like particles (VLPs) in both the nucleus (20/100 cells, 40-45 nm in diameter, resembling Papovavirus) and the cytoplasm (1/100, ~30 nm resembling Nodavirus) of the cells. Subsequent TEM analysis of the *Drosophila* xAPCs at another service lab did not detect identifiable retrovirus-like particles; however, VLPs with characteristics consistent with Reovirus were observed in the cells but could not be positively identified. Due to the discrepancies in the types of viral particles identified by the two labs, testing was repeated using samples of both *Drosophila* xAPCs and the Schneider S2 (SC2) parent cell line. Cells were also sent to a third service lab. The results of this third evaluation showed that all three lines contained the same types of viral particles of two, or possibly three types:

1) 30 nm-large particles found in the nucleus in 90% of the cells with amounts ranging from <5 particles/section to very large accumulation of particles forming crystalline arrays. The particles were most consistent with a virus from the Parvovirus family, genus *Densovirus*, also known to infect insect cell lines;

2) 50 nm-large particles found exclusively in the cytoplasm. Although more difficult to detect, these particles were less frequent than the first. They were electron dense and also formed crystalline arrays in the cytoplasm. They were likely Reovirus particles replicating in the cytoplasm, and known to infect insect cell lines; and 3) 15~20 nm large electron-dense particles in the cytoplasm of some of the cells observed, believed to represent either cellular structures of accumulation of viral proteins or possibly Nodavirus-like particles.

The presence of the same VLPs in the parent line obtained from ATCC indicated that they were present prior to the establishment of the xAPC lines. TEM analysis revealed VLPs in both the nucleus and cytoplasm of *Drosophila* cell line 2. The particles were present in most sections of cells, though the number seen varied from a single particle to large aggregates, similar to the findings reported above for clones SC2 and the *Drosophila* xAPC line. Cells grew vigorously in spite of the presence of the particles, and the nature of the relationship of the particles to the cell remained unknown at that time. A summary of tests and results obtained in analysis of *Drosophila melanogaster* patent line SC2, and two *Drosophila* xAPC lines are summarized in Table II:

TABLE II

Analysis of SC2, xAPC line A, and xAPC line B

| Test | SC2 | *Drosophila* xAPC line A | *Drosophila* xAPC line A |
|---|---|---|---|
| Mycoplasma | ND[1] | Negative | Negative |
| TEM[2] | Positive for VLPs[3] | Positive for VLPs | Positive for VLPs |
| RRT activity[4] | ND | ND | Negative |
| Viral contaminants (in vitro)[5] 14 day assay | ND | Negative | Negative |
| Viral contaminants (in vitro)[5] 42 day assay | ND | Negative | ND |
| Viral contaminants (in vivo)[6] | ND | ND | Negative |

[1]not determined
[2]Transmission electron microscopy
[3]Viral-like particles (identified as Densovirus and Reovirus by structure, size and location)
[4]Retroviral Reverse Transcriptase Activity
[5]Assay to detect adventitious viral contaminants when test articles inoculated onto indicator cell lines
[6]Assay to detect viruses, which do not cause a discernable effect in cell culture systems

*Drosophila* xAPC line A was chosen for further characterization and use as a xAPC in the remainder of the examples. Accordingly, the *Drosophila* xAPC line A is referred to below as *Drosophila* xAPC, or xAPC, below.

Isolation and Characterization of Viral-like Particles from *Drosophila* xAPC line A.

VLPs were pelleted from *Drosophila* xAPC lysate, and purified by equilibrium centrifugation in CsCl density gradients. VLPs banded at densities of 1.30 g/mL, 1.36 g/mL, and 1.41 g/mL. Purified particles were analyzed by electron microscopy, SDS/PAGE, nucleic acid extraction and sequencing. Negative staining of these fractions followed by transmission electron microscopy led to the observation of three types of particles in those fractions:

1) The fraction at density 1.41 consisted of non-enveloped, icosahedral particles of about 42 nm in diameter. Those particles were consistent with the particles observed in the nucleus of the cells and believed to be *densovirus*-like;

2) The fraction at density 1.36 consisted of non-enveloped particles of about 30 nm in diameter, and confirmed the structures observed in the cytoplasm of some cells were not the result of the accumulation of viral proteins, but rather the accumulation of particles, most likely from the Nodaviridae family; and 3) The fraction at density 1.30 consisted of non-enveloped, icosahedral particles of about 42 nm in diameter identical to the particles at density 1.41. In addition, a few icosahedral particles of larger size (60 nm) were found in this fraction and were consistent with the particles observed in the cytoplasm of the cells and believed to be reovirus-like.

The results of VLP analysis are summarized in Table III:

TABLE III

Characterization of Viral Particles Purified from *Drosophila* xAPC

| Density (g/mL) | Virus Candidate | Size | Proteins | Nucleic Acid | DNA Sequence Analysis |
|---|---|---|---|---|---|
| 1.41 | HPS-1 like | 42 nm | ~100 kD | dsRNA (6 kb) | 28% homologous to RNA dependent RNA polymerase |
| 1.36 | *Drosophila Nodaviridae* | 30 nm | 43 kD | ssRNA (3.0 kb + 1.2 kb) | 88% homologous to FHV[1], BBV[2] & BV[3] |

TABLE III-continued

Characterization of Viral Particles Purified from *Drosophila* xAPC

| Density (g/mL) | Virus Candidate | Size | Proteins | Nucleic Acid | DNA Sequence Analysis |
|---|---|---|---|---|---|
| 1.30[4] | Empty HPS-1 like | 42 nm | ~100 kD | No nucleic | N/A |
| | *Drosophila* X virus | 60 nm | | acid | ND |

[1]FHV = Flock House Virus (Insect Nodavirus)
[2]BB = Black Beetle Virus (Insect Nodavirus)
[3]BV = Boolarra virus (Insect Nodavirus)
[4]Two types of particles identified; 60 nm particles represent 1:100 of the purified preparation
ND = not determined;
N/A = not applicable Density 1.41 Particles Based on the analysis of proteins and nucleic acid, density 1.41 particles did not appear to belong to the Densoviridae genus, which is characterized by dsDNA between 4 and 6 kb and at least three structural proteins in the range of 40-90 kd. N-terminal sequencing of the 100 kd polypeptide was performed and the amino-acid sequence used to clone the homologous N-terminus sequence of the viral genome. Sequence analysis showed this protein to novel, with 28% homology with viral RNA-dependent RNA polymerase. Mass spectrophotometry (MALDI-MS) analysis confirmed the novelty of this protein as well. Tryptic digest and Edman sequencing of peptides purified from the 100 kd protein confirmed the nucleic acid data. Based on RNase and DNase analysis of the purified viral nucleic acid it was confirmed that the genome was in fact dsRNA and not dsDNA, thereby eliminating *Densovirus* as one of the three insect viruses. These observations were most consistent with the HPS-1 virus of *Drosophila* SC2 cells described by Scott et al (see, e.g., Scott et al., *Cell*, Vol. 33(3), pp. 929-941 (1980)). This virus was described as 36-nm diameter non-enveloped virions present mainly in the nucleus of infected cells. Purified particles were found at density 1.41 and contained a single segment of dsRNA of about 6 kb in length, associated with a major protein (120 kd) believed to be the viral coat protein, along with a minor protein (200 kd).

A real-time quantitative RT/PCR assay was developed to detect the presence of HPS-1-like virus in cells. The procedure results in the amplification of a virus specific sequence of 241 bases in length. Spiking experiments of HPS-1-like specific viral template into cDNA prepared from CD8+ cells confirmed the sensitivity of virus detection to be between 10-100 copies per μg of DNA Density 1.36 Particles Analysis of the proteins and nucleic acid from purified density 1.36 particles confirmed this virus to be from the Nodaviridae genus. The DNA sequence representing RNA1 (3.0 kb) was completed and found to be approximately 90% homologous to Flock House virus, an insect virus of the Nodaviridae family. Full-length cloning and sequencing of the RNA2 segment was also completed and the N-terminal amino acid sequence of the 43-kd coat protein was homologous with both the *Drosophila* Nodaviridae Virus (DrNV) isolated coat protein DNA and Flock House virus, as indicated below:

```
DrNV DNA:        MVNNIKPRRQRSQRV     (SEQ ID NO: 80)
43 kd Protein:   VNNIKPKRQRPQ-V      (SEQ ID NO: 81)
Flock Virus DNA: MVNNIKPRRQRAQRV     (SEQ ID NO: 82)
```

A real-time quantitative RT/PCR assay was developed to detect the presence of *Drosophila* Nodaviridae virus in cells. The procedure results in the amplification of a virus specific sequence of 1.33 bases in length. Spiking experiments of Nodaviridae specific viral template into cDNA prepared from CD8+ cells confirmed the sensitivity of virus detection to be between 10-100 copies per μg of DNA.

Density 1.30 Particles

Nucleic acid extraction from the particles at density 1.30 failed to yield either DNA or RNA. The SDS/page profile of this preparation was identical to the one obtained for the preparation at density 1.41. Together with the electron microscopy observations, these results suggested this preparation was comprised mainly of empty HPS-1 viral particles, with some bigger particles (60 nm) in insufficient numbers to be further characterized.

A number of viruses from the *Reoviridae* genus, with characteristics compatible with this third virus (localization, formation of crystalline arrays, and size) have been reported to infect insect cells, including *Drosophila* (see, e.g., Haars et al., *Virology*, Vol. 101(1), pp. 124-130 (1980)). A large number of PCR primers were generated, based on sequences conserved among insect Reoviruses, and used to screen cDNA prepared from *Drosophila* xAPCs. No Reovirus sequence was amplified from cDNA prepared from these cells.

*Drosophila* X Virus (DXV) is a dsRNA virus of the Birnaviridae family and known to infect some *Drosophila* cell lines (see, e.g., Shwed et al., *Virology*, Vol. 296(2), pp. 241-250 (2002)). The 60-nm virion has a buoyant density of 1.34, with empty capsids that sediment at a density of 1.29. The genome consists of two segments, segment A (3360 bp) and segment B (3100 bp). A set of PCR primers specific for DXV was designed and used to probe for the presence of DXV in *Drosophila* xAPCs. A PCR-amplified band of expected molecular weight was obtained and the amplified fragment (682 bp) sequence was identical to published DXV sequence.

In addition, some DXV sequences were cloned from the purified fraction of density 1.36, along with a majority of Nodaviridae sequences. These results are consistent with the published literature, describing infectious particles at buoyant densities at 1.33-1.34, with empty particles at 1.29. Consequently, the 60-nm particles observed by TEM in the density 1.30 fraction were not *Reoviridae* as believed based on size and shape, but empty DXV particles. This explained the inability to extract DNA or RNA from these VLPs.

A real-time quantitative RT/PCR assay was developed to detect the presence of *Drosophila* X virus in cells. The procedure results in the amplification of a virus specific sequence originating from the virus polyprotein of 178 bases in length. Spiking experiments of DXV-specific viral template into cDNA prepared from CD8+ cells confirmed the sensitivity of virus detection to be between 10-100 copies per μg of DNA.

Example 2

Inactivation of xAPCs

Glutaraldehyde Fixation

Inactivation of *Drosophila* cells was initially attempted with glutaraldehyde fixation in the absence of preservative. *Drosophila* xAPCs fixed with 0.3% glutaraldehyde were capable of antigen-specific proliferation of $CD8^+$ T cells (2.5- to 6-fold less than unfixed cells), $CD8^+$ T cell activation (2-fold less than unfixed cells), and generation of $CD8^+$ T cells capable of lysing target cells (to a lesser degree than unfixed cells). Thus, this inactivation method was found to result in *Drosophila* xAPCs that had diminished APC function relative to cells not inactivated by the glutaraldehyde fixation protocol.

Freeze-Thaw Cycling

In a second attempt to inactivate the *Drosophila* xAPCs without diminishing xAPC function, a series of freeze-thaw cycles were performed. The freeze-cycles entailed placing the xAPCs in either liquid nitrogen or dry ice (solid $CO_2$) until xAPCs were completely frozen (e.g. for about one minute), and then removing xAPCs form the liquid nitrogen or dry ice and allowing the xAPCs to come to room temperature. The freeze-thaw cycles were performed with xAPCs in media that was devoid of the preservative, dimethyl sulfoxide (DMSO). This method resulted in 100% non-viable (i.e., dead) cells after two freeze-thaw cycles as assessed by trypan blue staining. These non-viable cells were capable of stimulating of $CD8^+$ T cells, generating CTLs with antigen-specific cytolytic activity comparable to the cytolyic activity observed with $CD8^+$ T cells that were stimulated with *Drosophila* xAPCs that were not subjected to a freeze-thaw cycle. Additionally, the freeze-thaw studies demonstrated that *Drosophila* xAPCs may be induced, peptide-loaded, and freeze-thawed, and then subsequently used to stimulate naïve T cells; thus, the *Drosophila* xAPCs need not be continuously carried in culture in order to preserve xAPC function.

Psoralen/UVA Treatment

The freeze-thaw method demonstrated that *Drosophila* xAPCs rendered substantially non-viable retained the ability to activate naïve T cells. However, a concern remained that xenogenic nucleic acid associated with the xAPCs may retain some activity or some degree of bacterial or viral contamination after the freeze-thaw cycling. Desiring to inactivate xenogenic nucleic acid associated with xAPCs to yield a highly functional antigen-presenting system essentially free of DNA, RNA, bacterial, or viral contaminants, an inactivation regimen involving exposing the xAPCs to a member of the psoralen family of molecules followed by exposure to long-wave ultraviolet radiation (UVA) was tested. Several studies were performed using various psoralen family members, including: psoralen (7-H-furo[3,2-g]-benzopyran-7-one, available from Sigma) and a clinical grade of the psoralen derivative 9-methoxy-7H-furo[3,2-g]-1-benzopyran-7-one (also known as methoxsalen, 8-methoxypsoralen (8-MOP) and marketed under the trademark name UVADEX™).

A baculovirus/Sf9 infectivity assay was used to determine if psoralen-derivative/UVA treatment was sufficient to inactivate viruses associated with virus-infected insect cells. Sf9 insect cells were infected with BacPAK6 viral stock and incubated at room temperature for one hour (BacPAK6 baculovirus rapid titer kit; BD Biosciences Clontech). Infected cells were either untreated or treated with (5 µg/ml) UVADEX™ and irradiated with long-wave ultraviolet radiation (320 nm-380 nm, UVA) from a light source above the container and a light source below the container for approximately 5 minutes (10-15 $mW/cm^2$). Five days after irradiation, culture supernatants were collected. From these, new viral stocks were prepared via serial dilutions of $10^{-3}$, $10^{-4}$ and $10^{-5}$, respectively. These serially diluted stock dilutions were each used to infect a second set of fresh (i.e., not previously infected) Sf9 cell cultures. This second set of cultures was overlaid with methylcellulose and grown for approximately 48 hours. Culture supernatants of this second set of cultures were discarded and a mouse monoclonal anti-gp64 (baculovirus-specific) protein antibody (Invitrogen) was added. After an inbubation period and several washes to remove unbound anti-gp64 antibody, a goat-anti-mouse polyclonal antibody conjugated to horseradish peroxidase (i.e., secondary antibody obtained from Invitrogen) was added. Unbound secondary antibody was removed with several washes, and peroxidase was added. The number of stained foci was counted and the virus titer (pfu/ml) was calculated according to the manufacturer's instructions.

As shown in Table W below, a five-minute UVA (350-400 nm) irradiation time period was sufficient to prevent baculovirus replication in the Sf9 indicator cell cultures, whereas the control, untreated cells contained a viral titer of $8 \times 10^8$ plaque forming units (PFU)/ml of baculovirus.

TABLE IV

UVADEX ™/UVA treatment inhibition of virus replication in baculovirus infected Sf9 cells

| UVA Irradiation Time | Virus added | Virus Titer ($10^{-4}$) | | | Virus Titer ($10^{-5}$) | | |
|---|---|---|---|---|---|---|---|
| 0 minutes | − | 0 | 0 | 0 | 0 | 0 | 0 |
| 0 minutes | + | >500 | >500 | >500 | 232 | 210 | 198 |
| 5 minutes | + | 0 | 0 | 0 | 0 | 0 | 0 |
| 10 minutes | + | 0 | 0 | 0 | 0 | 0 | 0 |

In a similar experiment, Sf9 cells were infected with the titrated doses of baculovirus as described above. The infected cells were then treated with 5 µg/ml of UVADEX™ at 4° C. for 30 min followed by UVA irradiation for 0 minutes, 2 minutes, 10 minutes or 20 minutes, respectively. The treated cells were then cultured at 28° C. for four days. The culture supernatant was collected and used to infect a new culture of Sf9 cells seeded in 96-well plates. Baculovirus in the Sf9 cells was detected by a rapid microtiter assay (Invitrogen). The culture plates were overlaid with methylcellulose and cultured for 48 hrs. Baculovirus was detected by immunoassay with a gp64-specific antibody (Invitrogen). The number of foci in each well was counted and the virus titer (pfu/ml) of the supernatant of the infected cells was calculated according to the manufacturer's instructions. The results, presented in FIG. 1, demonstrate that UVADEX™ treatment followed by a two-minute exposure to UVA diminished the baculovirus titer of the collected culture supernatant to less than 10% of the baculovirus titer seen in untreated/exposed cells. UVADEX treatment followed by ten and twenty-minute UVA exposure times, respectively, resulted in no detectible baculovirus titer.

In order to determine whether psoralen/UVA treatment might inhibit the proliferation of xAPCs, *Drosophila* clone B xAPCs were either untreated or treated with 5 µg/ml UVADEX™ at 4° C. for 30 minutes followed by UVA treatment for 0, 2, 10, or 20 minutes. Treated xAPCs were washed completely to remove residual UVADEX and then both untreated and treated xAPCs were seeded in 6-well plates at $1 \times 10^6$ cells/ml and continuously cultured for 16 days. Viable (i.e., live) xAPCs were counted on day 1, day 5, day 9, day 14, and day 16 post-treatment by trypan blue staining of each culture.

Figure 2:
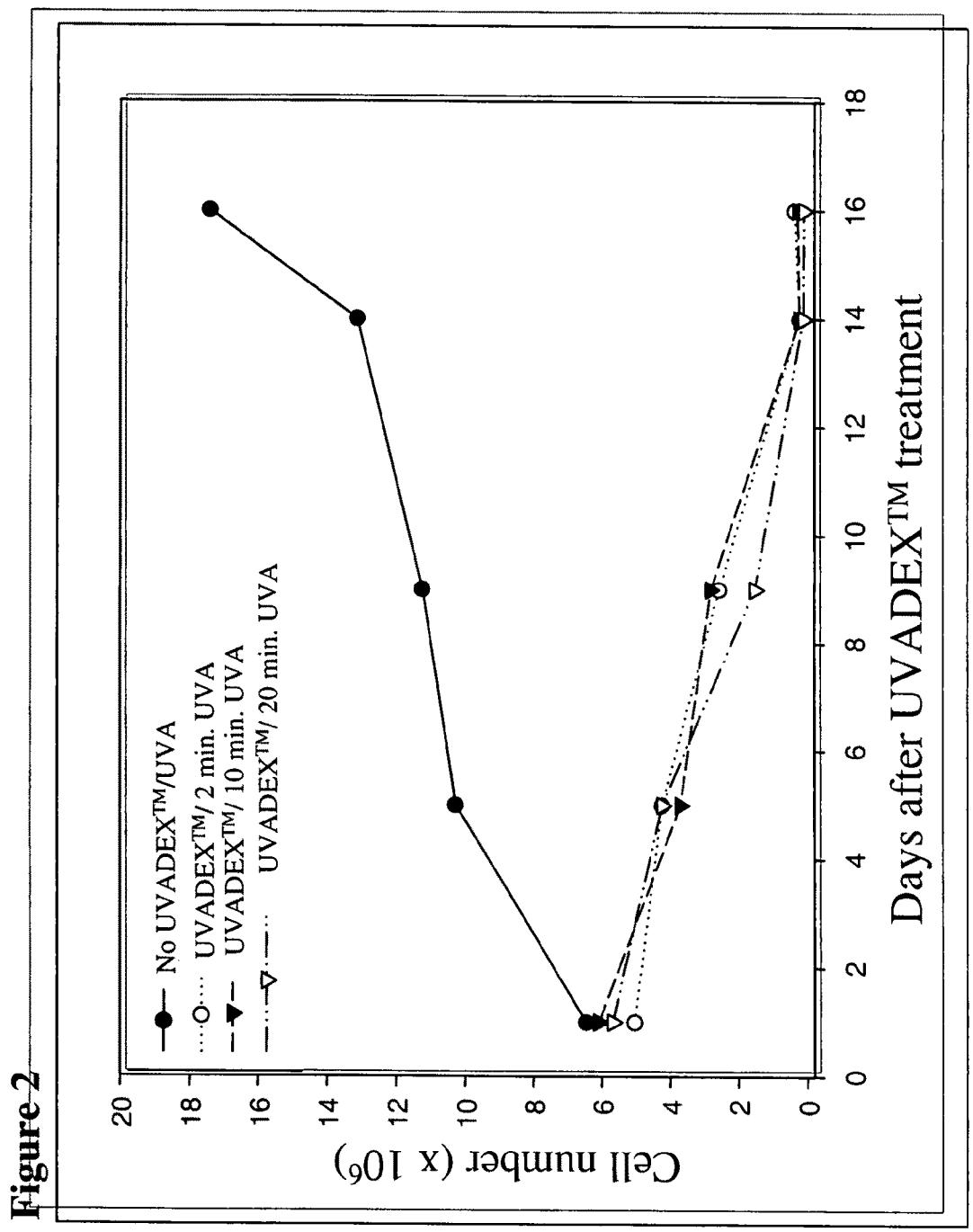
FIG. 2 illustrates an analysis of cell proliferation of untreated xenogenic APCs (xAPCs) versus UVADEX/UVA-treated *Drosophila* xAPCs. *Drosophila* xAPCs were either untreated or treated with UVADEX (5 µg/ml) at 4° C. for 30 minutes, followed by UVA treatment for 0, 2, 10, or 20 minutes, respectively, as indicated. The treated cells were washed completely to remove residual UVADEX and then seeded in 6-well plate at 1×10$^6$ cells/ml and continuously cultured for 16 days. Viable (i.e., live) xAPCs were counted on day 1, day 5, day 9, day 14, and day 16 post-treatment by trypan blue staining of each culture.

As shown in FIG. 2, *Drosophila* xAPC proliferation was effectively inhibited by every UVA exposure time duration tested, with approximately 50% inhibition of viability of all UVADEX/UVA-treated cultures at about nine days post UVADEX/UVA treatment. Furthermore, by two weeks after UVADEX/UVA treatment almost no viable cells were detected in any treated culture. Conversely, non-UVADEX/UVA-treated xAPCs displayed robust viability, almost tripling cell count within fourteen days in culture. Therefore, it was concluded that UVADEX/UVA treatment effectively attenuated xAPC proliferation, even at the lowest UVA time duration tested (2 minutes).

It was possible that xenogenic nucleic acid introduced into the xAPCs might have remained active, even though the xAPCs themselves were rendered nonproliferative. In order to determine whether psoralen/UVA treatment inactivates xenogenic nucleic acid introduced into xAPCs, an analysis of xenogenic nucleic acid transcription of *Drosophila* clone B xAPCs after either γ-irradiation or UVADEX/UVA treatment was performed. *Drosophila* clone B xAPCs were either untreated, treated with UVADEX™ (5 μg/ml)/UVA, or were treated with γ-radiation for 50 min (delivering approximately 16,000 rads). Each culture of xAPCs was washed and cocultured for 10 weeks with an indicator *Drosophila* cell line designated herein as clone D, which is a cell line that has not been modified by introduction of xenogenic nucleic acid. Reverse transcriptase (RT)-PCR reactions using primers specific for xenogenic HLA A2.1, B7-1, B7-2, and β2m transcripts were then performed on extracts of the cocultures. The results, depicted in FIG. 3, show that both the untreated and the γ-radiation-treated xAPCs contained active xenogenic nucleic acid, as evidenced by the detection of xenogenic HLA A2.1, B7-1, B7-2, and β2m transcripts (lanes 2 and three, respectively). Conversely, none of the xAPCs treated with UVADEX™ (5 μg/ml) and UVA, regardless of UVA treatment duration, contained active xenogenic nucleic acid, as evidenced by the absence of detectable levels of xenogenic HLA A2.1, B7-1, B7-2, and β2m transcripts. Therefore, it was concluded that UVADEX (5 μg/ml)/UVA treatment of xAPCs inactivated the xenogenic nucleic acid that was introduced into the xAPCs.

Figure 4B:
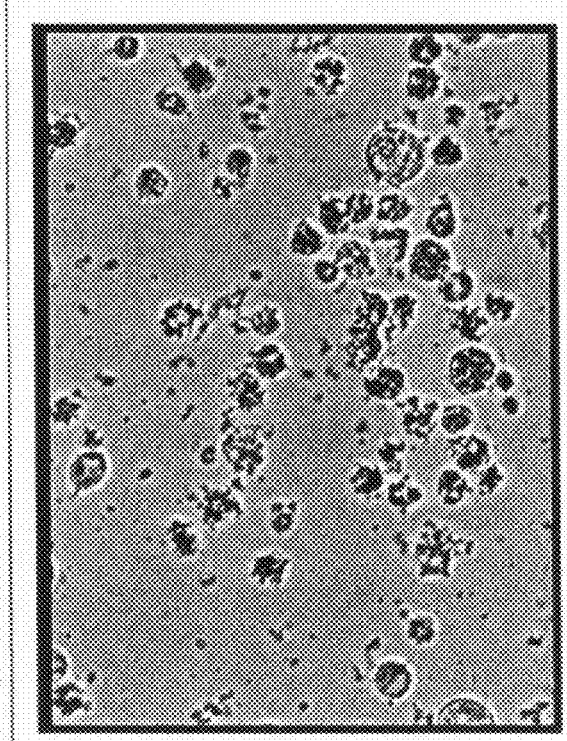
FIGS. 4A through 4C show an analysis of infectivity of lytic virus and microbial activity associated with *Drosophila* xAPCs and associated xenogenic nucleic acid that were untreated or were subjected to UVADEX/UVA treatment.

As certain adventitious cytolytic viruses, mycoplasmas, and other microbial organisms may be associated with the xAPCs in addition to the xenogenic nucleic acid introduced into the xAPCs, it was desirable to determine if the UVADEX/UVA treatment regimen inactivated these potential contaminants of the xAPCs. Thus, a xAPC culture containing approximately $6 \times 10^8$ *Drosophila* xAPCs (clone B) was collected, suspended in 0.6 ml Schneider's media on ice, and sonicated for 30 seconds. Cell debris was pelleted by centrifugation, and the supernatant collected and layered onto a cesium chloride (CsCl) cushion, which was at a density of 1.2 (20% w/w CsCl), at a ratio of three volumes of supernatant to one volume of CsCl. The supernatant-loaded CsCl cushion was then ultracentrifuged at 25,000 rpm for four hours. Viral fractions were collected and the fraction densities measured. Three milliliter fractions at a density of 1.0 to 1.2 were pooled and dialyzed against phosphate-buffered saline (PBS), generating a viral stock, and the viral stock stored at −80° C. until use. An aliquot of the virus stock, equivalent to lysate from approximately $1 \times 10^8$ xAPCs, was subjected to UVADEX™/UVA treatment (5 μg/ml for 10 minutes) or was untreated. Independent cultures ($1 \times 10^6$ cells/culture) of the *Drosophila* clone D indicator cell line were incubated at 28° C. with either the treated and untreated viral aliquots. After a three-day incubation period, the indicator cell cultures were harvested and stained with propidium iodide (PI) (1 μg/$1 \times 10^6$ cells) at 4° C. for 10 minutes. The live and lytic cells were analyzed by FACS, with the results depicted in FIGS. 4A-4C.

Figure 4A:
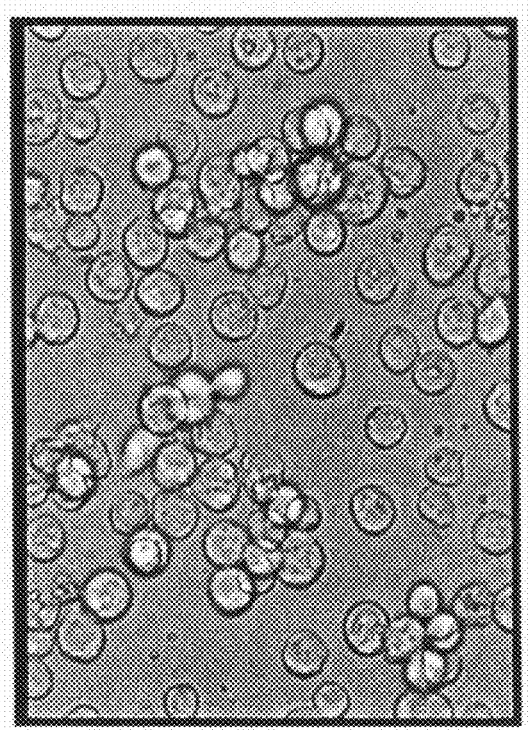

The untreated virus stock aliquot isolated from the xAPCs infected the indicator cell line, equivalent to approximately $1 \times 10^8$ plaque forming units (pfu), resulted in lysis of essentially all of the cells in the indicator cell line culture as observed by microscopy of culture samples (image of representative microscopic field, FIG. 4A). Conversely, the virus stock aliquot isolated from the xAPCs that was subjected to UVADEX™/UVA (5 μg/ml for 10 minutes) failed to result in any observable indicator cell infection or lysis (image of representative microscopic field, FIG. 4B).

Figure 4C:
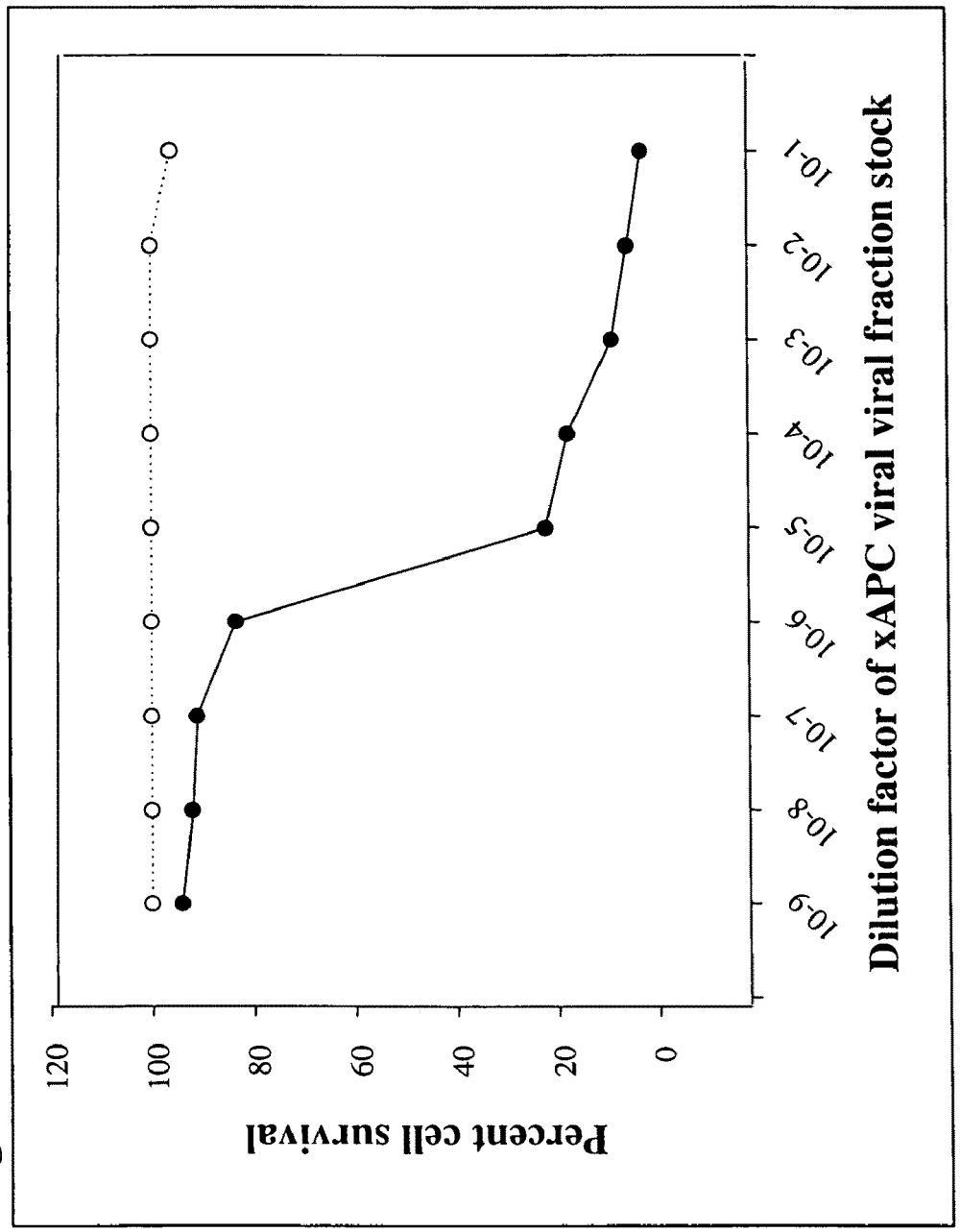

In a similar experiment, a set of serial dilutions of the xAPC viral stock consisting of $10^{-1}$, $10^{-2}$, $10^{-3}$, $10^{-4}$, $10^{-5}$, $10^{-6}$, $10^{-7}$, $10^{-8}$, and $10^{-9}$ dilutions were either untreated or treated with UVADEX/UVA (5 μg/ml for 10 minutes) prior to being incubated with *Drosophila* clone D indicator cell cultures. After a three-day incubation period, the percentage of viable cells was quantified in each indicator cell line culture. The results, reflected in FIG. 4C, show that the treated viral fraction was almost completely incapable of infecting and lysing the indicator cell culture at all but the lowest dilution tested. However, the untreated viral fraction was capable of effecting lysis of approximately 80% of the indicator cell culture at the $10^{-5}$ viral fraction dilution.

In order to confirm that xenogenic nucleic acid associated with the UVADEX™/UVA treated xAPCs was not transiently infective towards, and was not transiently expressed in, the clone D indicator cells, fluorescence-activated cell sorter (FACS) analysis of *Drosophila* xAPCs clone B/clone D cocultures was performed. For comparison, γ-radiation-treated xAPC clone B/clone D cocultures and untreated xAPC clone B/clone D cocultures were analyzed by FACS as well.

Figure 5:
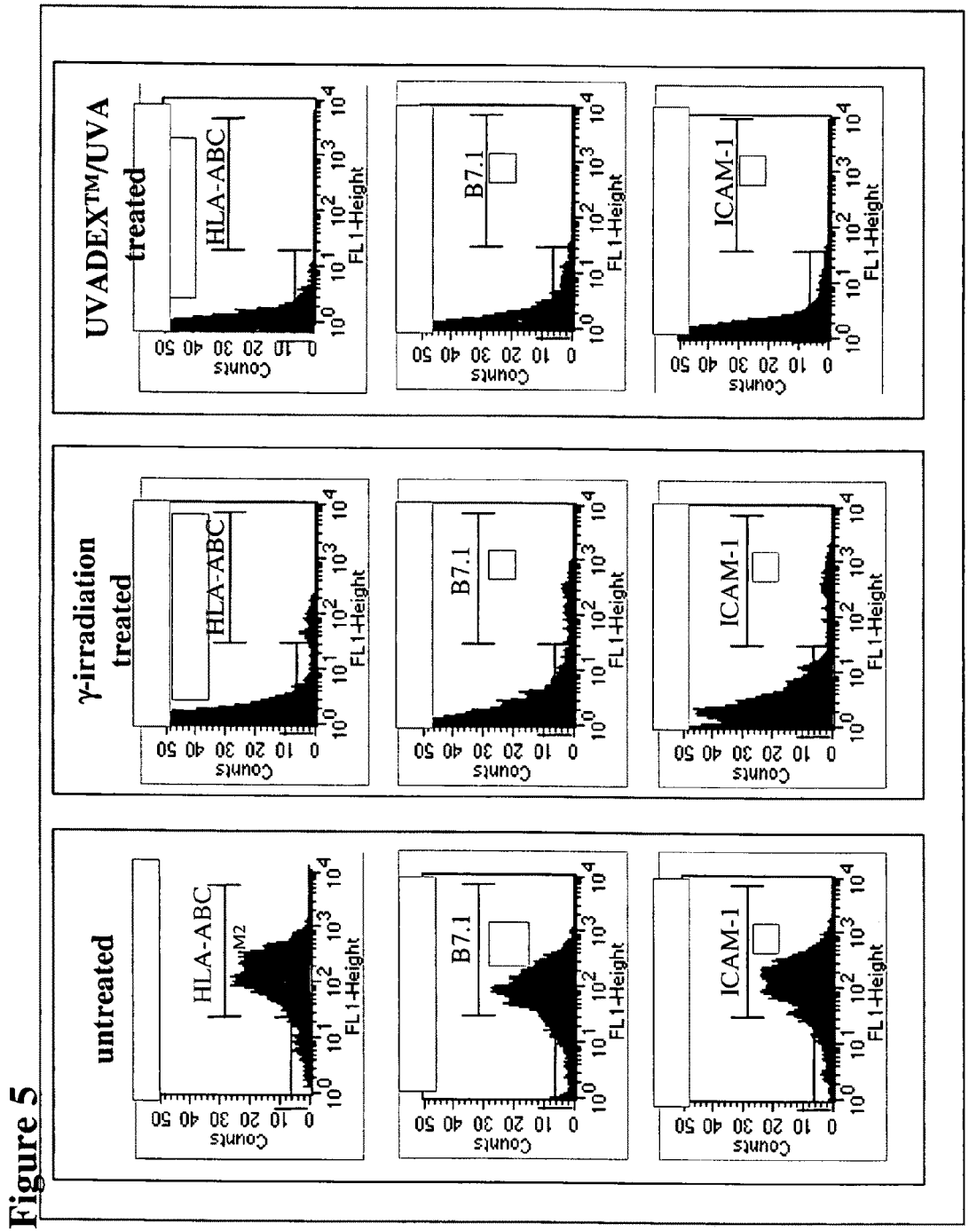
FIG. 5 shows a FACS analysis of surface expression of exogenous molecules on cells from *Drosophila* xAPC/*Drosophila* clone D indicator cocultures, which were either untreated, treated with γ-irradiation-treated, or UVADEX/UVA-treated. FACS analysis was carried out by independently using antibodies specific for human HLA, human B7.1, and ICAM-1, as indicated.

*Drosophila* xAPCs cultures (clone B) were untreated, treated with UVADEX/UVA (5 μg/ml), or γ-radiation-treated for 50 minutes (delivering approximately 16,000 rads). The cells from each culture were washed and then and cocultured with clone D indicator cells for 10 weeks. The cocultured cells were collected and aliquoted, and each aliquot was stained with one of HLA-A2, B7-1, and ICAM-1 fluorescein isothiocyanate (FITC)-conjugated monoclonal antibodies (mAbs), respectively. The stained cocultures were then analyzed by FACS. As shown in FIG. 5, cocultures containing untreated xAPCs expressed HLA-A2, B7-1, and ICAM-1; cocultures containing γ-radiation-treated xAPCs displayed modest, but significant, expression of HLA-A2, B7-1, and ICAM-1; and cocultures containing UVADEX™/UVA-treated xAPCs displayed undetectable levels of HLA-A2, B7-1, and ICAM-1.

Figure 6:
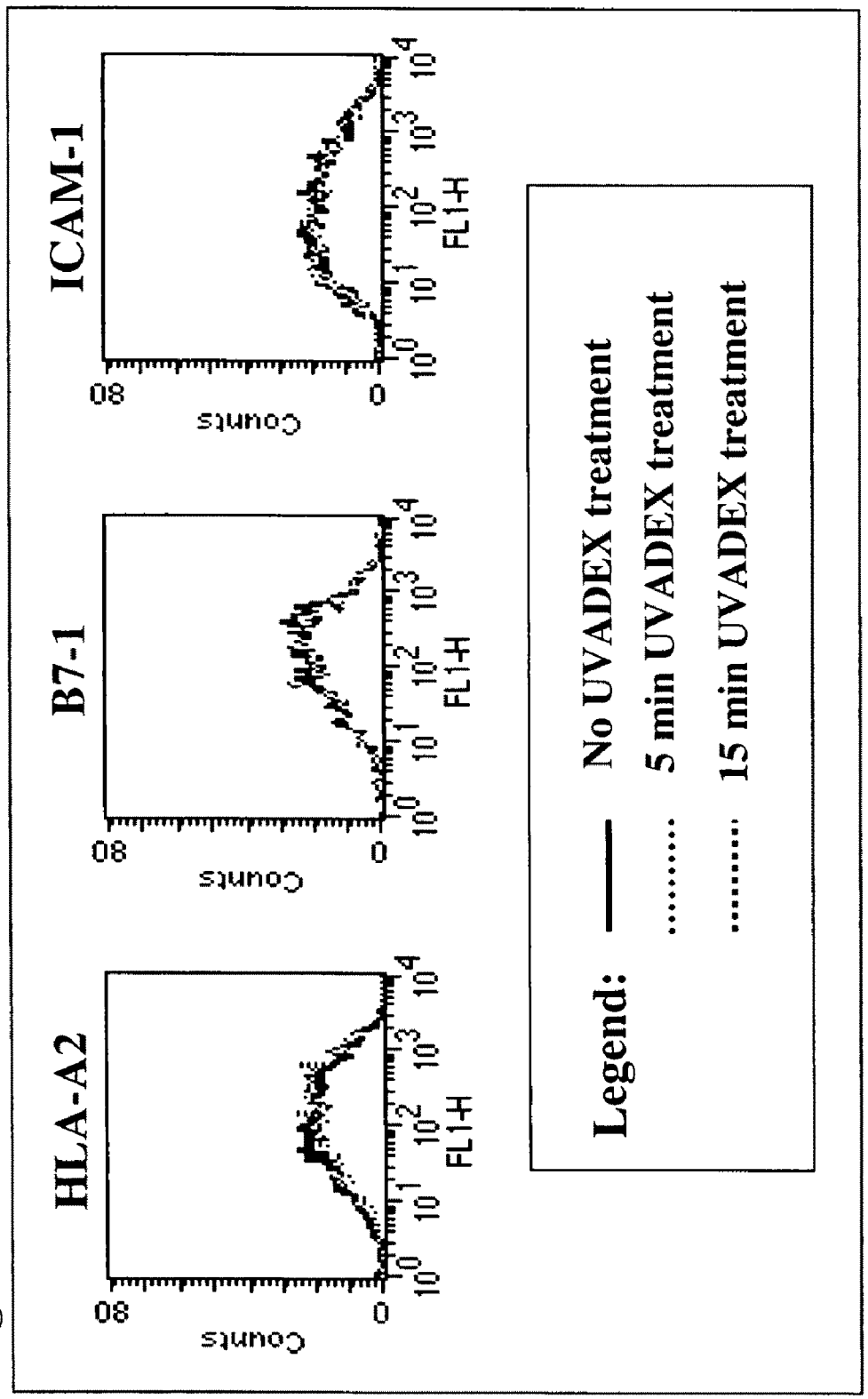
FIG. 6 shows a FACS analysis of surface expression of exogenous molecules on untreated and UVADEX-treated *Drosophila* xAPCs that were exposed to 5 or 15 minutes of UVA, as indicated. FACS analysis was carried out by independently using antibodies specific for human HLA, human B7.1, and ICAM-1, as indicated.

In a similar experiment, *Drosophila* xAPC cultures were induced to express exogenous molecules encoded by recombinant vectors, and then incubated with UVADEX™ (5 μg/ml) and treated with UVA for 0, 5 or 15 minutes. The xAPC cultures were washed and stained with monoclonal antibodies specific for HLA-A2, B7-1, or ICAM-1 and analyzed by FACS. As shown in FIG. 6, the surface expression level of each of the three exogenous molecules was essentially the same for all UVA time durations tested.

Collectively, these results demonstrated that *Drosophila* xAPCs that are inactivated by psoralen/UVA treatment were rendered essentially nonviable and essentially noninfectious. Additionally, xAPCs induced to express exogenous nucleic acid such that the encoded proteins were expressed on the xAPC cell surface prior to psoralen/UVA-mediated inactivation, retained pre-inactivation expression levels of the exogenous proteins subsequent to the inactivation.

Selected Peptide-Specific Expansion and Activation of Naïve T Cells Upon Incubation with Inactivated *Drosophila* xAPCs Naïve CD8+ T cells were purified from the peripheral blood mononuclear leukocytes (PBMC) of HLA-A2-positive donors and cultured at 37° C. with UVADEX™/UVA-treated xAPCs or UVADEX™/UVA plus freeze-thaw-treated xAPCs in the presence of 10 µg/ml of a MART-1 peptide corresponding to amino acids 27-35 of human MART-1 (AA-GIGILTV; SEQ ID NO:9). Human recombinant (r) IL-2 (20 units/ml) and rIL-7 (30 units/ml) were each added after the fifth day of the culture period. The CD8+ T cells were restimulated twice on the seventh and fifteenth days of the culture period with non-CD8 adherent cells in PBMC from the same donor in the presence of the MART-1 peptides. The expanded CD8+ T cells were counted after 21 days of culture by tryptan-blue staining. The results, summarized in Table V below, show that when xAPCs are untreated, UVADEX™/UVA-treated, or UVADEX™/UVA plus freeze-thaw-treated, the stimulated CD8+ T cells proliferate (i.e., expand) at similar rates.

TABLE V

Number of CD8+ T cells after culture with peptide-loaded xAPCs

| Experiment (day 21) | No treatment (CD8+ × 10⁶) | UVADEX/UVA (CD8+ × 10⁶) | UVADEX/UVA + Frozen (CD8+ × 10⁶) |
|---|---|---|---|
| Donor 1 | 38.20 | 42.60 | 52.90 |
| Donor 2 | 11.96 | 9.94 | 13.44 |
| Donor 3 | 26.04 | 24.24 | 35.04 |
| Donor 4 | 16.74 | 15.66 | 17.80 |

Naïve CD8+ T cells were purified from the PBMC of HLA-A2 positive donors and cultured with UVADEX™/UVA-treated xAPCs or freeze-thawed and UVADEX™/UVA-treated xAPCs at 37° C. in the presence of 10 µg/ml of a MART-1 peptide (amino acid sequence AAGIGILTV (SEQ ID NO;9)). Human rIL-2 (20 units/ml) and rIL-7 (30 units/ml) were each added to the culture at day 5. The CD8+ T cells were restimulated twice on the seventh and fifteenth days of the culture period with non-CD8 adherent cells in PBMC from the same donor in the presence of the MART-1 peptides. The expanded CD8+ T cells were then stained with MART-1 tetramers (Beckman Coulter) consisting of four MHC molecules bound to the MART-1 peptide, which was conjugated to a fluorescent protein, and analyzed by FACS. The results, summarized in Table V below, show that incubation of naïve CD8+ T cells with treated xAPCs resulted in a greater percentage of peptide/MHC tetramer (pMHC)-positive CTLs derived from all of the donors tested. Furthermore, incubation of naïve CD8+ T cells with UVADEX/UVA plus freeze-thaw-treated xAPCs resulted in a greater percentage of pMHC tetramer-positive CTLs than UVADEX/UVA-treated xAPCs alone in three out of the four donors (donors 1, 2, and 3).

TABLE VI

Percent p/MHC tetramers of CD8+ T cells after culture with peptide-loaded xAPCs

| Experiment | No treatment (% Tetr + CD8+) | UVADEX ™ (% Tetr + CD8+) | UVADEX ™/ Frozen (% Tetr + CD8+) |
|---|---|---|---|
| Donor 1 | 0.81 | 0.95 | 1.52 |
| Donor 2 | 9.94 | 11.55 | 14.50 |
| Donor 3 | 8.71 | 15.07 | 21.35 |
| Donor 4 | 20.06 | 43.33 | 21.88 |

To further investigate the extent to which the inactivated xAPCs, when loaded with selected peptide, activate naïve T cells to become CTLs, naïve CD8+ T cells were purified from peripheral blood mononuclear cells (PBMC) of HLA-A2 positive donors and cultured at 37° C. with untreated *Drosophila* xAPCs, UVADEXIUVA-treated *Drosophila* xAPCs, or UVADEX/UVA plus freeze-thaw-treated *Drosophila* xAPCs in the presence of 10 µg/ml of a MART-1 peptide corresponding to amino acids 27-35 of the human MART-1 protein, AAGIGILTV (SEQ ID NO:9). Human recombinant interleukin (rIL)-2 (20 units/ml) and rIL-7 (30 units/ml) were added to each of the cultures on the fifth day of the culture period. The CD8+ T cells were restimulated twice a day on the seventh and fifteenth days of the culture period with non-CD8 adherent cells from PBMC of the same donor in the presence of the MART-1 peptide (SEQ ID NO:9). The cultured CD8+ T cells were collected on the 21ˢᵗ day of the culture period, and CTL activity was measured by standard $^{51}$Cr release assay, which provides a direct measure of specific cell killing (i.e., cytolytic activity).

Figure 7:
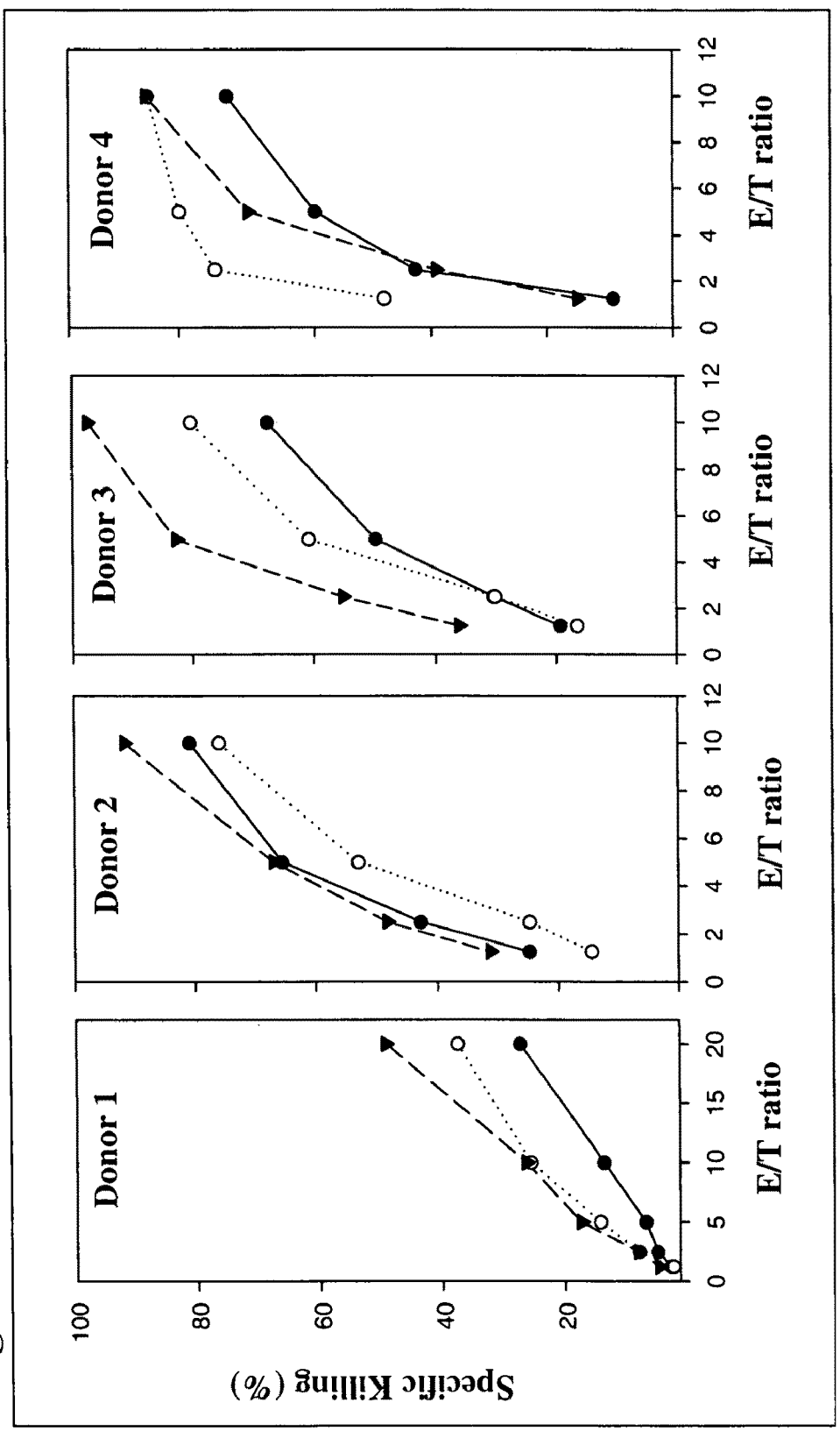
FIG. 7 shows the generation of MART-1 specific CTLs with untreated, UVADEX/UVA-treated, or UVADEX/UVA plus freeze-thaw treated xAPCs. Solid circles, not treated; open circles, UVADEX/UVA; closed triangles, UVADEX/UVA plus freeze-thaw treated.

The results, depicted in FIG. 7, show that CTLs from three of the four donors (Donors 1, 3, and 4) exhibited greater % specific killing when activated by either UVADEX/UVA-treated xAPCs or UVADEX/UVA plus freeze-thaw-treated xAPCs, relative to CTLs activated by nontreated xAPCs. CTLs from donor 2 exhibited lower % specific killing when activated by UVADEX/UVA-treated xAPCs, but greater % specific killing when activated by UVADEX/UVA plus freeze-thaw-treated xAPCs, relative to nontreated xAPCs. Furthermore, in three of the four donors (donors 1, 2, and 3) CTLs activated by UVADEX/UVA plus freeze-thaw-treated xAPCs exhibited greater % specific killing then CTLs activated by UVADEX/UVA alone.

Collectively, these experiments demonstrated that xAPCs subjected to either a psoralen/UVA or a psoralen/UVA plus freeze-thaw regimen were rendered essentially nonviable and noninfectious, and possessed essentially equivalent or enhanced exogenous protein expression, selected peptide loading and presentation, and naïve CD8+ T cell activation properties relative to those possessed by xAPCs that were not subjected to these inactivation regimens.

Figure 8B:
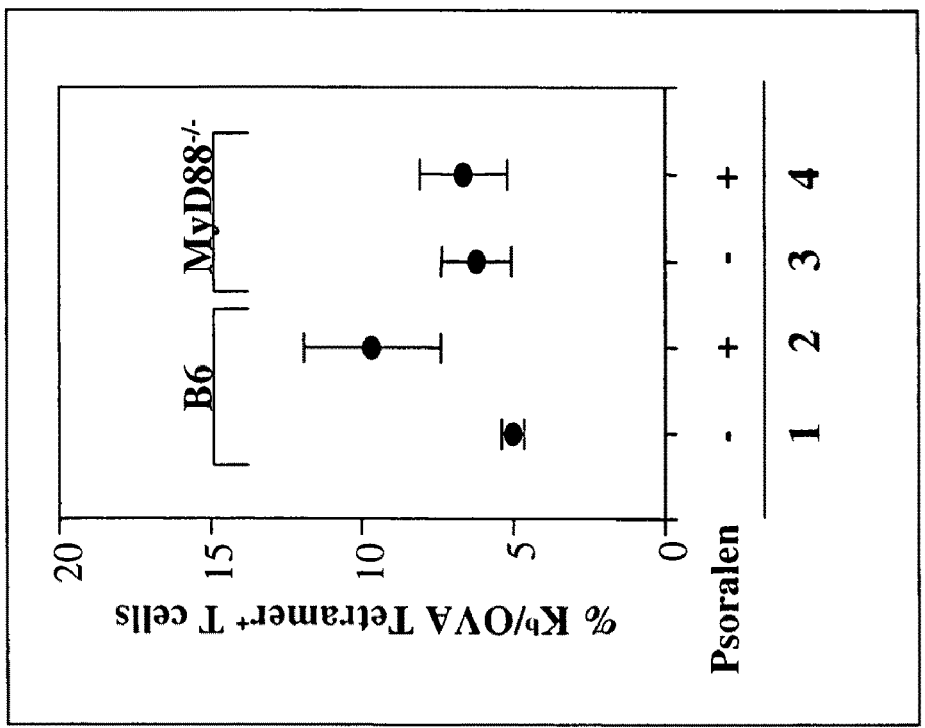
FIGS. 8A and 8B show MyD88-dependent enhancement of activation of antigen-specific CTLs by UVADEX/UVA-treated xAPCs as compared to untreated xAPCs.
Figure 8A:
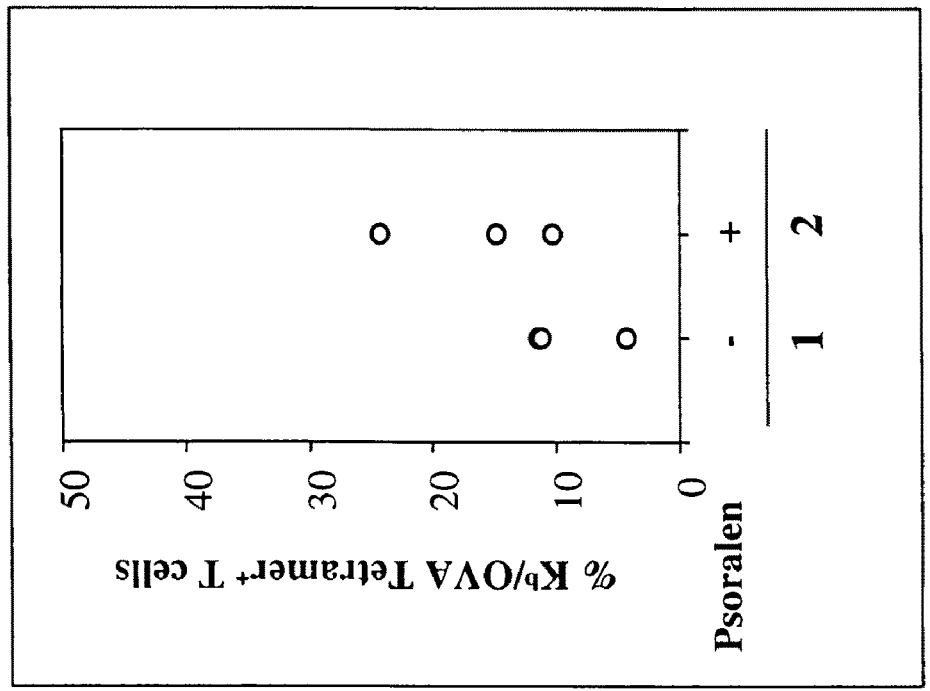
Figure 9A:
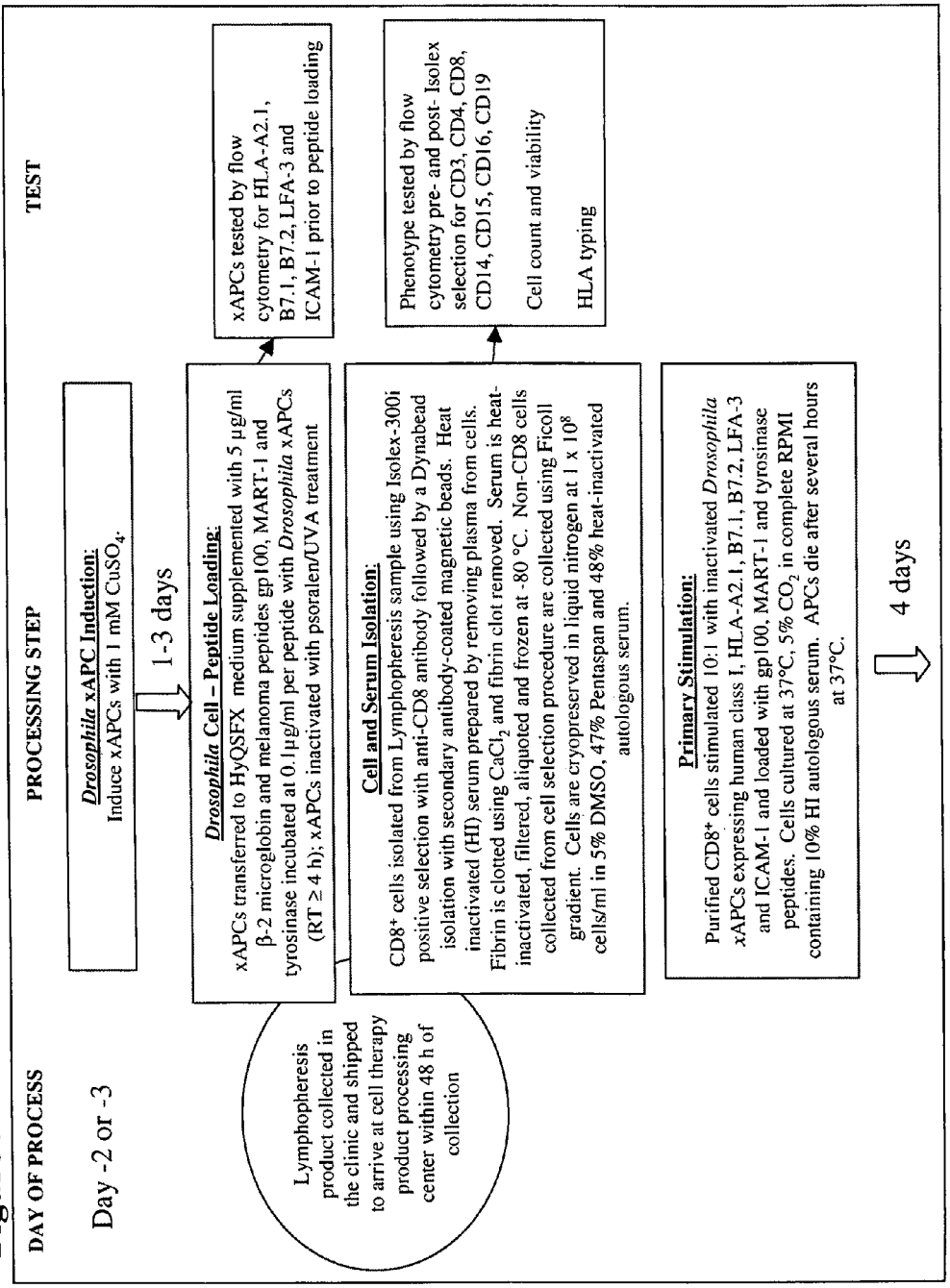
FIGS. 9A-9F provide a flow diagram describing steps of an especially preferred embodiment of a cell therapy method in accordance with the invention.
Figure 9B:
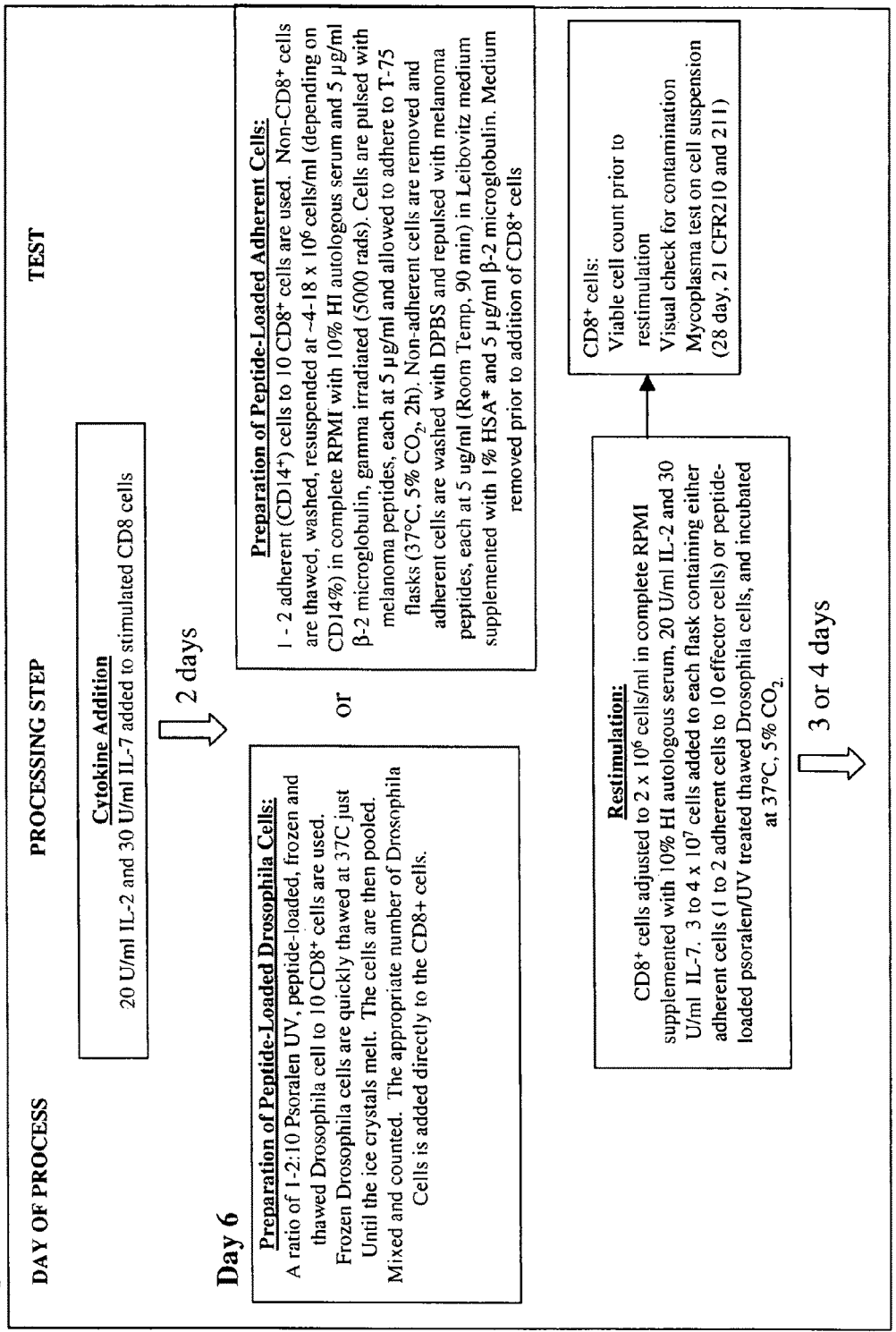
Figure 9C:
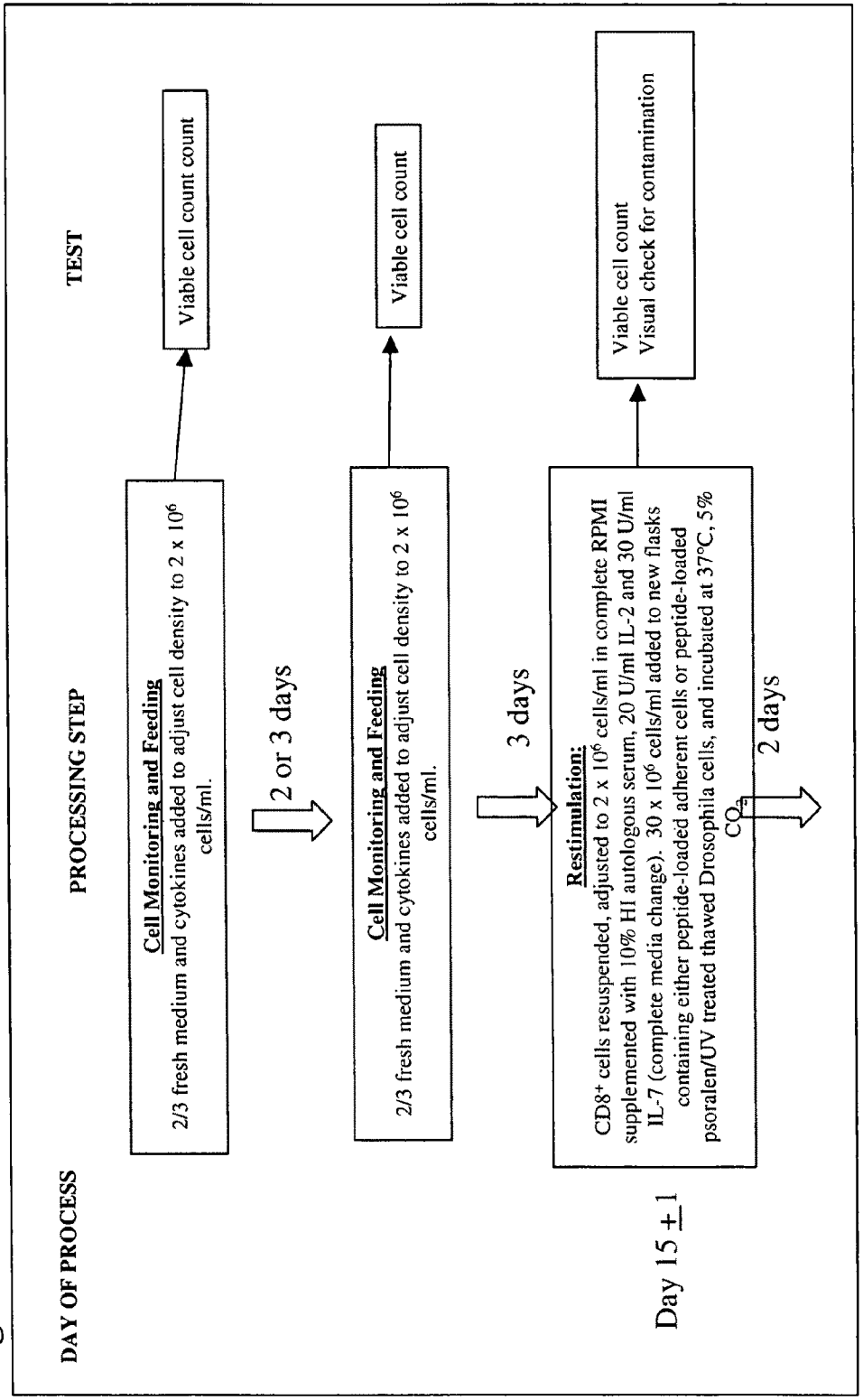
Figure 9D:
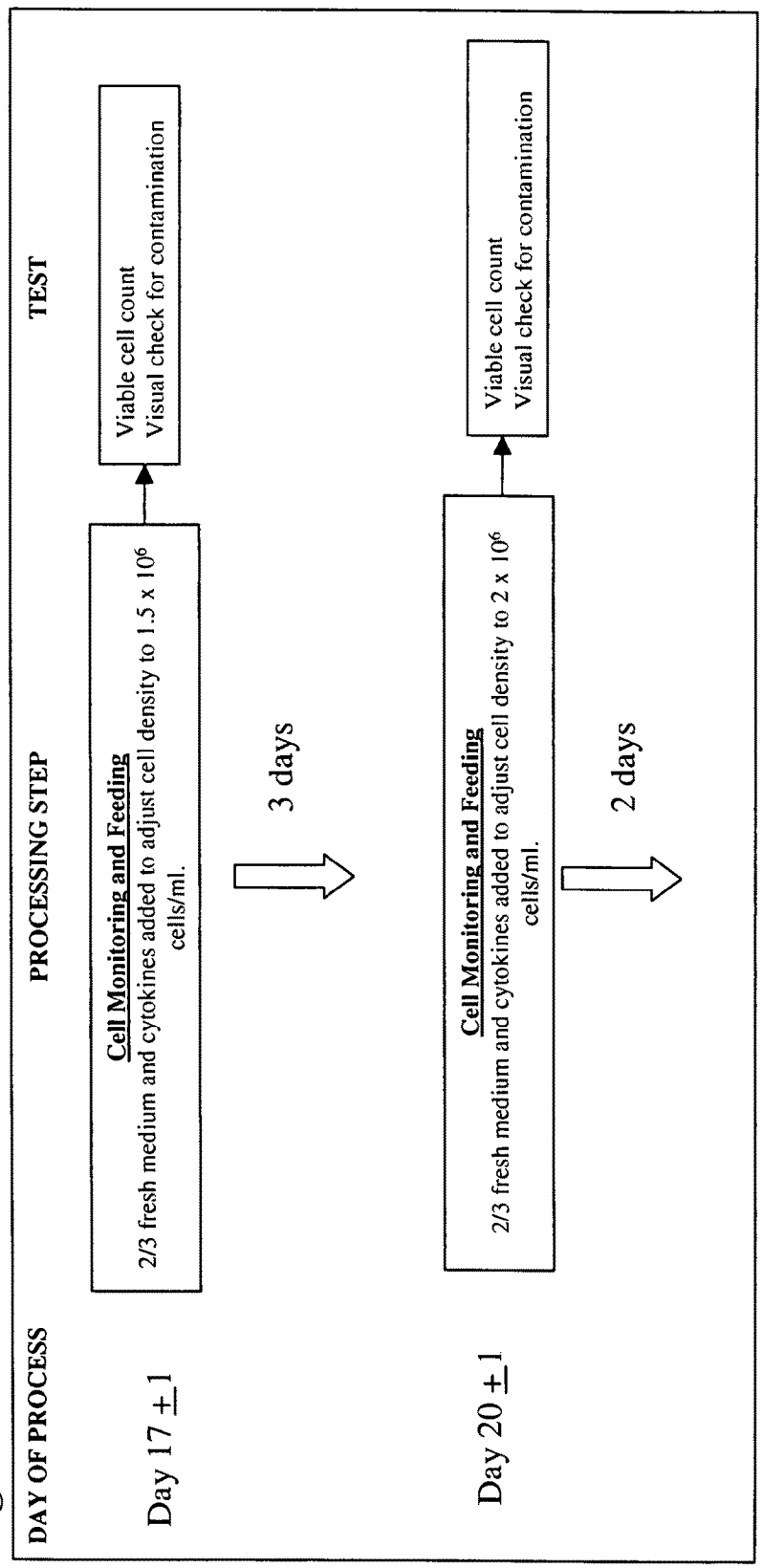
Figure 9E:
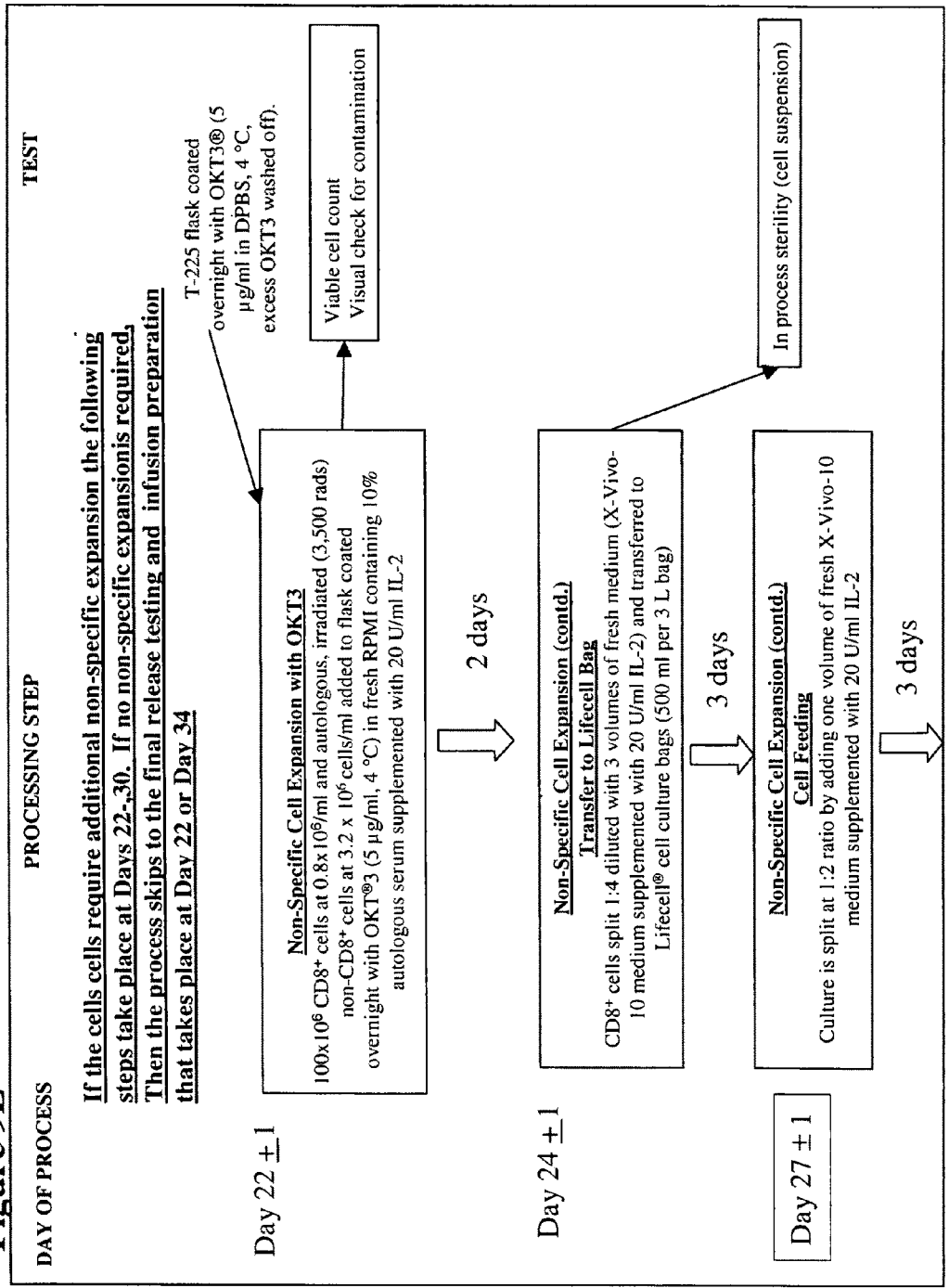
Figure 9F:
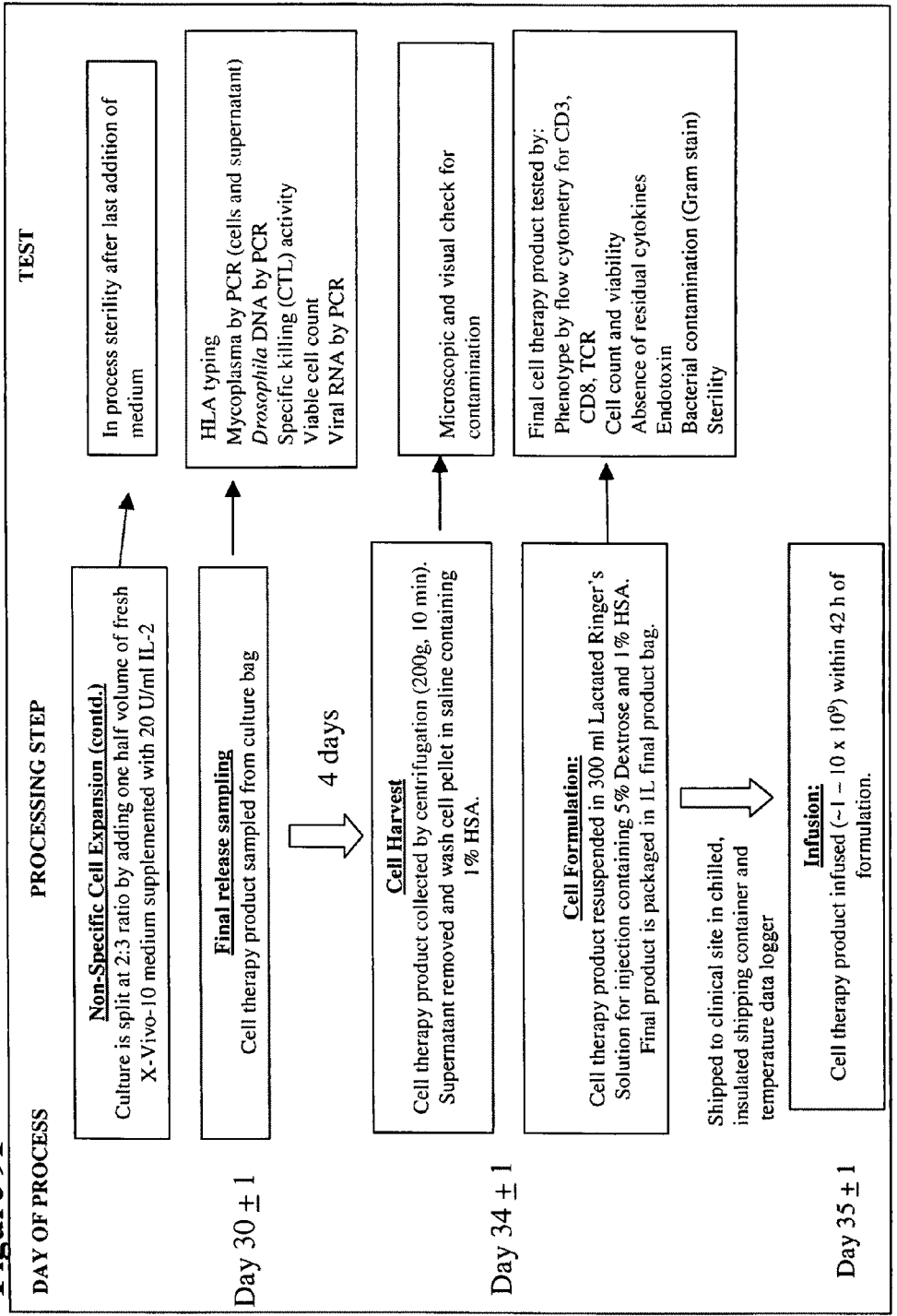

In order to investigate the molecular basis for the enhanced APC function observed with psoralen/UVA treated xAPCs, *Drosophila* xAPCs expressing $K^b$, B7-1, and ICAM-1 molecules were loaded with an OVA8 peptide (SIINFEKL; SEQ ID NO:69) and then treated with or without UVADEX/UVA. Naïve CD8+ T cells were purified from C57BL/6 (B6) mice or MyD88 knockout (MyD88$^{-/-}$) mice and cultured with UVADEX/UVA treated or nontreated *Drosophila* xAPCs that had been loaded with the OVA8 peptide. IL-2 was added on day three and day five of the xAPC/naïve CD8+ T cell coculture. The coculture was split on day seven of the coculture period, and on day nine the cultured CD8+ T cells were collected. An OVA8/MHC tetramer (Beckman Coulter) preparation was prepared and 10 μl was mixed with 1×10⁶ CD8⁺ T cells cells/100 μl of FACS buffer (0.5% BSA, 0.2%, NaN₃ in PBS). The K^b/OVA8 tetramers consisted of four MHC molecules bound to the OVA8 peptide, which was conjugated to a fluorescent protein. The mixture was incubated at room temperature for 30 minutes and washed in PBS, and then spun down at 400×g for 5 minutes. The cell pellet was resuspended in FACS buffer (500 μl) and immediately read on a FACScan flow cytometry machine at an excitation wavelength of 486 nm-580 nm and an emission wavelength of 586 nm-590 nm. The results showed that a higher percentage of CD8⁺ T cells isolated from wild type (C57BL/6 (B6)) mice were stained with the K^b/OVA tetramer when activated with UVADEX/UVA treated *Drosophila* xAPCs compared to the percentage of CD8⁺ T cells stained when activated by non-treated cells *Drosophila* xAPCs (FIG. 8A, lane 2 vs. lane 1). However, no increase was observed in the percentage of CD8⁺ T cells isolated from MyD88 knock-out (MyD88⁻/⁻) mice that were of stained with the K^b/OVA tetramer when activated with UVADEX/UVA treated *Drosophila* xAPCs compared to the percentage of CD8⁺ T cells stained when activated by non-treated cells *Drosophila* xAPCs (FIG. 8B, lane 4 vs. lane 3). Thus, it was concluded that the enhanced activation observed when T cells were incubated UVADEX/UVA-treated xAPCs occurs is dependent on the presence of the MyD88 protein.

Example 3

Preparation of Human Melanoma Antigen Directed Cytotoxic T-Lymphocytes for Cell Therapy The examples above describe the characterization, inactivation, and subsequent use of xAPCs loaded with selected peptide in methods to activate autologous naïve T cells ex vivo. The resulting activated T cells are cytotoxic towards target cells in a selected antigen-specific manner. This example describes the preparation of a preferred CTL therapy product designed for use in a cell therapy regimen to treat melanoma cancer patients in a clinical setting. FIGS. 9A-9F provide a flow diagram outlining steps in the process, including xAPC and CTL characterization procedures and product quality control procedures.

Culture, Induction and Peptide Loading of *Drosophila* xAPCs

*Drosophila* cells are grown in continuous culture at 27° C. in Schneider's *Drosophila* medium supplemented with 10% fetal bovine serum and G418 (Geneticin). The continuous culture of *Drosophila* cells are split twice a week and fresh media is added to adjust the cell density to 1×10⁶/mL. On Day −3 or −2, *Drosophila* cells are split to 1×10⁶/mL and grown in medium without G418. On Day −2 or −1, the *Drosophila* cells are induced to become xAPCs by adding CuSO₄ at 1 mM and are tested on Day 0 to verify expression of HLA-A2, CD80 (B7.1), CD86 (B7.2), CD54 (ICAM-1) and CD58 (LFA-3) by FACS analysis prior to peptide loading. Preferably, ≧80% of the xAPCs express the co-stimulatory molecules CD54 (ICAM1), CD58 (LFA3), CD80 (B7.1), CD86 (B7.2) and HLA-A2.1 (Class I) at any given time point. Use of cells is discontinued when expression of HLA-A2.1 or the other human molecules declines to ≦30%.

*Drosophila* xAPCs and associated viruses are then inactivated with a psoralen/UVA regimen as described above. Inactivation and sterility of the xAPCs may be assessed by performing any or all of the xAPC characterization procedures as described above. On Day 0, the induced, inactivated *Drosophila* xAPCs (1×10⁷/mL) are loaded with the following melanoma-associated peptides, at 0.1 μg/mL per peptide: YMNGTMSQV (SEQ ID NO:5); YMDGTMSQV (SEQ ID NO:6); AAGIGILTV (SEQ ID NO:9); ITDQVPFSV (SEQ ID NO:7); KTWGQYWQV (SEQ ID NO:70); and YLEPGPVTA (SEQ ID NO:8). Peptide loading is performed for a minimum of 4 hours at room temperature in HYQ SFX Insect medium supplemented with 5 μg/mL of beta-2 microglobulin. Peptide-loaded *Drosophila* cells are then mixed with purified CD8⁺ cells as described below.

Collection and Processing of Pheresis Sample

A lymphapheresis product, which comprises leukocytes obtained from a subject, is collected from a patient at a clinical site. Following collection, lymphapheresis products and blood draws (one gas-permeable bag of cells resuspended in autologous plasma and five 10-ml red top tubes of blood, respectively) are shipped the same day at ambient temperature in standard blood transport containers containing a temperature data logger. Shipments are tracked and received the following day. The lymphapheresis product is held at ambient temperature up to 48 hours following collection.

In order to generate a heat-inactivated serum preparation from the red top tubes of blood, the tubes are wiped with alcohol and transferred to a biosafety cabinet. With a 5-ml pipette, the liquid fraction is transferred to 15-ml conical tubes and centrifuged for 10 minutes at 3,000 rpm (1,800×g). The supernatant (serum) is then transferred to a 50-ml conical tube, the red blood cell pellets are discarded, and the supernatant is heat-inactivated by incubating the supernatant for 30 minutes in a 56° C. water bath. The heat-inactivated serum is then aliquoted in 15-ml conical tubes and stored at 4° C. This heat-inactivated serum is used to initiate the CD8 cell culture.

In order to generate a heat-inactivated serum preparation from plasma collected from lymphapheresis product, an amount of CaCl₂ sufficient to neutralize the sodium citrate present in the plasma portion of the lymphapheresis product is determined. This determination is made by dispensing six 1 mil aliquots of plasma from the lymphapheresis product into six polystyrene tubes. Ten, 15, 20, 25, 30, or 35 μl of sterile 1 M CaCl₂ is added independently to each of the six tubes, so that each tube contains ten, 15, 20, 25, 30, or 35 ml CaCl₂. The tubes and the remaining plasma, which is placed in a 500 ml Nalgene bottle, are placed in a 37° C. water bath and incubated for 30 minutes. If the clot is soft after incubation at 37° C., the incubation is extended another 15 minutes at room temperature to achieve complete clotting. The lowest amount of CaCl₂ necessary to produce complete clotting is used to determine the lowest concentration of CaCl₂ necessary to produce complete clotting in the remaining plasma in the Nalgene bottle. An amount of CaCl₂ sufficient to achieve this concentration when added to the volume of plasma in the Nalgene bottle is then added to the Nalgene bottle. The tubing from a 600 ml transfer bag is then clamped with a screw clamp. The plasma is then transferred to the 600 ml transfer bag by piercing the bag with a plasma transfer set (Charter Medical) and connected to a 60 ml slip-tip syringe. The tubing attached to the syringe is then clamped after the plasma has been transferred to the bag.

The reconstituted plasma is incubated at 37° C. for 30 minutes in the water bath, leaving the bag's tubing outside of the water bath, and then allowed to sit at room temperature until the clot starts to shrink. The serum from the clotted plasma bag is then drained into two 250 ml bottles (Nalgene; catalog 2019-250) using tubing attached to the bag.

Before heat-inactivation, two 1.5 ml samples of this serum are aliquoted, placed in Wheaton tubes, and archived at −80° C. The remaining serum in the two 250 ml Nalgene bottles is then heat-inactivated by incubating them in a 56° C. water bath for 40 minutes. After heat-inactivation, the serum is distributed in 50 ml sterile centrifuge tubes and centrifuged for 10 minutes at 3,000 rpm (1,800×g) to pellet insoluble material. Remaining insoluble material is removed from the supernatants by filtering them on 0.45 µm filters. The filtrates are then distributed in 125 ml sterile bottles (Nalgene; catalog no. 2019-125) and stored at −80° C. Tubes containing the insoluble pellets are discarded.

Positive Selection of $CD8^+$ Cells and Isolation of Non-CD8 Cells.

On day 0, the $CD8^+$ and non-CD8 cells are isolated using the Isolex 300i Magnetic Cell Selection System with a disposable tubing set, anti-CD8 monoclonal antibody, immunomagnetic beads (DynaBeads®) and a CD8 elution peptide, AAEGLDTQRFSG (SEQ ID NO:83). The $CD8^+$cell selection procedure is automated and consists of the following steps: cell concentration and platelet wash; incubation with anti-CD8 antibody; a rosetting step using DynaBeads® conjugated to sheep anti-Mouse (SAM) IgG; capture of $CD8^+$ cells; and removal of non-$CD8^+$ cells.

In order to carry out the cell concentration and platelet wash step of the $CD8^+$ cell positive selection procedure, a two-liter transfer bag (Fenwal; catalog number 4R2041) is obtained, into which approximately 1740 ml of DPBS/HSA/citrate wash buffer is transferred by piercing the bag with a plasma transfer set (Charter Medical) and connecting to a 60-ml slip-tip syringe. After transfer the tubing is sealed.

Isolex Set Up.

The Isolex 300i Magnetic Cell Selection System set-up and testing procedure is performed up to one hour before the subject's cells are expected to arrive. The main switch of the Isolex 300i is turned on, and the internal self checks are verified to have occurred before the Nexell Identification Software Version Screen is displayed. After the "System Stop Verification" screen appears, the "Stop" button is pressed and then the weight scales and pressure values from the "Device Status" screen are recorded. In order to perform System Initialization, the instructions on screen are followed to clear the device components. After the initialization tests are completed, the weight scales and pressure values from the "Device Status" screen on the Cell Processing and Quality Control Log ("After Initialization") are recorded. On the "Select a Procedure" screen, "Positive Selection Only" is selected.

Isolex Disposable Set Installation.

The tray containing the disposable set is removed from packaging. The Isolex 300i disposable set is installed by opening the pump door and hanging the two connected 2000 ml waste bags (bags B and C, respectively) on the holder on the right side of the instrument. The tubing is draped over the spinner housing below the display. The single 2000 ml bag (Bag A) is placed on the bench top. The paper tape is removed from chamber tubing and the chamber is installed in the rocker module. Both re-circulation wash bags (no.5) are hung on Weight Scale 5 with the filtered wash bag positioned in front. The end product bag (no.4) is hung on Weight Scale 4. The antibody bag (no.3) is hung on Weight Scale 3. Finally, the release agent bag (no.2) is hung on Weight Scale 2. All of the disposable set parts remaining in the tray are loosened, and the tray is removed. Next, the spinning membrane assembly is then installed into the spinner module, ensuring that the support arm is in place and the spinning device is seated correctly. Proper tubing placement behind each manifold is then verified, the upper two clamp manifolds and lower three clamp manifolds are locked in place, and the pump organizer is snapped in place. All tubing in the organizer is then verified to be centered on the pump rollers or in the grooved surface of the pump module cover. The pump door is then closed. The P1 tubing and spinning device tubing are verified as not being pinched by the door, and the secondary magnet separation bag is installed on the secondary magnet using the tubing guides. The magnet door is then closed.

Matching the blue dots, tubing in Fluid Detectors 1 and 2 is installed, and tubing placement is confirmed in the "Device Status" screen. The Luer fittings are securely attached to Pressure Transducers 1 and 2. Matching the blue dot, tubing is then installed in Fluid Detector 3. The chamber tubing then installed in the rocker tubing guide on the bottom of the rocker arm. The paper tape holding the buffer bag and Weight Scale 5 bag tubing is removed, and the cell source bag and buffer bag tubing is draped such that they do not interfere with the tubing from the bags on the scales. Bags are checked to ensure that they are hanging straight on weight scales, and the disposable set tubing is checked for kinks and pinches. Next, the clamp on the tubing to the single 2000 ml bag (Bag A) is closed; the tubing to Bags B and C is verified to be open. After the disposable set is properly installed, "OK" is selected on the "Install Set" screen. Twenty tests are internally conducted to verify proper disposable set installation.

Buffer Installation and Priming of Disposable Set.

The DPBS/HSA/citrate buffer bag is connected to the disposable set buffer line spike. While holding the buffer bag upright, the bag is slapped to eliminate air from the port connection line. A 1 kg weight is attached to Weight Scale 6, and the buffer bag is hung on the 1 kg weight. The combined weight is to be between 3250 g-7000 g. The weight scales and pressure values from the "Device Status" screen are recorded, and "OK" is selected. The Isolex 300i Magnetic Cell Selection System then primes the disposable set with buffer. The weight scales and pressure values from the "Device Status" screen are recorded after the prime set is complete. The Isolex 300i is kept on hold until the patient cells have been received and are ready to be added. The disposable set installation and priming is initiated up to one hour before the patient cells are expected to arrive, so that cell processing may begin immediately upon receipt.

After receiving the patient lymphapheresis shipping bag, wipe down the port on the shipping bag is wiped with a sterile cloth and 70% isopropyl alcohol, and then transferred to a clean biosafety cabinet. Using a spike-spike transfer line, the contents of the bag are transferred to a 500 ml sterile bottle (Nalgene; catalog number 2019-0500). A 1:50 dilution of cells is then prepared by mixing 0.02 ml of cell suspension with 0.98 ml of 2% acetic acid. The cells are then counted to determine the PBMC cell count.

Cell Count of Lymphapheresis Product.

A 50 ml pipette is used to dispense cells suspended in plasma into 50 ml conical centrifuge tubes (45 ml/tube). The cells are pelleted by centrifugation for 10 minutes at 1,000 rpm (200×g), with the brake off. The number of PBMCs are calculated by multiplying the cell concentration by the total volume. The plasma supernatant (40 ml/tube) is then pooled into a 500 ml sterile bottle (Nalgene; catalog number 2019-0500) to be used for plasma processing as described below. The pellets are resuspended in the plasma remaining in the 50 ml tubes, and pool into a sterile 250 ml bottle (Nalgene; catalog number 2019-0250). The volume is then measured. Approximately 150 ml of DPBS/HSA/citrate is then added, and the total volume is calculated by dividing the total cell number by the new cell volume.

Isolation of $CD8^+$ Cells.

Phenotype and CD8 purity testing is determined by cell surface staining with fluorescent-labeled monoclonal antibodies and analysis by flow cytometry. Two-color analysis on the FACScan flow cytometer is performed according to the panel of monoclonal antibodies listed below. Markers for product characterization include: CD3 (T lymphocytes), CD4 (T helper cells), CD8 (T cytotoxic cells), CD14 (monocytes), CD19 (B cells), CD16 (NK Cells) and CD15 (granulocytes). Cells used for flow cytometry testing are washed in FACS buffer (PBS containing BSA and sodium azide) and incubated with the appropriate fluorescent-labeled monoclonal antibodies at 4° C. for 15-30 minutes, protected from light. Post incubation, the stained cells are washed and resuspended in FACS buffer. Stained cells are stored on ice, protected from light, and run on the flow cytometer within 2 hours of staining. Alternatively, if the samples cannot be analyzed within 2 hours, the samples are fixed using a solution of 0.5% paraformaldehyde in DPBS and stored for up to a week at 4° C. in the dark. A total of 10,000 events are collected for each sample. Data is analyzed and the percentage of cells that are positive for each marker is reported.

A total of $1 \times 10^8$ cells are pipetted for HLA typing/FACS analysis into a sterile 50 ml conical tube. The cell concentration (cells/ml) is recorded on the tube. Approximately $6 \times 10^7$ cells are set aide in a sterile 15 ml tube to be frozen for archiving of patient lymphocytes. Cells are centrifuged and frozen at the same time as the non-CD8 cells are frozen (see below for isolation and processing of non-CD8 cells). Approximately $1 \times 10^7$ cells are set aside in a sterile 15 ml tube for FACS analysis before Isolex 300i-mediated positive selection of CD8$^+$ cells.

Reagents are added to the Isolex 300i and the data recorded according to the following steps, and may be added while the patient cells are being centrifuged. Once the "Add Release Agent" screen appears, the septum of Bag 2 is wiped with sterile alcohol wipes. A needle and syringe is used to add 20 ml of DPBS/HSA/citrate buffer to Bag 2. The release agent is replaced with DPBS/HSA/citrate buffer, and then "OK" is pressed. Once the "Add Antibody" screen appears, the septum of Bag 3 is wiped with sterile alcohol wipes. Anti-CD8 monoclonal antibody 37B1A solution is prepared by mixing 0.200 ml of 37B1A stock at 10 mg/ml with 2.30 ml of DPBS/HSA/citrate. Using a needle and syringe, the diluted 37B1A anti-CD8 mAb is added to Bag 3, and "OK" is pressed. Once the "Add Beads" screen appears, the septum of the chamber is wiped with sterile alcohol wipes. Magnetic beads (Nexell 4R9950, or equivalent) are washed by transferring the content of one vial (10 ml) into a 50 ml tube and adding 10 ml of DPBS/HSA/citrate. Beads are separated for 2 minutes on an MPC-1 magnet by placing the tube on the magnet. Supernatant is removed with a pipette while the beads are attracted to the side of the tube. The tube of beads is removed from the magnet, and the beads gently resuspended in 10 ml of DPBS/HSA/citrate such that foaming is avoided. Using a needle and a 20 ml syringe, the beads are added to the chamber, and then "OK" is pressed.

The tubing of a 300 mL Transfer Pack container (Baxter-Fenwal; catalog number 4R2014) is then sealed. In a biosafety cabinet, the cell suspension from the 250 mL bottle is transferred into the 300 mL Transfer Pack using a 60 ml syringe (plunger removed) connected to a Blood Component Infusion Set. The infusion set tubing is then sealed. The cell suspension is then transferred from the transfer pack container into the 1000 ml Isolex 300i bag included in the disposable set (Nexell; catalog number 4R9850), using the spike and the in-line blood filter to eliminate clumps of cells. The tubing of the bag containing the cell suspension is then sealed.

Selection of CD8$^+$ Cells.

The Isolex 300i cell bag is connected by using the spike on the Isolex Disposable Set and hung to weight scale number 1, and the weight scales and pressure values from the 'Device Status' screen on the cell processor are recorded. 'OK' is pressed, and the clamp of waste bag A (non-CD8 collection bag) is confirmed to be closed. The clamp of waste bags B and C is opened before starting the positive selection sequence. The Isolex is allowed to proceed to wash away platelets for 15 minutes before incubating the cells with the anti-CD8 mAb (37B1A). After completion of the platelet wash and during the antibody incubation, the weight of the cell bags (weight scale No. 5) are recorded. After the antibody incubation, the Isolex is allowed to proceed to wash away excess antibody and then transfer the cells into the chamber containing the magnetic beads, where mixing occurs for 30 minutes to cause resetting. During the rosetting of the cells (after the Isolex finishes rinsing all the tubing) the clamp of waste bag A is opened, and the clamps of waste bags B and C are closed. The chamber volume is recorded during resetting. After resetting is complete, the rosettes are magnetically collected against the side of the chamber and the non-CD8 cells are drained into waste bag A. The Isolex system is allowed to proceed to wash the rosettes three times with approximately 100 ml of DPBS/HSA/citrate buffer. After the third and final wash, "Stop" stop is pressed on the Isolex keypad and the chamber is sealed. The chamber containing rosetted CD8$^+$ cells is removed from the Isolex machine. The chamber and tubing are then sprayed with sterile alcohol and placed in a biosafety cabinet (e.g., a hood), and 15 ml of DPBS/HSA/citrate are added through the chamber septum cleansed with a sterile alcohol wipe. The chamber is then tilted back and forth to resuspend the rosettes, and the suspension is transferred into a 50 ml tube using a 30 ml syringe fitted with a 16-gauge needle. The transfer is repeated twice and the transferred suspensions are pooled. The rosettes are then separated for 5 minutes on an MPC-1 magnet, and the supernatant is discarded.

Elution of CD8$^+$ Cells with CD8 Elution Peptide.

The washed rosettes are resuspended with 6 ml of DPBS/HSA/citrate and transferred to a 15 ml sterile conical tube, to which 0.9 ml of CD8 elution peptide (AAEGLDTQRFSG; SEQ ID NO:83) are added at 10.0 mg/ml (final peptide concentration: 1.5 mg/ml). The rosette/peptide solution is incubated at 37° C. for 30 minutes on a Dynal mixer rotating at 20 rpm. The incubated solution is mixed vigorously with a 5 ml pipette. The pipette is rinsed twice with 2 ml of DPBS/HSA/citrate, and the rinsed volume is added to the 15 ml tube. Beads are separated from the cells on a MPC-6 magnet for 3 minutes and the supernatant collected, which contains CD8$^+$ cells, in a 50 ml conical tube. The beads are washed three times with 10 ml of DPBS/HSA/citrate, and the separation step on the magnet is repeated. The supernatants containing released CD8$^+$ cells are pooled together with the first supernatant. Stray beads are removed from the pooled cell suspension by separating for 5 minutes on the MPC-1 magnet. The pooled supernatant is transferred to a 50 ml conical tube and its volume is measured. After dilution at 1:20 with trypan blue (20 μl cell suspension+380 μl trypan blue) the cells (viable and dead) are counted using a hemocytometer, The ratio of live cells (not stained by trypan blue) to total cells (stained plus non-stained cells) calculated as a percentage is defined as cell viability. Approximately $4.0 \times 10^7$ are removed cells for immediate testing by FACS analysis, cell characterization and virus testing, split equally into two sterile 15 ml conical tubes. The remaining CD8$^+$ are pelleted by centrifugation for seven minutes at 1,700 rpm (600×g). The supernatant is aspirated with a 25 ml pipette, and then recentrifuged for one minute at 1,700 rpm (600×g) to pellet the cells. Excess supernatant is removed using a fine tip pipette. The cell pellet is resuspended with 14 ml of DPBS/HSA/citrate, transferred to a 15 ml sterile conical tube, and again centrifuged for seven minutes at 1,700 rpm (600×g). The supernatant is then again aspirated with a 10 ml pipette, recentrifuged for one minute at 1,700 rpm (600×g) to pellet the cells and excess supernatant removed using a fine tip pipette. The cell pellet is then resuspended in a T75 flask to a concentration of $3.3 \times 10^6$ cells/ml using complete RPMI medium supplemented with 10% of heat-inactivated autologous serum (HIAS), prepared as described above. FACS analysis of cell sample is performed and the results recorded.

Collection of Non-CD8 Cells.

After the rosette washes are complete as described above, waste bag A is sealed, wiped with sterile alcohol and transferred into a biosafety cabinet (e.g., a hood). The waste bag is spiked with a sterile spike and spike connector, and the cell suspension collected in a pre-weighed sterile 500 ml bottle (Nalgene; catalog number 2019-0500). After collection, the bottle is weighed again to estimate the volume of non-CD8 cell suspension based on the approximation that 1 g=1 ml). The remaining bags and tubing of the Isolex set are then discarded. DPBS is then added to make the volume of the cell non-cCD8 suspension up to 480 ml and mixed. See below if the volume of the non-CD8 cell suspension is greater than 480 ml prior to addition of DPBS.

Separation and Harvest of Non-CD8 Cells.

In order to separate non-CD8 cells, 15 ml of Ficoll-Paque PLUS (Pharmacia; catalog number 17-1440-03) are pipetted into each of sixteen 50 ml centrifuge tubes. If the volume of the non-CD8 cell suspension collected as described above is greater than 480 ml, the non-CD8 suspension volume is divided by 16 in order to calculate the volume to deliver into to each 50 ml centrifuge tube. Approximately 30 ml (or 1/16th of the total volume as described above), of the non-CD8 cell suspension is carefully layered on top of the Ficoll-Paque PLUS. The tubes are placed in centrifuge buckets and balanced carefully by adding water to the buckets. The balanced buckets are centrifuged at 2,000 rpm (800×g) for 20 minutes at room temperature with the brake off. With a 10 ml pipette, the non-CD8 cells are collected from the top of the Ficoll-Paque PLUS layer (e.g., between 13 and 15 ml/interface) and the material transferred to twelve 50 ml conical tubes, approximately 20 ml of cell suspension per tube maximum. Each tube is filled to 50 ml with DPBS. The tubes are then centrifuged for 10 minutes at 1,700 rpm (600×g) with the brake on. The supernatant is then aspirated and discarded, cell pellets resuspended in a total of 200 ml of DPBS/HSA/citrate buffer, and the resuspended cells transferred into 4×50 ml sterile tubes and centrifuged for seven minutes at 1,700 rpm (600×g). Supernatants are again aspirated and discarded. The cell pellets are then resuspended in 50 ml of DPBS/HSA/citrate buffer and homogenized. The homogenate is then passed through a sterile Falcon 2350 cell strainer to remove any clumps of cells.

Preparation of Cell Samples.

The non-CD8 cell homogenate prepared as described above is diluted in 2% acetic acid at a ratio of 1:100 (10 µL cell suspension+990 µL of acetic acid) in order to lyse remaining red blood cells. Cells are then counted with a hemocytometer. Approximately $2 \times 10^6$ cells for FACS analysis. The analysis is performed within two hours, or fixed. Once FACS analysis is performed on the cell sample, the data is recorded. Remaining non-CD8 cells are pelleted by centrifugation for 7 minutes at 1,700 rpm (600×g), the supernatant is aspirated, and the pellet is resuspended at a density of $1 \times 10^8$ cells/ml in freezing medium, which is 5% DMSO, 47% Pentaspan and 48% heat-inactivated autologous serum (prepared as described above). Approximately 2 ml of extra freezing medium is prepared for use as a temperature probe. The freezing medium is then placed on ice until ready to use. The cell suspension is then distributed into Nunc freezing vials in approximately 1.0 ml aliquots (about 10 vials' worth), and remaining cells are distributed in 4.0 ml aliquots. An extra vial containing 1.0 ml of freezing medium is prepared for use as the temperature probe of the freezing system. All vials, including the temperature probe vial, is then placed on ice. The $6 \times 10^7$ lymphocytes that were set aside as described above are pelleted by centrifugation for seven minutes at 1,700 rpm (600×g), and the supernatant is aspirated. The cell pellet is then resuspended in 6 ml of freezing medium. Nunc freezing vials are labeled with protocol number and patient information, and the cell suspension is distributed into the vials in approximately 1.0 ml aliquots (about 6 vials' worth). The vials are then placed on ice.

Primary Stimulation of CD8+ Cells with *DROSOPHILA* xAPCs

Stimulation of CD8+ cells is performed immediately after completion of the CD8+ cell selection procedure described above. The CD8+ cell suspension prepared as described above is mixed at $3.3 \times 10^6$ cells/ml in RPMI 1640 medium, which is supplemented with L-glutamine, non-essential amino-acids, sodium pyruvate and HEPES solution, containing 10% autologous serum, with the suspension of peptide-loaded *Drosophila* xAPCs, prepared and peptide-loaded as described above, at a ratio of one xAPC to ten CD8+ cells. This corresponds to approximately 0.1 ml of xAPC suspension for every 3.0 ml of CD8+ cell suspension (1:30 dilution factor). Then, the number of flasks needed is determined by dividing volume (in mls) of the xAPC-CD8+ cell mixed suspension by 15 ml. Color-coded labels are affixed to T75 flasks (Costar 3376) and labeled with patient number, date, and volume. The xAPC-CD8+ cell mixed suspension containing xAPCs and CD8+ cells is then homogenized by swirling, and the homogenate is distributed equally in the flasks. No less than 15 ml of cell suspension is added to each flask. Flasks are then set upright in a dedicated humidified 37° C. incubator with 5% $CO_2$ and incubated for four days.

On day four of the process, the cell culture is sampled for gamma IFN production, and IL-2 and IL-7 are added to 20 IU/ml and 30 U/ml final concentration, respectively. First, 3 ml the cell suspension supernatant is removed from three flasks (0.9 ml total) and placed in an Eppendorf tube. The Eppendorf tube is spun for two minutes in a microcentrifuge. The supernatant is transferred to a new Eppendorf tube and stored at −80° C. The amount of each stock cytokine required is then calculated: cytokines are diluted to 1:1,000 of the concentration of the stock, and an appropriate volume of this diluted stock is added to the cells in RPMI without serum (0.5 ml/flask). Once this calculation is completed, the cytokine stocks are removed from −80° C. freezer and thawed rapidly at 37° C. The cytokines are kept on ice once thawed, and used within two hours of the initial thaw. The remaining cytokine tubes are placed at −80° C. Cytokines are discarded after one freeze/thaw cycle. The cytokines diluted in medium are distributed to each flask, and each flask is returned to the incubator.

First Restimulation of Primed CD8+ Cells with Non-CD8 Adherent Cells

Peptide-loaded xAPC-primed CD8+ cells, which are effector cells, are restimulated with peptide-loaded adherent cells (non-CD8 cells) on Day 6 or 7 at a ratio of 1 to 2 adherent cells to 10 effector cells. First, cells are pooled for restimulation on day 6 of process. Effector cell T75 flasks are removed from the incubator and inspected visually and microscopically for possible contamination. Any identified contaminated flasks are discarded before pooling of cells for restimulation.

Uncontaminated effector cells are pipetted into a T225 flask with vented cap, and the cells counted with a hemocytometer after diluting them 1:4 in trypan blue (50 µl cell sample+150 µl trypan blue). A volume of the cell suspension equivalent to approximately of $15\times10^6$ effector cells used for mycoplasma testing (28 day culture method; described below). Flasks with remaining cells are returned upright to the incubator until ready to process further.

Preparation of Primed Effector Cells for Restimulation.

Up to $4\times10^8$ CD8$^+$ primed effector cells are restimulated. The volume required to suspend the amount of primed effector cells to be restimulated at $2\times10^6$ cells/ml is calculated. The calculated cell suspension volume is divided by 15-18, representing 15 ml-18 ml aliquots, in order to ascertain how many T75 flasks with adherent cells should be prepared for the restimulation procedure. The CD8$^+$ primed effector cells are harvested either during the adherence or peptide-pulsing procedures for the adherent cells, as described below. Excess effector cell suspension may be frozen for further use by centrifuging at 1,700 rpm for seven minutes, removing the supernatant, and resuspending the cell pellets to a concentration of $1\times10^8$ cells/ml in freezing solution (DPBS containing 10% DMSO and 5% HAS), which has been pre-chilled on ice prior to addition to the cell pellets. Once cells are resuspended with the pre-chilled freezing solution, the resuspension is aliquoted into an appropriate number of freezing vials, and the freezing vials are then placed in a StratCooler Cryo Preservation Module that has been pre-cooled to 4° C. The StratCooler Cryo Preservation Module is then transferred to a −80° C. freezer and left overnight. The next day, the vials are transferred to a −140° C. freezer.

Preparation of CD14$^+$ Non-CD8 Cells for Restimulation.

The range of the number of CD14$^+$ non-CD8 cells needed in the restimulation procedure is determined by multiplying the number of CD8$^+$ primed effector cells to restimulate by 0.1 and 0.2, such that a ratio of approximately 1 to 2 CD14$^+$ non-CD8 cells to 10 CD8$^+$ primed effector cells will be achieved. The range of the number of non-CD8 cells to thaw is then calculated by dividing both numbers of CD14$^+$ non-CD8 cells needed by the percentage of CD14$^+$ non-CD8 cells present in the non-CD8 fraction as determined by flow cytometry, as described above. The numbers are rounded to the nearest $1\times10^8$ cells. The autologous non-CD8 cells that were earlier frozen at $1\times10^8$ cells/vial (see above) are then quickly thawed in a 37° C. water bath. The thawed cells are washed by transferring up to five vials into a 50 ml conical tube and slowly adding 9.0 ml of complete RPMI per each ml of frozen cells. A 20 µl sample of the cell suspension from one of the tubes is diluted with 180 µl of trypan blue (i.e., 1:10 dilution), and the viable cell count is determined. The total number of viable, thawed non-CD8 cells is then determined by multiplying the total thawed non-CD8 cell suspension volume by the cell count determined for the 20 µl sample. The recovery percentage is also determined by dividing the number of viable cells by the theoretical number of thawed cells. This recovery % is used in subsequent restimulation and non-specific expansion procedures, described below. The number of recovered viable non-CD8 cells is confirmed to be within the range of non-CD8 cells required as determined above. If needed, an additional vial of non-CD8 cells is thawed and counted in order to achieve this required amount. The cell suspension is transferred into sterile 50 ml conical tubes and pelleted by centrifugation for seven minutes at 1,500 rpm (450×g). Supernatants are aspirated and discarded. A volume of complete RPMI supplemented with 10% heat-inactivated autologous serum (HIAS) and β2 microglobulin at 5.0 µg/ml (1:200 dilution of the 1.0 mg/ml stock) sufficient to add at 3.5 ml per flask of CD8$^+$ effector cells to be restimulated, plus an extra 1.0-1.5 ml, is prepared. The non-CD8 cell pellets are resuspended with this medium and pooled into a single sterile 50 ml conical tube. The 50 ml conical tube containing the non-CD8 cell suspension is placed in a zip-lock bag and gamma-irradiated at 5,000 rads. After irradiation, the non-CD8 cells are returned to the biosafety cabinet.

Adherence and Loading of Non-CD8 Cells with Melanoma Peptides.

The melanoma peptides used in the primary stimulation of the CD8$^+$ cells are added to the irradiated cells at 30 µg/ml final concentration (1:333 dilution of the 10.0 mg/ml stock in DMSO). The cell suspension-peptide mixture (3.5 ml/flask) is then distributed in T75 flasks with vented caps (Costar 3376) and incubated upright for two hours at 37° C. in 5% $CO_2$ to allow for adherent cells to attach to the plastic surface.

The non-adherent cells are dislodged by gently pipetting the supernatant against the adherent cell layer with a 5.0 ml pipette, and the dislodged cells are discarded.

Remaining adherent cells are washed by pipetting 5 ml of DPBS into each flask and then discarding the wash. A volume of Leibovitz L15 medium supplemented with 1% HSA (1:25 dilution of stock at 25%), 5.0 µg/ml of β2 microglobulin (1:200 dilution of stock at 1.0 mg/ml) and 30.0 µg/ml of melanoma peptides combination mixture (1:333 dilution of stock at 10.0 mg/ml) is prepared that is sufficient to deliver 3.5 ml per flask of adherent cells. To each flask is then added 3.5 ml of the medium, and the flasks are then incubated upright for 90 minutes at room temperature in a biosafety cabinet.

Incubation of Primed CD8$^+$ Effector Cells with Adherent Peptide-loaded Non-CD8 Cells.

The primary stimulated CD8$^+$ effector cells prepared as described above are harvested for restimulation with the non-CD8$^+$ adherent cells by first calculating the total volume needed to adjust the remaining CD8$^+$ effector cells in the T225 flask to $2.0\times10^6$ cells/ml. The T225 flasks containing CD8$^+$ effector cells are then removed from the incubator and placed in a biosafety cabinet (e.g., a hood). With a pipette, enough cell suspension from the pooled cells in the T225 flask are removed to leave one third of the total volume, adjusted at $2.0\times10^6$ cells/ml. Remaining cell suspension is placed in an appropriate number 50 ml conical centrifuge tubes. The cell suspension in the 50 ml conical tubes is centrifuged for seven minutes at 1,700 rpm (600×g), and the supernatant is removed with a pipette. This supernatant, which is conditioned medium, is retained for mycoplasma testing, described below. Excess effector cell suspension may be frozen for further use by centrifuging at 1,700 rpm for seven minutes, removing the supernatant, and resuspending the cell pellets to a concentration of $1\times10^8$ cells/ml in freezing solution (DPBS containing 10% DMSO and 5% HSA), which has been pre-chilled on ice prior to addition to the cell pellets. Once cells are resuspended with the pre-chilled freezing solution, the resuspension is aliquoted into an appropriate number of freezing vials, and the freezing vials are then placed in a StratCooler Cryo Preservation Module that has been pre-cooled to 4° C. The StratCooler Cryo Preservation Module is then transferred to a −80° C. freezer and left overnight. The next day, the vials are transferred to a −140° C. freezer.

Using a volume of medium equivalent to ⅔ of final volume, the pelleted effector cells are resuspended in fresh complete 10% RPMI supplemented with 10% HIAS, IL-2 at 20 U/ml and IL-7 at 30 U/ml, and added to the cells left in conditioned medium in the T225 flask. Medium from the T75 flasks coated with peptide-pulsed autologous adherent cells is aspirated in a biosafety cabinet (e.g., a hood). The effector cell suspension is then pipetted into the coated flasks, 15-18 ml/flask, as calculated above. The flasks are then returned to the incubator and incubated at 37° C., 5% $CO_2$ for three or four days, depending on whether the xAPC stimulation was performed on a Wednesday or a Tuesday, respectively.

The sample set aside for mycoplasma testing as described above, is then prepared by first adjusting the mycoplasma testing sample to $0.5\times10^6$ cells/ml (30 ml final volume) by adding back the supernatant, which is conditioned medium, that was saved for mycoplasma testing. The mixture is then aliquoted into two aliquots at 2 ml each and one aliquot at 26 ml. Each aliquot is frozen by placing in either dry ice/isopropanol or liquid nitrogen, sealed with Parafilm®, placed in a zip-lock bag, and stored at −80° C. until shipped on dry ice to BioReliance for mycoplasma testing.

Cell Density Adjustments and Medium Changes for Effector Cells after First Restimulation.

Cell density adjustment and medium changes are performed on days 9±1 and 12±1 of the cell therapy production process. The procedure for performing these adjustments and medium changes is identical for each day, and is presented below. First, the adherent cell-coated T75 flasks containing the effector cells are removed from the incubator and the cells counted from one flask to determine the viable cell count by preparing a 1:4 dilution with trypan blue (50 μl cell sample+ 150 μl trypan blue). From the obtained viable cell count, the total volume needed to adjust the cell density to $2\times10^6$ cells/ml is calculated. With a pipette, enough cell suspension is removed so as to leave one-third of the total volume in the flask. The removed suspension is placed place in 15 ml conical centrifuge tubes (1 tube per T75 flask), centrifuged for seven minutes at 1,700 rpm (600×g), and the supernatant removed. The cell pellets are then resuspended with a volume of fresh complete RPMI supplemented with 10% autologous serum and cytokines that corresponds to two-thirds of the total volume. The resuspended cells are then added back to the cells left in the conditioned medium in the T75 flasks. The T75 flasks are then returned to the incubator and incubated at 37° C., 5% $CO_2$ for three days.

Second Restimulation of Primed $CD8^+$ Effector Cells with Adherent Peptide-loaded Non-CD8 Cells.

Primed $CD8^+$ effector cells that have undergone the first restimulation with non-CD8 adherent cells are prepared for a second restimulation on day 15±1 of the cell therapy production process. The procedures for the counting, preparation, irradiation, adherence, and melanoma peptide-loading of non-CD8 adherent cells for the second effector cell restimulation are the same as those described above for the first restimulation. Harvesting of the $CD8^+$ effector cells is performed during the 90-minute peptide-loading incubation period if not already harvested during cell adherence incubation. The T225 flask of CD8+ pooled effector cells is removed from the incubator and placed in a biosafety cabinet (e.g., a hood). With a pipette, a cell suspension volume equal to up to $5\times10^8$ cells is removed from the pooled cells. The removed volume is placed in an appropriate amount of 50 ml conical centrifuge tubes. The cell suspension in the tubes is then centrifuged for seven minutes at 1,700 rpm (600×g), and the supernatant is removed and discarded. Next, the total volume needed to resuspend the pelleted effector cells to $2.0\times10^6$ cells/ml in fresh complete RPMI (supplemented with 10% HIAS, IL-2 at 20 U/ml and IL-7 at 30 U/ml). Excess cells are frozen in freezing solution as described above in the first restimulation procedure. The medium from the T75 flasks coated with peptide-loaded autologous adherent cells is aspirated in a biosafety cabinet (e.g., a hood). The effector cell resuspension is pipetted into the T75 flasks at 15 ml-18 ml per flask. The T75 flasks are then returned to the incubator and incubated for two days at 37° C., 5% $CO_2$.

Cell Density Adjustments and Medium Changes for Effector Cells after Second Restimulation.

Cell density adjustment and medium changes are performed on days 17±1 and 20±1 of the cell therapy production process. For the cell density adjustment and medium change on day 17±1, the adherent cell-coated T75 flasks containing the effector cells are removed from the incubator and the cells counted from one flask to determine the viable cell count by preparing a 1:4 dilution with trypan blue (50 μl cell sample+ 150 μl trypan blue). From the obtained viable cell count, the total volume needed to adjust the cell density to $1.5\times10^6$ cells/ml is calculated. With a pipette, enough cell suspension is removed so as to leave one-third of the total volume in the flask. The removed suspension is placed place in 15 ml conical centrifuge tubes (1 tube per T75 flask), centrifuged for seven minutes at 1,700 rpm (600×g), and the supernatant removed. The cell pellets are then resuspended with a volume of fresh complete RPMI supplemented with 10% autologous serum and cytokines that corresponds to two-thirds of the total volume. The resuspended cells are then added back to the cells left in the conditioned medium in the T75 flasks. The T75 flasks are then returned to the incubator and incubated at 37° C., 5% $CO_2$ for three days. The procedure for cell density adjustment and medium change on day 20±1 is identical to that employed on day 17±1, except that the total volume needed to adjust the cell density is calculated for a final cell density of $2\times10^6$ cells/ml instead of $1.5\times10^6$ cells/ml.

Non-Specific $CD8^+$ Effector Cell Expansion by OKT3 Stimulation

On day 21±1 of the cell therapy production process (one day prior to non-specific cell expansion), four T225 flasks are coated with OKT3 by adding 30 mil of OKT3 mAb diluted to 4.0 μg/ml in DPBS (120 μl of OKT3 sterile solution stock at 1.0 mg/ml in 30 ml DPBS) to each flask. The vents of the flasks are then sealed with Parafilm and stored horizontally overnight at 4° C. Each T225 flask will be used for the stimulation of a total of $8\text{-}10\times10^7$ effector cells.

The next day (day 22±1), $CD8^+$ effector cells are prepared for stimulation with OKT3 mAb. The flasks containing $CD8^+$ effector cells are removed from the incubator and inspected visually and microscopically for possible contamination. Identified contaminated flasks are discarded. Uncontaminated cells are pooled into a sterile 500 ml sterile Nalgene bottle and counted after dilution at 1:4 with trypan blue (50 μl cell sample+150 μl trypan blue). A viable cell count is then determined. Approximately $5\text{-}10\times10^6$ viable cells are set aside for tetramer staining, and another $40\text{-}60\times10^6$ viable cells are set aside *Drosophila* virus testing. The volume of effector cell suspension to collect for stimulation with OKT3 is then calculated based on the number of flasks coated with anti-CD3 antibody and the target viable cell count per OKT3-coated flask of $8\text{-}10\times10^7$ effector cells. Any extra cells are frozen using the freezing procedure described above. The Nalgene bottle is then returned to the incubator.

A number of non-CD8 cells to thaw out to be used as feeder cells during the non-specific cell expansion is calculated using a ratio of four non-CD8 feeder cells to stimulate one $CD8^+$ effector cell. Assuming the recovery of viable cells per frozen non-CD8 vial is the same as that determined for the first restimulation procedure above, the number of non-CD8 cells needed is divided by the percent recovery of viable cells. This number is rounded to the nearest $4\times10^8$ cells, as each vial of frozen non-CD8 cells contains approximately $4\times10^8$ cells. Once the number of non-CD8 cells required is determined, the autologous non-CD8 cells are quickly thawed in a 37° C.

water bath. The thawed cells are then transferred into an appropriate number of sterile 50 ml conical tubes, to which 9 ml of complete RPMI medium without serum is added for every 1 ml of thawed cells. The thawed cells are pelleted by centrifugation for seven minutes at 1,500 rpm (450×g), and the supernatants aspirated and discarded. The pellets are then resuspended to approximately $1.5 \times 10^7$ cells/ml in complete RPMI supplemented with 10% heat-inactivated autologous serum (HIAS), and the cell suspension is transferred into a sterile 250 ml centrifuge tube. The centrifuge tube containing the non-CD8 cell suspension is placed in a zip-lock bag and gamma-irradiated with 3,500 rads. After irradiation, the non-CD8 cells are returned to the biosafety cabinet. The irradiated non-CD8 cells are then added to the pool of $CD8^+$ effector cells in the 500 ml Nalgene bottle.

The total volume required to add 125 ml of the non-CD8/$CD8^+$ cell suspension into each OKT3-coated flask is determined, and the difference between this total volume and the current volume of the non-CD8/$CD8^+$ cell suspension Nalgene bottle is made up by adding fresh medium (complete RPMI supplemented with 10% heat-inactivated autologous serum) to the Nalgene bottle. Fresh IL-2 is then added to 20 IU/ml (1:5,000 dilution of stock at 100 IU/μl). From this point on, no IL-7 is added to the culture The OKT3-coated flasks are then removed from the refrigerator, the OKT3 solution is removed from the flasks with a pipette, and each flask is washed four times with 30 ml of DPBS each wash. The non-CD8/$CD8^+$ cell suspension is then distributed among the OKT3-coated flasks (125 ml/flask) and incubated horizontally for two days at 37° C., 5% $CO_2$. Two days later (Day 24±1), the flasks are removed from the incubator, and the cell suspension is collected from each flask using a long-handled sterile cell scraper, handling each flask separately. Each flask contains 125 ml of cell suspension.

The luer-fitted port of a 3L Lifecell® bag (Nexell; catalog number R4R2113) is attached to a 60 ml sterile syringe (without plunger), and the clamps on the other ports are closed. The contents of each flask is transferred into a separate bag, so that the number of Lifecell bags filled with cell suspension equals the number of OKT3-coated flasks from which the cells derived. To each Lifecell bag is then added 375 ml of X-Vivo10 medium (BioWhittaker; catalog number 04-743Q) and 100 μl of fresh IL-2 stock at 100 IU/μl (to achieve a 20 IU/ml final concentration). The total volume of each cell suspension in each Lifecell bag is now approximately 500 ml. The Lifecell® bags are then returned to the incubator and placed on a wire rack to allow efficient gas exchange. The bags are incubated for three days at 37° C., 5% $CO_2$.

At the end of the three-day incubation period (Day 27±1), 500 ml of X-Vivo10 medium (BioWhittaker; catalog number 04-743Q) is added to each Lifecelle® bag. Fresh IL-2 is added to 20 IU/ml (1:5,000 dilution of stock at 100 IU/μl). After adding fresh medium, the clamp on the luer port of each bag is closed, the bag is swirl to homogenize the cell suspension, and a 5 ml sample of the cell suspension is drawn with a syringe for sterility testing, described below. Each sample is tested separately. Samples are tested within two hours of being taken. After sampling, the clamp on the luer port is again closed, and the luer connection is capped with a 3 ml syringe. The Lifecell® bags are then returned to the incubator and placed on a wire rack to allow efficient gas exchange. The bags are incubated for 3 days at 37° C., 5% $CO_2$. At the end of the three-day incubation period (Day 30±1), 500 ml of X-Vivo10 medium (BioWhittaker; catalog number 04-743Q) is added to each Lifecell® bag. Fresh IL-2 is added to 20 IU/ml (1:5,000 dilution of stock at 100 IU/μl). The volume of each bag is now approximately 1,500 ml. After adding fresh medium, each bag is swirled to homogenize the cell suspension and a 2 ml sample is drawn with a syringe from one of the bags to determine viable cell count. The viable cell count is determined in the 2 ml sample after 1:4 dilution in trypan blue (50 μl cell sample+150 μl trypan blue).

Sample Testing Prior to Harvest and Release of Cell Therapy Product

Prior to cell therapy product harvesting and release, the cell therapy product is sampled for BacT/Alert sterility testing, HLA typing, mycoplasma testing by PCR, endotoxin testing, gram stain testing, detection of *Drosophila* DNA, detection of viral RNA by PCR, and cell therapy product phenotype and activity testing (including cell number and viability determination, phenotype determination, and $CD8^+$ purity). These tests are performed at various other in-process steps in the cell therapy manufacturing process, as mentioned above and depicted in FIGS. 9A-9F.

Using the viable cell count determined on day 30±1, the volume of cell suspension equivalent to $5 \times 10^7$ cells to be sampled from each Lifecell® bag is calculated. Using a separate syringe for each bag, the calculated volume equivalent to $5 \times 10^7$ cells is removed and placed in separate T75 flasks. Cells in the flasks are visually inspected for unusual color or cloudiness and checked microscopically for indications of possible contamination. Any Lifecell bag from which contaminated cells are detected is discarded. A 5 ml sample from each of the T75 flasks is removed to initiate sterility testing by BacT/Alert as described below. Each sample is tested separately. Samples are inoculated within 2 hours of being taken. The remaining cell suspensions are pooled into a T75 flask. The viable cell count in the pooled sample is determined after 1:4 dilution in trypan blue (50 μl cell sample+150 μl trypan blue). A calculated volume corresponding to a total of $1 \times 10^8$ cells is used for DNA and RNA preparation and for Mycoplasma PCR ELISA as described below. A calculated volume corresponding to a total of $1.95 \times 10^7$ cells is used for CTL assay as described below. A calculated volume corresponding to a total $5\text{-}10 \times 10^7$ cells is set aside for tetramer staining as described below. After sampling, the Lifecell bags are returned to the incubator and incubated until ready to harvest cells.

BacT/Alert Testing for Cell Therapy Product Sterility.

In-process BacT/Alert® (bioMerieux, Inc.) sterility testing is initiated on approximately Day 27 (one week prior to cell harvesting), and on approximately Day 30 (after the last addition of medium to the culture). Sampling for release testing is also performed on Day 30, after the last addition of medium to the culture, as described above.

The BacT/Alert® rapid sterility testing method is used to test in-process and final product sterility. BacT/Alert® is an FDA approved diagnostic device. It is a fully automated, non-invasive microbial detection system utilizing colorimetric detection of carbon dioxide production for the detection of microorganism growth. The BacT/Alert® system incubates, agitates, and monitors cultures continuously. The BacT/Alert is used according to the manufacturer's instructions. Once a bottle containing a test sample containing a sample is entered into the instrument, there is no further need for operator intervention until a positive is detected, or the seven-day incubation period is complete. The system consists of a detection instrument, computer system, and aerobic and anaerobic culture bottles with built-in calorimetric sensors.

When a bottle containing a test sample is placed into an instrument cell, a small light-emitting diode (LED) exposes the sensor located at the bottom of each bottle to a red light beam. The reflected light is collected every ten minutes by a photodiode built into each cell, where it is transformed, amplified, and transmitted to the computer system for interpretation. The computer software generates a growth curve for each bottle, and through the use of the detection algorithm, discriminates between constant $CO_2$ production and accelerated rate of $CO_2$ production caused by growing microorganisms. The software algorithm may detect a high $CO_2$ level when a bottle is first loaded into the instrument, or it may sense a high rate of $CO_2$ production, or it may measure an acceleration in the rate of $CO_2$ production. The first two measurements detect organisms that have grown or are growing before entry into the instrument. As additional $CO_2$ is generated within the culture bottle, the built-in sensor changes from dark gray to yellow. Since each sample is compared to its own past performance rather than a preset threshold, true positives are rapidly detected without increase in false positives.

The cell therapy product is conditionally released if all in process BacT/Alert tests are negative on the day of cell infusion. The cell therapy product is stable for 42 hours post formulation, which necessitates immediate shipment to the clinical site prior to obtaining final test results from sterility testing. BacT/Alert is read 18±2 hours after inoculation of the final product. Notification that the 18±2 h sterility reading of final product was negative will be provided to the clinical site. This notification is received prior to cell infusion to document the provisional release of the cell therapy product. Full release is documented after the cell therapy product sample is deemed negative after the full seven-day incubation.

HLA Typing of Cell Therapy Product.

PCR-based HLA typing is performed on samples of lymphapheresis products (PBMCs) and $CD8^+$ effector cell samples obtained from cell therapy product four days prior to cell therapy product harvest. Genomic DNA is prepared from PBMCs or $CD8^+$ effector cells using the Qiagen Blood Amp-DNA kit (Qiagen) according to the manufacturer's instructions. Templates for HLA-A, HLA-A2 and HLA-DR from Genovision typing kits (GenoVision) are prepared for the PCR. The PCR master mix included in the kit is added along with the purified genomic DNA to each template well. Each well is capped and templates loaded onto the thermal cycler. PCR parameters include a combination 10/20 cycle program. Samples are run on 2% agarose gels containing ethidium bromide, and the results photographed using a UV photodocumentation station. The results of the HLA typing are determined by using the lot specific interpretation and specificity tables provided with the Genovision kit. Prior to release, HLA typing results of the cell therapy product are verified for identity with those of the initial lymphapheresis product. HLA match with incoming patient cells are confirmed prior to release of the cell therapy product.

Mycoplasma Testing of Cell Therapy Product.

Cell therapy product samples is tested for mycoplasma using the Roche Mycoplasma PCR-ELISA Kit (Roche). Both $CD8^+$ culture supernatant and genomic DNA prepared from the cell therapy product are tested in this assay. The cell therapy product is sampled as described above, and the cells and/or debris pelleted by low speed centrifugation. The test is performed according to the manufacturer's instructions. Supernatants are removed and centrifuged at high speed to pellet mycoplasma. Supernatants are removed and each pellet resuspended in 10 µl lysis buffer and 10 µl sterile water. Positive control DNA (10 µl) is added to a microfuge tube with 10 µl of lysis buffer. For duplicate negative controls, 10 µl water and 10 µl lysis buffer are added to each of two microfuge tubes. All samples are incubated at 37° C. for one hour. After adding neutralization buffer to each sample 10 µl of each is added to 40 µl of PCR mix. The PCR is run on duplicate samples of $CD8^+$ supernatants together with positive and negative controls following the manufacturer's protocol. Denaturation reagent (40 µl) is incubated for 10 minutes at room temperature with 10 µl each PCR reaction product. Hybridization reaction containing the biotin labeled capture probe is added to each sample and the mixture transferred to the appropriate well of the microtiter plate containing streptavidin-coated MTP. The plate is incubated at 37° C. for three hours with orbital shaking at 300 rpm. After washing, anti-DIG-POD working solution is added and the plate incubated at room temperature for 30 minutes at 300 rpm. The plate is then washed five times and TMB substrate incubated on the plate at room temperature for 20 minutes at 300 rpm. Stop solution is added and absorbance measured using a microtiter plate reader at 450 nm. The test sample is considered positive if the absorbance measured at 450 nm is twice that of the negative controls. The assay is considered valid if the optical density of the negative controls is less than 0.25 and the positive control is >1.2. The test samples are considered negative if the difference in absorbance between the negative controls and the test samples is less than 0.2. For release, the cell therapy product is PCR-ELISA test-negative for mycoplasma.

Endotoxin Testing.

Endotoxin testing is performed by kinetic photometric technique using BioWhittaker's QCL-1000 endotoxin assay kit according to the manufacturer's instruction. The presence of endotoxin in a sample activates enzymes present in a *Limulus* amoebocyte lysate (LAL) preparation. Enzyme activity is detected by adding a peptide substrate. The cleavage of this peptide substrate leads to the release of a colored fragment that is quantified calorimetrically.

The endotoxin content of a product administered by intravenous route is required to be ≦5.0 EU/kg/h. For an average 70 kg individual, this would be equivalent to a total maximum dose of 350 EU. The cell therapy product is formulated in a final volume of 300 mL of Lactated Ringer's Injection USP/5% Dextrose in 0.9% Sodium Chloride/25% human serum albumin, administered over 30 minutes. Thus, the upper endotoxin limit corresponds to 1.17 EU/mL of cell therapy product. Endotoxin levels in the cell therapy product are be below 1.0 EU/mL for product release.

Gram Stain Testing.

Gram stain is performed using a standard test kit for this assay. Each test (3 slides) contains prefixed gram-positive and gram-negative organisms as controls in addition to the cell therapy product test sample. For release, no microorganisms are detected by gram stain on the slide containing the cell therapy product test sample.

*Drosophila* xAPC DNA Screening of xAPCs and of Cell Therapy Product.

$CD8^+$ cells derived from the lymphaheresis product are exposed to *Drosophila* xAPCs at the outset of the manufacturing procedure. *Drosophila* xAPCs are temperature-sensitive (maintained in culture at 25-27° C.) and will die within 48 hrs when cultured at 37° C. A PCR method is used to confirm the absence of *Drosophila* xAPC DNA in the final cell therapy product prior to release. *Drosophila* xAPC DNA is detected by PCR using primers specific for the pRMHa-3 plasmid vector that is used to transfect *Drosophila* cells in order to create the *Drosophila* xAPCs, as described above.

Plasmid pRMHa-3 vector sequences are present at high copy numbers in *Drosophila* xAPCs and remain stable within the cells, providing a suitable marker for the presence of *Drosophila* xAPC DNA in the cell therapy product. The absence of this vector results in loss of recombinant antigen expression, which is always assessed by flow cytometry on the day of the primary stimulation. Plasmid pRMHa-3 plasmid vector is present in *Drosophila* xAPCs that express transfected xenogenic nucleic acid (e.g., human co-stimulatory and adhesion molecules). Primer sequences used for the detection of pRMHa-3 are as follows:

```
                                          (SEQ ID NO: 72)
pRMHa-3   5' primer: 5'- CAGCAGCAAAATCAAGT -3'

(SEQ ID NO: 73)
pRMHa-3   3' primer: 5'- GAAGAATGTGAGTGTGC -3'
```

Figure 10:
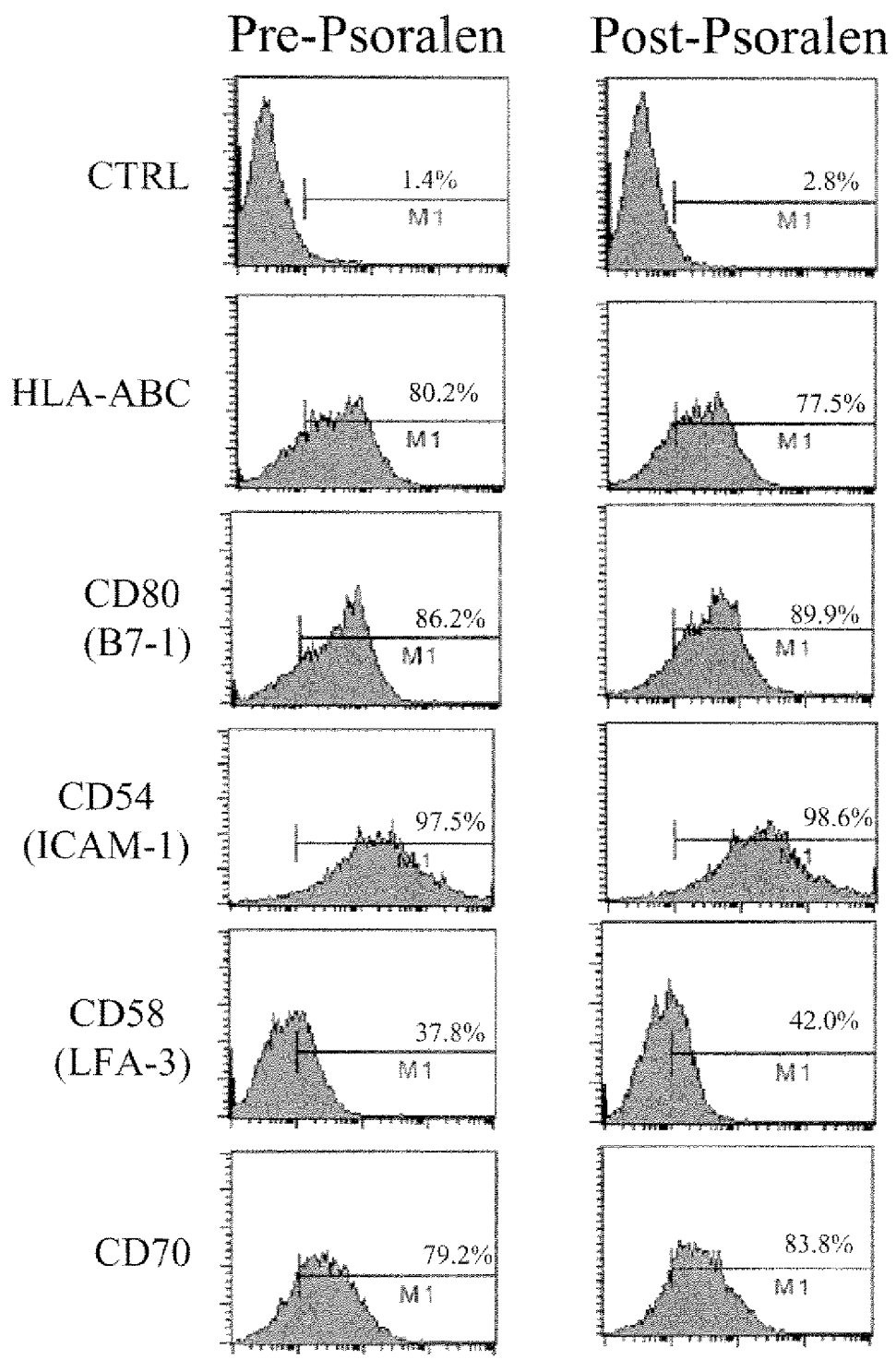
FIG. 10 shows the FACS analysis of surface expression of exogenous molecules on Drosophila xAPCs (1120) that transfected with HLA-A2, B7-1, ICAM-1, LFA-3 and CD70 pre and post Psoralen/UVA treatment. Drosophila xAPCs were cultured with CuSo4 (1 mM) for 48 h at room temperature to induce the expression of exogenous molecules. The induced Drosophila xAPCs were first cultured with UVA-DEX (5 ug/ml for 30 min at 4° C.) and were then exposed to UVA for 10 minutes. The cells were washed extensively with culture medium and stained with antibodies specific for human HLA-ABC, B7-1, ICAM-1, LFA-3 and CD70 respectively and analyzed with a FACscan
Figure 11:
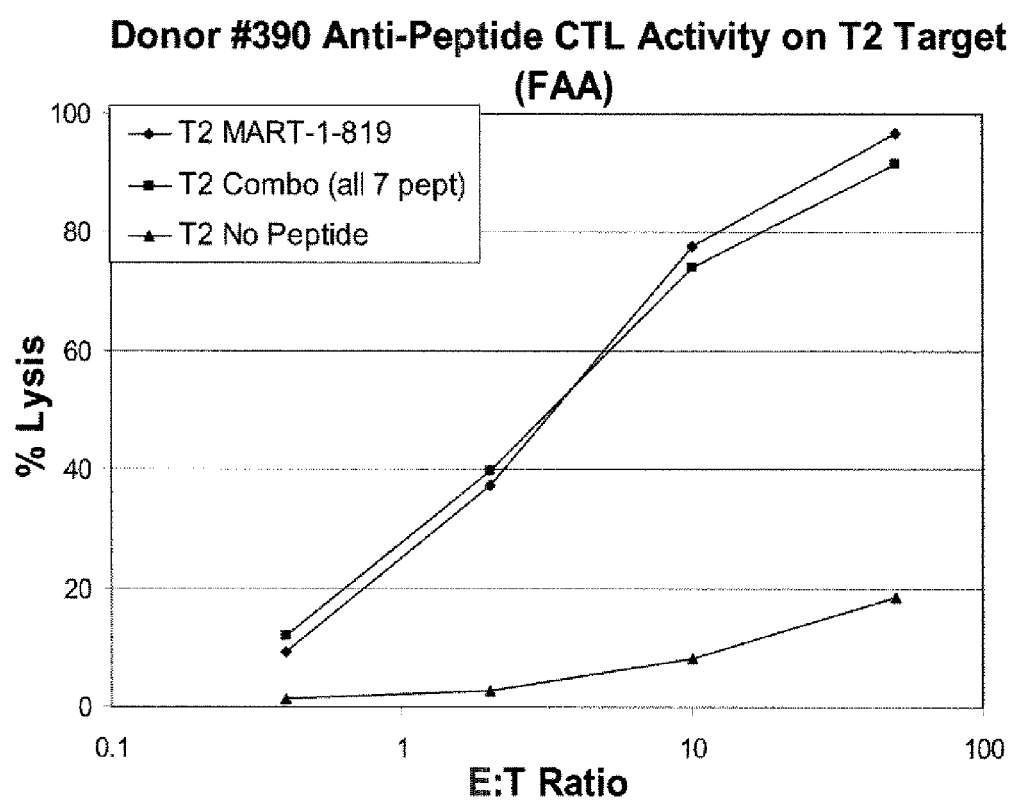
FIG. 11 shows the comparison of CTL activities of ex vivo generated melanoma-specific CTLs restimulated with psoralen-treated Drosophila xAPCs (FFF) or with non CD8 adherent cells from PBMC of the same donor (FAA). Purified human CD8 T cells from HLA-A2 positive donors were cultured with Psoralen/UVA treated Drosophila xAPCs preloaded with a mixture of 6 melanoma peptides (689, 792, 817, 818, 819, 853) at 37° C. At day 4 human IL-2 (20 U/ml) and IL-7 (30 U/ml) were added. The activated CD8 T cells were re-stimulated twice at day 6 and day 14 with either non-CD8 adherent cells from PBMC of the same donor (FAA) or with Psoralen/UVA treated Drosophila APCs (FFF) in the presence of above antigenic peptides with an additional peptide 952 (mMART-1). The antigen-specific CD8 T cells were evaluated by $^{51}$Cr assay. Briefly, $^{51}$Cr labeled M14 cells or peptide-loaded T2 cells were used as targets and CTLs were added at 0.4, 2, 10, 50 effecter/target ratio. Supernatant was collected after 4 hours of culture and the $^{51}$Cr released from the targets was measured with a γ-counter.
Figure 11:
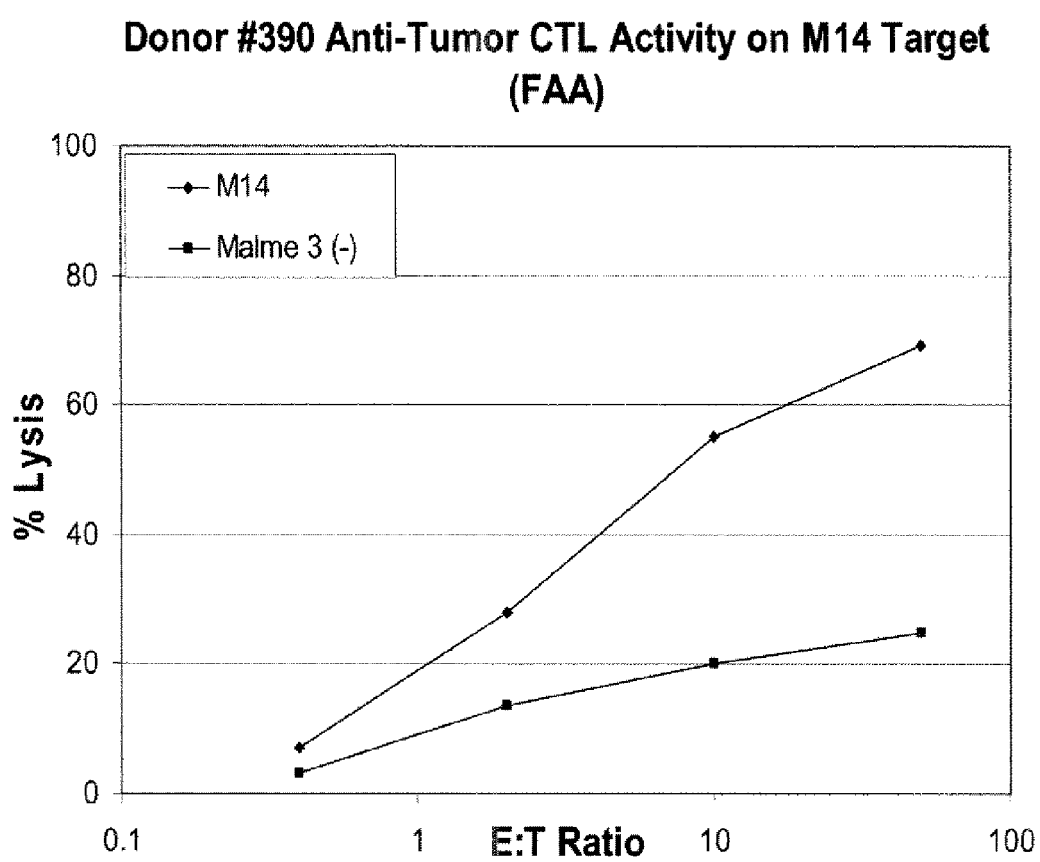
Figure 11:
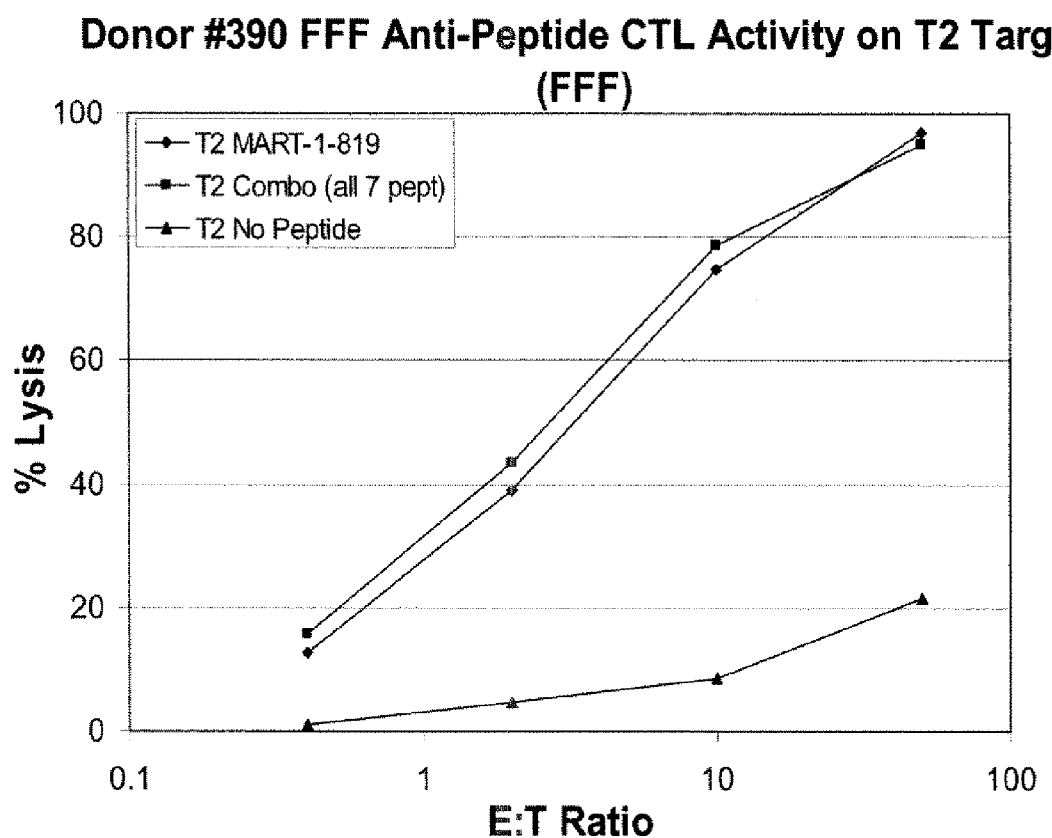
Figure 11:
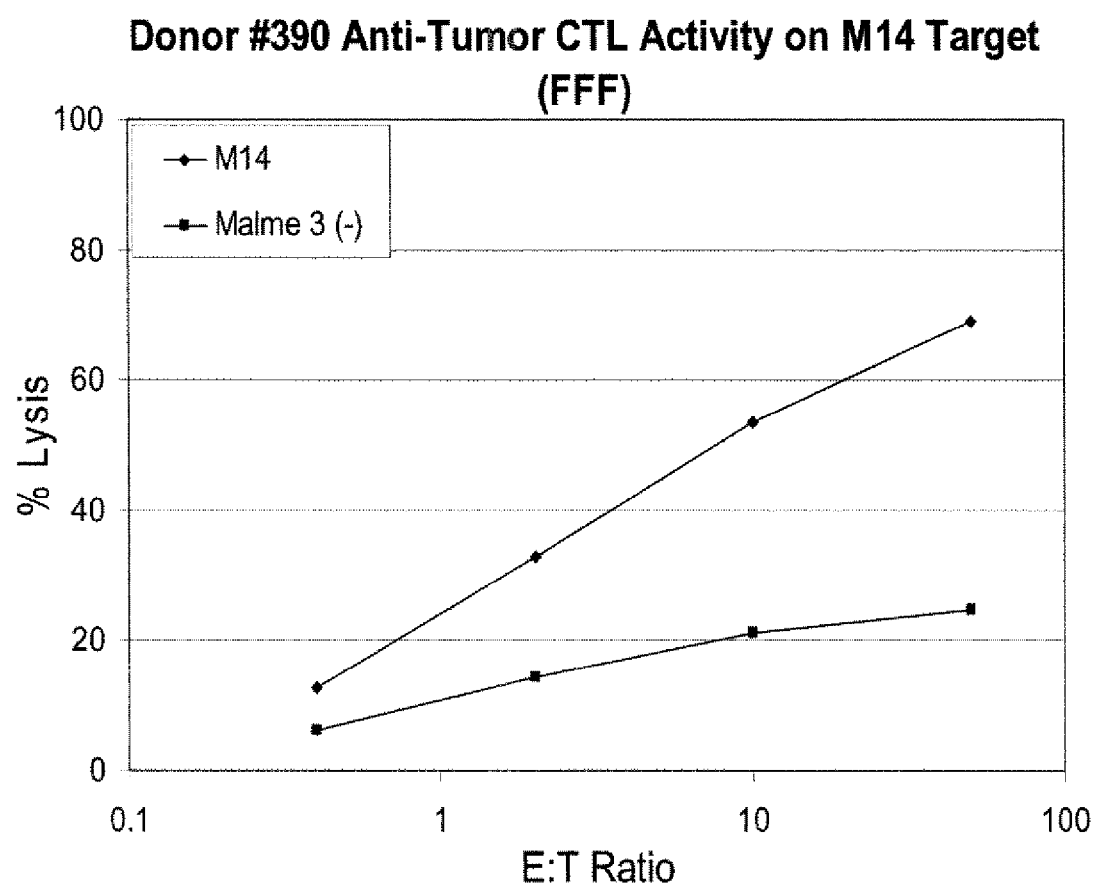
Figure 12:
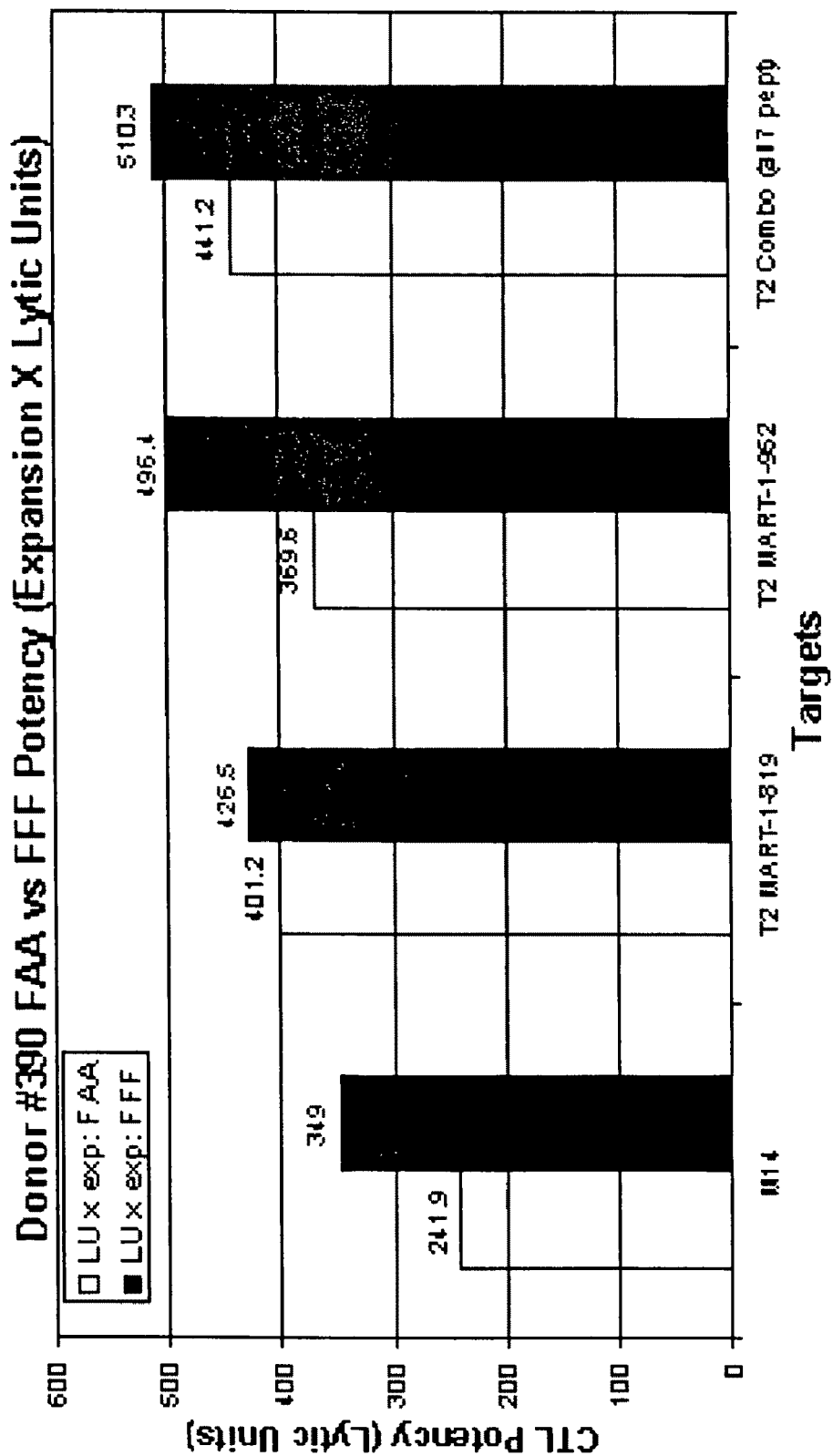
FIG. 12. shows the comparison of CTL potency (expansion×lytic units) of ex vivo generated melanoma-specific CTLs restimulated with psoralen-treated Drosophila xAPCs (FFF) or with PBMC non CD8 adherent cells (FAA). Purified human CD8 T cells from HLA-A2 positive donors were first cultured with Psoralen/UV treated Drosophila APCs pre-loaded with a mixture of 6 melanoma peptides at 37° C. At day 4, human IL-2 (20 U/ml) and IL-7 (30 U/ml) were added. The activated CD8 T cells were re-stimulated twice at day 6 and day 14 with either non-CD8 adherent cells in PBMC from same donor (FAA) or Drosophila xAPCs (FFF) in the presence of antigenic peptides. At day 22 the CTLs were harvested and the fold of CD8 T cell expansion was calculated. The antigen-specific CD8 T cells were evaluated by $^{51}$Cr assay. Briefly, $^{51}$Cr labeled M14 (melanoma cell line) cells or peptide-loaded T2 cells were used as targets. The lytic units (LU) were calculated as 100 divided by the E/T ratio at which there is 30% lysis, and the potency was calculated by multiply LU and fold of expansion.
Figure 13:
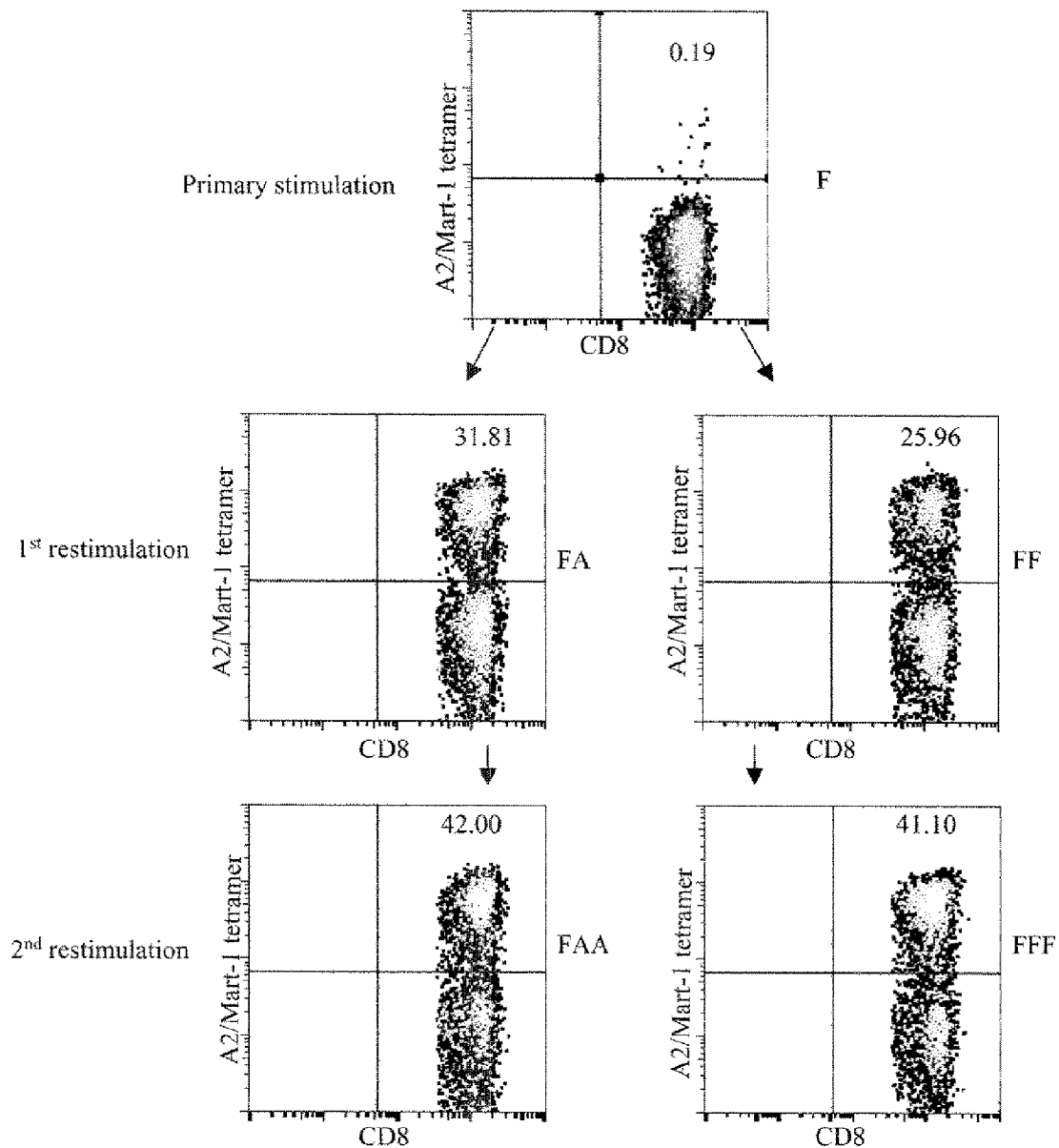
FIG. 13 shows FACS analysis of antigen-specific CTLs with HLA-A2/Mart-1 tetramer. Purified human CD8 T cells from HLA-A2 positive donors were first cultured with Psoralen/UVA treated Drosophila xAPCs preloaded with a mixture of 6 melanoma peptides at 37° C. (F). At day 4, human IL-2 (20 u/ml) and IL-7 (30 u/ml) were added. At day 6 and day 14, the CD8 T cells were restimulated with either psoralen/UVA-treated Drosophila xAPCs once (FF) or twice (FFF) or with non CD8 adherent cells from PBMC of the same donor for once (FA) or twice (FAA). The antigen-specific CD8 T cells were evaluated by staining the cells with anti-CD8 antibody (X-axis) and Mart-1/A2 tetramer (Y-axis) and analyzed by a FACSCanto.
Figure 14:
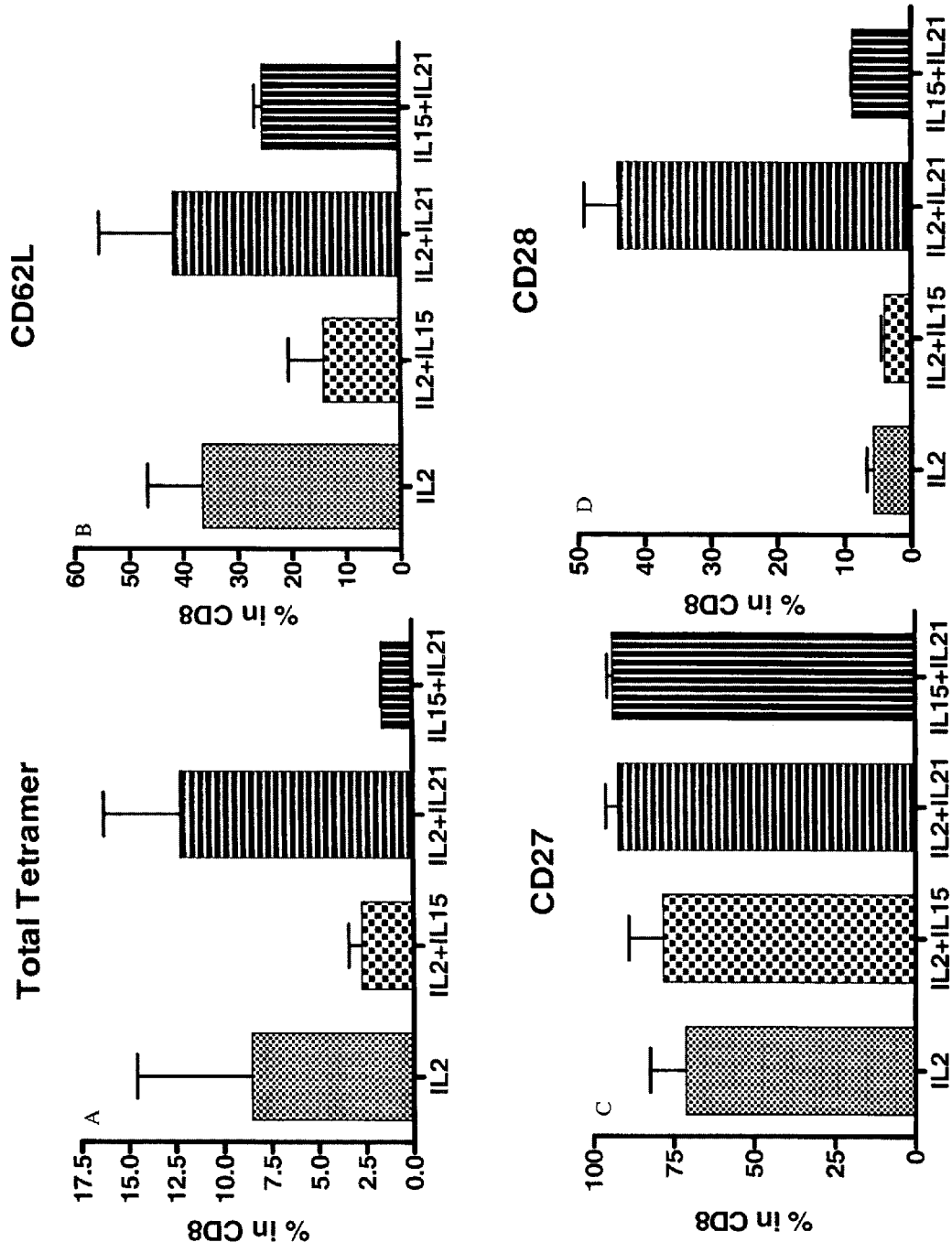
FIG. 14 shows the Comparison of the specific and the phenotypes of the CTLs generated ex vivo with Drosophila xAPCs in the presence of combination of different cytokines. Purified human CD8 T cells from two HLA-A2 positive donors were cultured with Psoralen/UV treated Drosophila xAPCs preloaded with a mixture of 6 melanoma peptides at 37° C. At day 4, human IL-7 (30 U/ml) plus IL-2 (20 U/ml), or IL-7, IL-2 plus IL-15 (25 ng/ml) or IL-7, IL-2 plus IL-21 (25 ng/ml) or IL-7, IL-15 plus IL-21, were added. The activated CD8 T cells were re-stimulated twice at day 6 and day 14 with Drosophila APCs (FFF) in the presence of antigenic peptides and indicated cytokines. The antigen-specific CTLs and the surface markers of the CD8 T cells were evaluated by staining the cells with anti-CD8 antibody and tetramers or indicated antibodies. The data was analyzed by a FACSCanto. The figures shown were the mean of data from two donors.

The PCR method used for detection of *Drosophila* vector-specific DNA sequences is a one-stage polymerase chain reaction that decreases the incidence of false positives in double stranded DNA by limiting the PCR amplification to 25 cycles. Individual PCR tubes containing 400 ng of the test cell therapy product sample DNA in a 5 µL volume is mixed with 45 µL of the PCR master mix containing Platinum Taq polymerase (Invitrogen) and 250 ng of each vector-specific primers. The test and control samples are placed in a GeneAmp PCR system 9700 Thermal Cycler (Applied Biosystems) and the PCR reaction run for 25 cycles. The positive control is total *Drosophila* xAPC DNA, and the negative control is total DNA from the purified naïve CD8+ cells derived from the lymphapheresis product prior to *Drosophila* xAPC stimulation. The size of the positive control PCR fragments are as follows: human beta-2-microglobulin (479 base pairs), human LFA-3 (817 bp), human B7.1 (CD80, 965 bp), human B7.2 (CD86, 1098 bp), human A2.1 (1207 bp) and human ICAM-1 (CD54, 1696 bp) (FIG. 10A, lane 2). Upon completion of the PCR reaction, samples are run on a 2% agarose gel and the results photographed using a UV photodocumentation station. The cell therapy product test sample is considered positive if *Drosophila* xAPC DNA specific bands corresponding to vector inserts are observed (see, e.g., FIG. 10A, lane 2). The specification for cell therapy product is that no *Drosophila*-specific DNA bands are detected and the results are similar to the negative control in this assay.

The sensitivity of detection of *Drosophila* xAPC DNA was determined by spiking two-fold serial dilutions of a known quantity of total *Drosophila* xAPC DNA into 400 ng CD8+ DNA. Plasmid pRMHa-3 vector-specific primers (250 ng each) and Platinum Taq Polymerase (Invitrogen) were added and the volume adjusted to 50 µL with sterile water. After conducting a 25 cycle PCR reaction, 5 uL of 10× gel loading buffer was added to 25 ul of each reaction and run on a 1% low-melt agarose/TAE gel run at 50V for 1 hour. The level lower limit of detection of *Drosophila* DNA was determined to be <50 pg (FIG. 10B, lanes 2-15); therefore sensitivity of detection is in the pictogram range.

Screening of *Drosophila* xAPC-associated Virus in Cell Therapy Product.

As described in EXAMPLE 1, three endogenous insect specific RNA viruses were determined to be associated with the *Drosophila* xAPCs: 1) *Drosophila* Nodavirus (DrNV), 2) *Drosophila* X Virus (DXV), and 3) *Drosophila* HPS-1-like virus. *Drosophila* xAPCs are used to stimulate CD8+ cells at the start of the ex vivo culturing cycle. Therefore, the sample CD8+ cells are tested to confirm the absence of these viruses in the final cell therapy product. Total RNA, purified from cell therapy product cell samples using the Qiagen RNAeasy Kit (Qiagen), is primed with oligo dT and reverse transcribed using Superscript reverse transcriptase for 50 minutes at 42° C. After enzyme inactivation, the resulting cell sample cDNA product is treated with RNaseH for 20 minutes at 37° C. The reaction product is placed on ice. The concentration of CD8+ cDNA is determined by optical density at 260 nm. For the positive controls, virus specific sequences are cloned into plasmid pCR2.1 and plasmid DNA linearized to yield PCR-ready virus specific templates. These plasmids containing virus template of known copy number (20 and 100 viral copies) are also used to spike CD8+ cDNA from cell therapy product samples, which are used as positive controls (see below). Primer sequences used for the detection of virus sequences are as follows:

```
DXV:
Forward
5'-ATCGGTGCTGCCGATGGG-3'            (SEQ ID NO: 74)

Reverse
5'-TGAAGTTCTCATTCTCGTTTGGC-3'       (SEQ ID NO: 75)

Amplicon: 178 bp

DrNV:
Forward
5'-GAGCCGTACGTGATGCCG-3'            (SEQ ID NO: 76)

Reverse:
5'  TCATTGACGGCGAAGTGG 3'           (SEQ ID NO: 77)

Amplicon: 133 bp

HPS-1
Forward:
5'-ATCTTCTGCCCTCCTGGTTT-3'          (SEQ ID NO: 78)

Reverse:
5'-ATTTGCAACCGCATACCTTC-3'          (SEQ ID NO: 79)

Amplicon: 241 bp
```

The level of sensitivity of detecting viral sequences in cDNA preparations of CD8+ samples (spiking experiments) is first determined as follows. Total RNA is purified from CD8+ T cells. The RNA is reverse transcribed with Oligo dT and Superscript III Reverse Transcriptase to yield CD8-specific cDNA. Plasmids containing viral template (DXV, HPS-1 and DrNV) are linearized and quantified by optical density at 260 nm. The number of viral copies per 1 µg of plasmid containing viral template is determined for each virus. The virus-specific primers described above are used in a standard SMART PCR assay with SyBr® Green 1, Hot Start Takara DNA Polymerase and 1 µg of CD8+ cDNA. A range of 10, 100 or 1000 copies of virus template is spiked into the reaction mix in duplicate. Dilutions of virus specific templates (from 20,000 copies to 2 copies) are used to generate the standard curves for real-time quantitative PCR. Virus specific PCR primers are prepared in a SMART PCR assay mix with SyBr® Green 1 and Hot Start Takara DNA Polymerase (Takara). The negative controls include CD8+ cDNA only and primer mix only. Samples are run on the Cepheid SmartCycler PCR system. Melting curve analysis and amplification curve analysis are performed and results recorded in units of SyBr® Green 1 (SyG) detected. The SyG unit is based on the standard curve for each virus titration (Table VII).

TABLE VII

| CD8+ DNA Spike: Level of detection of virus specific sequences in 1 µg of CD8 cDNA[1] | | |
|---|---|---|
| Protocol | Sample ID | SyG unit ($10^{-18}$ g) |
| DXV + CD8+ Spike | CD8+ + 10 copies | 37 |
| | CD8+ + 100 copies | 256 |
| | CD8+ + 1000 copies | 4555 |

TABLE VII-continued

CD8+ DNA Spike: Level of detection of virus specific sequences in 1 μg of CD8 cDNA[1]

| Protocol | Sample ID | SyG unit ($10^{-18}$ g) |
|---|---|---|
| | CD8+ only | 9 |
| | Water only | 22 |
| DrNV + CD8+ Spike | CD8+ + 10 copies | 58 |
| | CD8+ + 100 copies | 333 |
| | CD8+ + 1000 copies | 4919 |
| | CD8+ only | 40 |
| | water only | 54 |
| HPS + CD8+ Spike | CD8+ + 10 copies | 23 |
| | CD8+ + 100 copies | 604 |
| | CD8+ + 1000 copies | 7969 |
| | CD8+ only | 0 (below 10 ag std) |
| | Water only | 0 (below 10 ag std) |

[1]To 1 μg of CD8+ cDNA (CD8+), known amounts of viral template are added. The detection of 10-100 copies of each viral template per μg of CD8+ cDNA is attainable for all three viruses.

For the cell therapy product release assay, test samples include, in triplicate, 200 ng of CD8+ cDNA at Day=0 and 200 ng of CD8+ cDNA derived from cell therapy product test samples. The positive control samples include, in triplicate, 200 ng CD8+ cDNA spiked with 20 and 100 copies of virus template. The negative control samples contain the PCR mix only (no template). All samples are run on the Cepheid SMART Cycler System. Melt curve analysis and amplification curve analysis is performed for each of the three viral PCR assays. Positive controls will give specific melting curves and SyBr® Green 1 values above background (CD8+ cDNA at Day=0). The specification for cell therapy product release is that no *Drosophila* virus-specific amplification above that observed kin negative controls is detected.

Table VIII depicts the representative results of assays performed in triplicate obtained from the real-time quantitative PCR assay for identified adventitious viruses in naive (i.e., prior to activation with xAPCs, as described above) and cell therapy product samples from four patient donors (PD1, PD2, PD3, and PD4). The results show that each tested cell therapy product (Final Dose) tested negative for each virus assayed (i.e., SyG units in each Final Dose was less than the SyG units for each corresponding naïve sample).

TABLE VIII

Multiple Naïve (non-activated) and Cell Therapy Product Samples Evaluated with Real-Time Quantitative PCR (SyG Units)[1].

| Sample | PD1 | PD2 | PD3 | PD4 |
|---|---|---|---|---|
| HPS-1 | | | | |
| H₂O | 0 | 0 | 0 | 0 |
| Naïve Sample | 0 | 0 | 0 | 0 |
| Final Dose | 0 | 0 | 0 | 0 |
| Final Dose – 20 copies | 35 | 73 | 88 | 49 |
| Final Dose – 10 copies | 230 | 263 | 314 | 443 |
| DrNV | | | | |
| H₂O | 0 | 0 | 0 | 0 |
| Naïve Sample | 4 | 31 | 7 | 4 |
| Final Dose | 5 | 3 | 5 | 6 |
| Final Dose – 20 copies | 94 | 112 | 63 | 120 |
| Final Dose – 100 copies | 566 | 349 | 450 | 431 |
| DXV | | | | |
| H20 | 0 | 0 | 0 | 0 |
| Naïve Sample | 0 | 0 | 0 | 0 |
| Final Dose | 0 | 0 | 0 | 0 |
| Final Dose – 20 copies | 87 | 64 | 91 | 96 |
| Final Dose – 100 copies | 344 | 319 | 320 | 381 |

[1]To 0.2 ug of CD8 cDNA, known amounts of viral template are added. The detection of 20-100 copies of each viral template per μg of CD8 cDNA is attainable for all three viruses.

Tables IX and X depict representative results from assays in duplicate on samples obtained from normal donor 1 (ND1). In Table IX, 0.2 μg of CD8+ cDNA was assayed. In Table X, 3.0 μg of CD8+ cDNA was assayed. The results shown in Tables IX and X show that each tested cell therapy product (ND1 Dosed CD8+) tested negative for each virus assayed (i.e., SyG units in each Final Dose was less than the SyG units for each corresponding naïve sample). Data for HPS shown only in assay depicted in Table X, as the supply of CD8+ cDNA is exhausted in this single assay. However, routine screening of cell therapy product cDNA samples at this concentration would consume all the sample and possibly prevent completion of all required tests and not allow for repeat assays.

TABLE IX

Quantitative RT/PCR of Normal Donor 1 (ND1) naïve and dosed CD8+ cells with viral specific primers[1]

| Sample | HPS (SyBr) | DXV (SyBr) | DrNV (Sy Br) |
|---|---|---|---|
| ND1 Naive CD8+ | 0 | 9 | 0 |
| ND1 Dosed CD8+ | 0 | 0 | 0 |
| ND1 Dosed CD8+ + 20 copies | 115 | 77 | 67 |
| ND1 Dosed CD8+ + 100 copies | 547 | 286 | 466 |
| Primer Mix only | 0 | 0 | 0 |

[1]Each sample (0.2 μg) was run in duplicate in a standard SMART PCR assay with virus specific primers.

TABLE X

Quantitative RT/PCR of Normal Donor 1 (ND1) naïve and dosed CD8+cells with HPS viral specific primers[1]

| Sample | HPS (SyBr) | DXV (SyBr) | DrNV (SyBr) |
|---|---|---|---|
| ND1 Naive CD8 | 0 | ND* | ND* |
| ND1 Dosed CD8 | 0 | ND* | ND* |
| ND1 Dosed + 20 copies | 89 | ND* | ND* |
| ND1 Dosed + 100 copies | 361 | ND* | ND* |
| Primer Mix only | 0 | ND* | ND* |

[1]Each sample (3 μg) was run in duplicate in a standard SMART PCR assay with HPS virus specific primers.
*ND: Not determined (see above).

Utilizing the PCR reactions described above, the *Drosophila* viral-specific primers are used to screen the CD8+ preparations from cell therapy product samples at the end of the ex vivo culturing process for release of future lots of cell therapy product. Each of the viral PCR reactions are performed on cDNA isolated from fresh *Drosophila* cells (positive control), cDNA prepared from CD8+ sample that has never been exposed to the *Drosophila* cells (negative control) and the final CD8+ product that is evaluated during the release testing of a cell therapy product dose. Virus specific product detectable in the positive control is absent in the CD8+ samples collected prior to exposure to *Drosophila* cells and in the cell therapy product in order for the cell therapy product to be released.

Cell Therapy Product Phenotype and Activity Assays.

The biological characteristics of the cell therapy product are assessed by measurements of total cell number, viability, phenotype, and potency. Additionally, in-process assessments of viable cell number, phenotype, CD8+ and non-CD8+ selected cell composition throughout the cell therapy product manufacturing process are performed.

Viable Nucleated Cell Number.

The number of viable cells is monitored at several points in the cell therapy product manufacturing process including the point prior to cell therapy product release. Viable cells counts are determined by enumerating cells diluted in trypan blue and loaded onto a hemocytometer (see, e.g., above). A minimum of 100 cells are counted under a microscope. Table XI summarizes the cell numbers recorded for lymphapheresis products obtained from three melanoma patient donors, designated PD5, PD6, and PD7, and associated cellular materials at various steps in the cell therapy product manufacturing and release testing processes.

TABLE XI

Cell numbers for lymphapheresis products, associated cellular material, and cell therapy products derived from patient donors PD5, PD6, and PD7

| Approx. day of process | Cell Fraction | Cell Number (×10$^6$ nucleated cells) | | | | |
|---|---|---|---|---|---|---|
| | | PD5 | PD6 | PD7 | Mean | Std. Dev. |
| 0 | Lymphapheresis product (total nucleated cell count) | 16,000 | 14,000 | 6,630 | 12,210 | 4,934 |
| | Selected CD8+ Cells | 510 | 464 | 313 | 429 | 103 |
| | Selected Non-CD8+ Cells Post Ficoll Processing | 5,400 | 11,400 | 4,200 | 7,000 | 3,857 |
| | Culture initiation (peptide specific stimulation), number of CD8+ used for manufacture | 485 | 438 | 290 | 404 | 102 |
| 6 | Cells at 1$^{st}$ Restimulation | 300 | 299 | 410[a] | 336 | 64 |
| 15 | Cells at 2$^{nd}$ Restimulation | 701[a] | 306 | 390[a] | 466 | 208 |
| 20 | Cells at OKT3 Expansion | 520 | 420 | 370 | 437 | 76 |
| | Fold Expansion (Day 0 initiation-Day 20 ± 1) | 2.50 | 0.96 | 1.74 | 1.73 | 0.77 |
| | Culture initiation (non-specific expansion) number of CD8+ used for OKT3 stimulation | 400 | 400 | 370 | 390 | 17 |
| 30 | Cell therapy (Final) Product | 10,000 | 9,600 | 10,300 | 9,966 | 351 |
| | Fold Expansion Day 30 ± 1 cell count ÷ Day 20 cell count (Day 20 ± 1 initiation-Day 30 ± 1) | 25 | 24 | 27.8 | 25.6 | 1.97 |

[a] Only 300 × 10$^6$ cells were re-stimulated.

The number of total nucleated cells in a cell therapy product for release is between $9^9$ and $10^{10}$ cells.

Cell Viability.

Cell viability is assessed by counting cells diluted in trypan blue solution on a hemocytometer as described above. The percent of viable cells, based on the ratio of live cells to total cells present, is calculated. Table XII presents the viability of six cell therapy product lots prepared from lymphapheresis products obtained from six melanoma patient donors, designated PD8, PD6, PD9, PD5, PD7, and PD10. The mean viability was 76.2%, with a standard deviation of ±2.6 (n=6). The cell therapy product current manufacturing process routinely yields ≧70%. A cell therapy product possesses greater than 70% viability based on this assay method in order for the cell therapy product to be released.

TABLE XII

Cell viability for six cell therapy product lots

| Lot | Viability |
| --- | --- |
| -PD8 | 76% |
| PD6 | 72% |
| PD9 | 80% |
| PD5 | 74% |
| PD7 | 78% |
| PD10 | 77% |

Cell Therapy Product Phenotype.

Cell phenotype and CD8+ purity is determined by cell surface staining with fluorescent-labeled monoclonal antibodies and analyzed by flow cytometry. Two-color analysis on the FACScan flow cytometer is performed according to the panel of monoclonal antibodies listed below. Markers for product characterization include: CD3 (T lymphocytes), CD4 (T helper cells), CD8 (T cytotoxic cells), CD14 (monocytes), CD19 (B cells), CD16 (NK cells), and CD15 (granulocytes). Cells used for flow cytometry testing are washed in FACS buffer (PBS containing BSA and sodium azide) and incubated with the appropriate fluorescent-labeled monoclonal antibodies at 4° C. for 15-30 minutes, protected from light. Post incubation, the stained cells are washed and resuspended in FACS buffer. Stained cells are stored on ice, protected from light, and run on the flow cytometer within two hours of staining. Alternatively, if the samples cannot be analyzed within two hours, the samples are fixed using a solution of 0.5% paraformaldehyde in DPBS and stored for a week at 4° C. in the dark. A total of 10,000 events are collected for each sample. Data is analyzed and the percentage of cells that are positive for each marker is determined. Table XIII depicts the percentage of CD3+ and CD8+ cells present in six cell therapy product lots, derived from lymphapheresis products obtained from melanoma patient donors PD8, PD6, PD9, PD5, PD7, and PD10. The fraction of cells not stained with CD3+ and CD8+ are believed to be non-viable cells. These data suggest that the relative percentage of CD3+ and CD8+ phenotypes in different cell therapy product lots remains relatively consistent (see, e.g., mean percentages and standard deviations in Table XIII.)

TABLE XIII

Phenotype analysis for cell therapy product lots from melanoma patient donors

| Patent Donor | % CD3+ | % CD8+ |
| --- | --- | --- |
| PD8 | 81 | 89 |
| PD6 | 75 | 86 |
| PD9 | 77 | 76 |
| PD5 | 77 | 82 |
| PD7 | 80 | 82 |
| PD10 | 78 | 80 |
| Mean % | 78 | 82.5 |
| Std. Dev. | 2.0 | 4.2 |

To assess the purity of CD8+ cells before and after the Isolex-300i selection procedure, cell surface staining with fluorescent labeled monoclonal antibodies is performed and analyzed by flow cytometry as described above. Table XIV depicts the phenotype distribution of lymphapheresis products and corresponding therapy product lots derived from melanoma patient donors DP8, PD6, and PD9. Isolation of CD8+ cells, using the Isolex cell separator, resulted in 82±9% (mean±SD, n=3) purity, based on staining with anti-CD8 monoclonal antibody 37B1A. There were detectable levels of CD4+ (3±1.4%), CD14+ (2±1.5%), and CD16+ (5±2%) cells. This cell population appeared to be devoid of CD15+ cells.

TABLE XIV

Cell phenotype distribution for lymphapheresis products and corresponding cell therapy product lots derived from melanoma patient donors PD8, PD6, and PD9

| Sample | Cell Surface Marker | PD8 | PD6 | PD9 | Mean | Std. Dev. |
| --- | --- | --- | --- | --- | --- | --- |
| Lymphapheresis Product | % CD3+ | 30 | 54 | 45 | 43 | 8.6 |
| | % CD4+ | 41 | 42 | 31 | 38 | 4.3 |
| | % CD8+ | 10 | 7 | 14 | 10 | 2.5 |
| | % CD14+ | 22 | 14 | 17 | 18 | 2.9 |
| | % CD19+ | 7 | 4 | 10 | 7 | 2.1 |
| | % CD15+ | 5 | 1 | 3 | 3 | 1.4 |
| | % CD16+ | 7 | 22 | 16 | 15 | 5.3 |
| CD8+ Selected Population (Isolex Separation) | % CD3+ | 95 | 87 | 80 | 87 | 5.3 |
| | % CD4+ | 5 | 3 | 1 | 3 | 1.4 |
| | % CD8+ | 94 | 83 | 69 | 82 | 10.2 |
| | % CD14+ | 4 | 0 | 1 | 2 | 1.5 |
| | % CD19+ | 7 | 2 | 2 | 4 | 2.0 |
| | % CD15+ | 0 | 1 | 0 | 0 | 0.4 |
| | % CD16+ | 7 | 6 | 1 | 5 | 2.3 |

Cell Therapy Product Potency.

A cell therapy potency assay is performed to demonstrate specific lytic activity as a measure of potency of the cell therapy product against target cells that have been loaded with selected peptides (e.g., peptides according to SEQ ID NOS:5, 6, 7, 8, 9, and 70, as described above). The cell therapy potency assay method is a $^{51}$Cr-release assay (see, e.g., Thorn et al., *J. Immunol. Methods.*, 4(2), pp. 301-315 (1974)). Target cells (T2 cells-HLA-A2.1+) are incubated with the radioactive isotope, $^{51}$Cr, for one hour. Excess unlabeled $^{51}$Cr is washed twice from the target cells in wash medium. Individual chromium-loaded T2 cell samples are then peptide-loaded for 30 minutes at room temperature (20 μg/mL per peptide) with one of the six melanoma peptides (such that each target peptide is individually tested using an independent sample of chromium-loaded T2 cells), peptide-loaded a negative control peptide, or not peptide-loaded. Cell therapy product cells (i.e., peptide-loaded xAPC-induced CD8+ effector cells (E)) are then mixed with labeled target cells (T) at E:T ratio between 0.4-50 along with excess unlabeled K562 cells used to neutralize non-HLA restricted cytotoxicity. The cell suspension is incubated at 37° C./5% $CO_2$ in an incubator for four hrs. Lysis of labeled target cells by cell therapy product cells (E) results in release of $^{51}Cr$ into the supernatant. Post incubation, 100 μL of cell supernatant is removed from each well and transferred to a gamma counter. Lytic activity (E) in the presence of each individual peptide is expressed as percentage specific lysis as determined by the following equation (refer to equation:

percentage specific lysis=100×(sample counts per minute−spontaneous counts per minute)/(maximum counts per minute−spontaneous counts per minute).

In addition to peptide-loaded T2 cells, melanoma and negative control cell lines are also used as targets after being loaded with chromium. The assay procedure remains the same as the procedure used with T2 target cells. Specific lysis is detected in either T2 and/or melanoma lines for product to be released.

The potency results (percentage specific lysis at a 10:1 E:T ratio) for six cell therapy product lots derived from lymphapheresis products obtained from melanoma patient donors PD8, PD6, PD9, PD5, PD7, and PD10 against each of SEQ ID NOS:5, 6, 7, 9, and 70 are summarized in Table XV.

TABLE XV

Cell therapy product potency ($^{51}Cr$-release assay; n = 6)

| Dose | SEQ ID NO: 5 | SEQ ID NO: 6 | SEQ ID NO: 7 | SEQ ID NO: 9 | SEQ ID NO: 70 | Negative Control |
|---|---|---|---|---|---|---|
| PD8 | 15.8% | 9.6% | 45.7% | 18.1% | 25.8% | 3.8% |
| PD6 | 30.7% | 3.5% | 14.6% | 26.6% | 18.0% | 0.0% |
| PD9 | 7.0% | 5.7% | 10.9% | 75.4% | 11.9% | 4.7% |
| PD5 | 29.0% | 8.5% | 20.6% | 21.1% | 21.3% | 0.2% |
| PD7 | 39.4% | 25.5% | 85.6% | 16.5% | 47.2% | 9.6% |
| PD10 | 26.6% | 17.9% | 78.7% | 50.1% | 33.3% | 0.9% |
| Mean | 24.8% | 11.8% | 42.7% | 34.6% | 26.3% | 3.2% |
| Std. Dev. | 10.5% | 7.6% | 30.1% | 21.4% | 11.5% | 3.4% |

In a similar analysis, one peptide (SEQ ID NO:8; YLEPGPVTA) was added to the five peptides already used to generate killing activity in the cell therapy product. The ability of SEQ ID NO:8, used alone or combined with other melanoma peptides to generate specific lysis activity, was demonstrated in three normal donors, as described in Table XVI.

TABLE XVI

Potency (measured in lytic units) of effector cells from three normal donors (ND2, ND3, and ND4) against melanoma peptides

| T2 + Peptide (SEQ ID NO:) | ND2 | ND3 | ND4 |
|---|---|---|---|
| 5 | 16.8 | 12.9 | 17.2 |
| 6 | 7.5 | 18.3 | 2 |
| 7 | 5.2 | 14.1 | 39.4 |
| 8 | 1.6 | 15.7 | 18.3 |
| 70 | 23.3 | 13.5 | 24.7 |
| 9 | 31.8 | 59.3 | 37.9 |
| 5 + 6 + 7 + 8 + 9 + 70 | 93.8 | 122.4 | 103.4 |
| 8* | 75.2 | 61.5 | 72.1 |

*cell therapy product generated against SEQ ID NO: 8 alone.

Preparation of Product for Infusion

In order to harvest cell therapy product cells and prepare a cell therapy product formulation, the cell suspension prepared above is homogenized by each bag immediately prior to harvest. Two Fenwal spike/spike Plasma Transfer Sets (closed clamps) are then spiked to the unused ports on each Lifecell® bag. Each bag is hung on a hook elevated from the surface of the biosafety cabinet. The clamps on the Plasma Transfer Sets are opened, and the cell suspensions are drained into two sterile Nalgene bottles (1000 ml and 500 ml). Each bag is handled separately. After transferring the cell suspensions, 5 ml of each cell suspension from each Lifecell bag is sampled from each 1000 ml Nalgene bottle and placed in a separate T25 flask. Cells in each of the four T25 flasks are visually checked for unusual color or cloudiness, and microscopically inspected for possible contamination. Cells from corresponding Lifecell® bag of any contaminated samples are discarded. Uncontaminated cells from the four T25 flasks are pooled and counted after dilution at 1:4 with trypan blue (50 μl cell sample+150 μl trypan blue). A viable cell count is then determined. Approximately $10\times10^6$ cells are set aside to be used for FACS analysis. The remaining cell suspension is poured into sterile 500 ml conical tubes. The tubes are then weighed and balanced by adding or removing cell suspension in the biosafety cabinet (hood), and the cells are then pelleted by centrifugation for 10 minutes at 1,700 rpm (600×g). The supernatants are decanted and discarded, and the pellets centrifuged again for two minutes at 2,000 rpm (800×g). Any remaining supernatant is removed with a 5 ml pipette.

Pelleted cells are then washed with the following wash buffer, which is mixed in a sterile 250 ml bottle: 192 ml 0.9% Sodium Chloride (NaCl) for Injection, USP, and 8 ml HSA (25% solution) Buminate®. All cell pellets are combined in a total of 100 ml of wash buffer, distributed in four 50 ml conical tubes (25 ml/tube) and centrifuged for 10 minutes at 1,000 rpm (200×g). The supernatants are aspirated and discarded, and the cell pellets are again centrifuged for two minutes at 2,000 rpm (800×g). Any remaining supernatant is removed using a fine tip pipette. Each cell pellet is then resuspended in 25 ml of wash buffer and centrifuged for 10 minutes at 1,000 rpm (200×g). The supernatants are aspirated and discarded, and the cell pellets are again centrifuged for two minutes at 2,000 rpm (800×g). Any remaining supernatant is removed using a fine tip pipette. During this second low speed centrifugation, a 1,000 ml transfer pack (Baxter; catalog number 4R2032) is sealed and the tubing discarded. The transfer bag is then fitted with a plasma transfer set (Charter Medical; catalog number 03-220-90), and patient identification information is affixed to the transfer bag. Each cell pellet is then resuspended with 25 ml of the following resuspension buffer (100 ml total volume), which is prepared in the following in a sterile bottle: 282 ml Ringers lactated medium, 12 ml 5% dextrose and 0.9% sodium chloride for injection, and 6 ml HSA (25% solution) Buminate®. The resuspension buffer is pipetted thoroughly to separate clumped cells. A 70 μm nylon sterile cell strainer (Falcon 2350) is then placed over the opening of a sterile 100 ml Nalgene bottle. Cell aggregates are removed from the cell suspension by passing it through the cell strainer. The cell strainer is then discarded. Viable and dead cells are then counted after dilution at 1:50 with Trypan Blue (20 μl cells+980 μl Trypan Blue).

A 60-ml luer-lock is attached syringe to the plasma transfer set which was attached to the 1000 ml transfer bag, and a volume of cell suspension equivalent to a maximum of $1\times10^{10}$ cells is transferred into the transfer bag. Resuspension Buffer is then added to the transfer bag to a total volume of 246 ml. All unused portions of resuspension buffer are discarded.

Next, the cell suspension is homogenized by swirling the bag, and 0.5 ml of cell suspension is withdrawn from the bag using a 3 ml syringe attached to the plasma transfer set. This 0.5 ml sample is placed in a sterile Eppendorf tube for use in endotoxin testing (0.15 ml needed), as described above.

Using a 60 ml syringe, 54 ml HSA (25% solution) Buminate® is added to the bag through the plasma transfer set. The new cell concentration is then calculated by dividing the total cell number by the new cell volume. The cell suspension is again homogenized by swirling the bag. Using a 10 ml syringe attached to the plasma transfer set, 6.5 ml of cell suspension is withdrawn from the bag. This sample is to be used for release testing and for cell cryopreservation. Approximately 0.1 ml (2-3 drops) of cell suspension from the 6.5 ml sample is placed in a sterile Eppendorf tube for Gram staining as described above. A 0.5 ml aliquot of cell suspension is placed in a sterile 15 ml conical tube for FACS analysis. The remaining cell sample is transferred to a 15 ml conical tube and centrifuged for seven minutes at 1,700 rpm (600×g). The supernatant is used immediately for BacT/Alert sterility testing, and the pellet is saved for FACS analysis and cryopreservation. The number of cells present in the pellet is calculated, and the cell pellet is resuspended in 6.0 ml of freezing solution (90% autologous serum [HIAS]+10% DMSO). The cell concentration is then calculated by dividing the cell number in the pellet by 6.0 ml. Cryotubes are then labeled appropriately and frozen. The cryotubes are then placed in a −80° C. freezer in a Stratacooler and then transferred to −140° C. storage the following day. The bags containing remaining cell suspension are placed at 4° C. until ready to release (ship).

The cell therapy product formulation for infusion contains autologous CTLs (selected peptide-directed CD8+ effector cells) in 300 mL Lactated Ringer's Injection, USP (76% v/v), 5% Dextrose in 0.9% Sodium Chloride (4% v/v) and 25% Human Serum Albumin (20% v/v). At the time of shipment, a Dickson temperature logging apparatus is placed in the shipping container. The infusion bag containing the cell therapy product is placed in the shipping container. The shipping container is then prepared for shipping. After the infusion bag is received from the clinical site, the temperature data from the Dickson temperature logging apparatus is downloaded and graphed. The final product expiry period is 42 hours.

DISCUSSION

Crosslinking provides an effective method for elimination of virus and maintenance of antigen presentation function in aAPCs. The use of psoralen followed by long-wave UV exposure crosslinks DNA and RNA and prevents replication. This adds an additional level of protection to cell-based products used in the preparation of drugs for delivery to patients, by potentially inactivating all known and unknown viruses that could be present in the aAPC cell line and inactivating the *Drosophila* cell line without affecting its potent APC function. The psoralen/UV treatment inactivates the nucleic acids present in the APCs and an additional freeze/thaw treatment results in "dead" cells as evident by staining with trypan blue. This inactivation/lysis protocol ensures the safety of the *Drosophila* cells as APCs without destroying, and in some cases enhancing, its APC function.

Although the invention has been described in detail above in reference to illustrative examples and preferred embodiments, the artisan will understand that the scope of the invention is defined not by the foregoing description, but by the appended claims as properly construed under principles of patent law.

What is claimed is:

1. A method for creating activated T lymphocytes ex vivo for administration to a patient, comprising the steps of:
   inactivating artificial antigen presenting cells (aAPCs) with a photoactivatable crosslinking agent, wherein the photoactivatable crosslinking agent consists of the psoralen family of molecules and derivatives thereof, such that the inactivated aAPCs are essentially nonviable and retain the antigen-presenting function;
   contacting T lymphocytes isolated from a patient diagnosed with a disease or disorder with said inactivated artificial antigen presenting cells; and
   collecting the T lymphocytes for administration back to the patient.

2. A method as defined in claim 1, wherein the photoactivatable crosslinking agent is a psoralen derivative and said inactivating step comprises exposing the artificial antigen presenting cells treated with the psoralen derivative to a photoactivating dose of UVA irradiation.

3. A method as defined in claim 2, wherein said psoralen derivative is psoralen, 8-methoxypsoralen (8-MOPS), 4'-(aminomethyl)-4,5',8-psoralen (AMT), or amotosalen (S59).

4. A method as defined in claim 1; wherein the photoactivatable crosslinking agent is a psoralen derivative and said inactivating step comprises exposing the artificial antigen presenting cells treated with the psoralen derivative at a concentration of from 1 to 25 µg/ml to UVA irradiation at a dose of from 1 to 100 Joule/cm$^2$ UVA irradiation for a period of from 1 to 60 minutes.

5. A method as defined in claim 1, wherein said disease or disorder is a cancer, and further comprising prior to or concomitant with said contacting step:
   loading the artificial antigen presenting cells with at least one cancer-associated peptide antigen.

6. A method as defined in claim 5, wherein said activated T lymphocytes are cytotoxic toward target cells expressing the peptide, and the peptide is selected from the group consisting of melanoma cancer-associated peptide antigens, ovarian cancer-associated peptide antigens, breast cancer-associated peptide antigens, lung cancer-associated peptide antigens, leukemia-, multiple myeloma- and lymphoma-associated peptide antigens, and prostate cancer -associated peptide antigens.

7. A method as defined in claim 6 wherein said peptide comprises at least eight contiguous antigenic amino acids of the amino acid sequence of MART-1, tyrosinase, gp100, NY-ESO-1, MUC-1, CA-125, Her-2, survivin, telomerase, CAMEL, CEA, livin, SART-1, SCP-1, SSX-2, PRAME, C-Lectin, Pec60, AES, MAGE-3, G250, FBP, SSX-4, SP17, hTRT, MUC-16, MAGE-1, Topoisomerase II, Integrin β8 subunit precursor, MUC-1, MAGE -B2, STAT 1, γ-Catenin, or H-RYK.

8. A method as defined in claim 7 wherein said peptide comprises an amino acid sequence selected from the group consisting of: SILSLKEAST (SEQ ID NO:1), KMASRSMRL (SEQ ID NO:2), ALALAALLVV (SEQ ID NO:3), ALLVVDREV (SEQ ID NO:4), YMNGTMSQV (SEQ ID NO:5), YMDGTMSQV (SEQ ID NO:6), ITDQVPFSV (SEQ ID NO:7), YLEPGPVTA (SEQ ID NO:8), AAGIGILTV (SEQ ID NO:9), ELAGIGILTV (SEQ ID NO:10), CLTSTVQLV (SEQ ID NO:11), HLYQGCQVV (SEQ ID NO:12), KIFGSLAFL (SEQ ID NO:13), IISAVVGIL (SEQ ID NO:14), PLTSIISAV (SEQ ID NO:15), VMAGVGSPYV (SEQ ID NO:16), VLVKSPNHV (SEQ ID NO:17), ELVSEFSRM (SEQ ID NO:18), YLSGANLNL (SEQ ID NO:19), GPLTPLPV (SEQ ID NO:20), SLLMWITQC (SEQ ID NO:21), KALFAGPPV (SEQ ID NO:22), YLETFREQV (SEQ ID NO:23), GLQSPKSPL (SEQ ID NO:24), VLLKLRRPV (SEQ ID NO:25), ELYIPSVDL (SEQ ID NO:26), SLLMWITQV (SEQ ID NO:27), ILAKFLHWL (SEQ ID NO:28), STAPPVHNV (SEQ ID NO:29), FLWGPRALV (SEQ ID NO:30), FMWGNLTLA (SEQ ID NO:31), RLVDDFLLV (SEQ ID NO:32), HLSTAFARV (SEQ ID NO:33), QLSLLMWIT (SEQ ID NO:34), ELWTHSYKV (SEQ ID NO:35), KVAELVHFL (SEQ ID NO:36), YIFATCLGL (SEQ ID NO:37), HLYIFATCL (SEQ ID NO:38), MLMAQEALAFL (SEQ ID NO:39), STLEKINKT (SEQ ID NO:40), KASEKIFYV (SEQ ID NO:41), SLLMWITQCFL (SEQ ID NO:42), ELTLGEFLKL (SEQ ID NO:43), LTLGEFLKL (SEQ ID NO:44), SLLEKREKT (SEQ ID NO:45), TLGEDDPWL (SEQ ID NO:46), KLGLKPLEV (SEQ ID NO:47), YLWTSAKNT (SEQ ID NO:48), STAPPAHGV (SEQ ID NO:49), GMGSEELRL (SEQ ID NO:50), SLGSPVLGL (SEQ ID NO:51), YLFFYRKSV (SEQ ID NO:52), CQQEETFLL (SEQ ID NO:53), TLAKFSPYL (SEQ ID NO:54), NLTHVLYPV (SEQ ID NO:55), STFKNWPFL (SEQ ID NO:56), SLLQHLIGL (SEQ ID NO:57), FLDQRVFFV (SEQ ID NO:58), FLDQRVFVV (SEQ ID NO:59), FLDQVAFVV (SEQ ID NO:60), GLDREQLYL (SEQ ID NO:61), VMQHLLSPL (SEQ ID NO:62), QQTHGITRL (SEQ ID NO:63), LQPLSGPGL (SEQ ID NO:64), TLDRDSLYV (SEQ ID NO:65), QLYLELSQL (SEQ ID NO:66), KVLEYVIKV (SEQ ID NO:67), KVADLVGFL (SEQ ID NO:68), and KTWGQYWQV (SEQ ID NO:70).

9. A method as defined in claim 8 wherein said at least one peptide is a mixture of peptides, the mixture comprising: YMNGTMSQV (SEQ ID NO:5), ITDQVPFSV (SEQ ID NO:7), AAGIGILTV (SEQ ID NO:9), ELAGIGILTV (SEQ ID NO:10), SLLMWITQV (SEQ ID NO:27), FLWGPRALV (SEQ ID NO:30), and TLAKFSPYL (PRAME; SEQ ID NO:54).

10. A method as defined in claim 2 further comprising:
   isolating T cells from a pheresis sample from a patient for use in said contacting step; and
   administering to the subject an effective amount of the T lymphocytes collected in said collecting step.

11. A method as defined in claim 10 further comprising restimulating said activated T lymphocytes prior to performing said administering step, said restimulation procedure comprising:
   contacting the activated T lymphocytes with at least one cytokine, thereby promoting activated T cell proliferation; and
   incubating the activated T cells with irradiated autologous non-CD8+ cells, adherent nonCD8$^+$ cells or Psoralen/UVA treated artificial antigen presenting cells (aAPCs), thereby generating restimulated activated T lymphocytes.

12. A method as defined in claim 11, wherein said at least one cytokine is selected from the group consisting of IL-2, IL-4, IL-7, IL-12, IL-15, IL-17, IL-21, IFN-γ, and TNF-α, and wherein said activated T lymphocytes comprise activated cytotoxic T lymphocytes.

13. A method as defined in claim 11 further comprising subjecting said activated T lymphocytes to at least one iteration of a restimulation procedure prior to performing said generating step, said restimulation procedure comprising:
   contacting the activated T lymphocytes with a combination of IL-2 and at least one other cytokine selected from the group consisting of :IL-7, IL-15 or IL-21 thereby promoting activated T cell growth, proliferation, or differentiation; and incubating the activated T cells with irradiated autologous non CD8+ cells or adherent nonCD8+ cells or Psoralen/UVA treated aAPCs to generate restimulated T lymphocytes.

14. A method as defined in claim 13, where said restimulation procedure comprises contacting the activated T lymphocytes with *Drosophila* aAPCs in the presence of IL-2 at a concentration of from 1 to 100 U/ml; IL-7 from 1 to 100 U/ml, IL-15 from 1 to 100 ng/ml and IL-21 from 1 to 100 ng/ml.

15. A method as defined in claim 13, wherein said irradiated autologous adherent nonCD8+ cells comprise irradiated autologous adherent CD14+ cells.

16. A method as defined in claim 13, where said irradiated autologous non CD8+ cells comprise irradiated autologous CD4+ T cells.

17. A method as defined in claim 2, further comprising:
freezing and thawing said artificial antigen presenting cells prior to, subsequent to, or concomitant with said inactivating step and prior to said contacting step.

18. A method as defined in claim 2, wherein the inactivated artificial antigen presenting cells are incapable of proliferation and are essentially free of contamination.

19. A method as defined in claim 2, wherein said artificial antigen presenting cells express a human leukocyte MHC antigen molecule β-2 microglobulin, and an assisting molecule comprising a co-stimulatory molecule selected from the group consisting of human CD80(B7-1), LFA-3(CD58), CD83, and CD86(B7.2), or the TNF family member CD70, or an adhesion molecule selected from the group consisting of ICAM-1, ICAM-2, ICAM-3 and LFA -3.

20. A method as defined in claim 19, wherein said artificial antigen presenting cells express the human HLA class I MHC antigen molecule HLA 2.1.

21. A method as defined in claim 20 wherein the class I MHC molecule is HLA-A2.1, and the assisting molecules are B7-1 (CD80), LFA-3(CD58), CD70 and ICAM-1(CD54).

22. A method as defined in claim 19, where said psoralen/UVA treated aAPCs comprise *Drosophila* cells transfected with HLA molecules and costimulation molecules.

23. A method as defined in claim 1, wherein said disease, disorder, or medical condition is a cancer selected from the group consisting of malignant melanoma, multiple myeloma, prostate cancer, lymphoma, non-Hodgkin's lymphoma, leukemia, acute lymphoblastic leukemia, acute myeloid leukemia, chronic lymphocytic leukemia, chronic myeloid leukemia, Burkitt's lymphoma, thyroid cancer, uterine cancer, kidney cancer, ovarian cancer, lung cancer, breast cancer, liver cancer, pancreatic cancer, prostate cancer, colon cancer, skin cancer, stomach cancer, cervical cancer, head and neck cancer, glioma, and brain cancer.

24. A psoralen-inactivated artificial antigen presenting cell expressing HLA-A2.1, B7-1 (CD80), LFA-3(CD58), CD70 and ICAM-1(CD54) cell surface protein and presenting the following peptides YMNGTMSQV (SEQ ID NO:5), ITDQVPFSV (SEQ ID NO:7), AAGIGILTV (SEQ ID NO:9), ELAGIGILTV (SEQ ID NO:10), SLLMWITQV (SEQ ID NO:27), FLWGPRALV (SEQ ID NO:30), and TLAKFSPYL (SEQ ID NO:54).

\* \* \* \* \*

SEQUENCE LISTING

```
<160> NUMBER OF SEQ ID NOS: 83

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Ile Leu Ser Leu Lys Glu Ala Ser Thr
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Met Ala Ser Arg Ser Met Arg Leu
1               5

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
```

-continued

```
       peptide

<400> SEQUENCE: 3

Ala Leu Ala Leu Ala Ala Leu Leu Val Val
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Leu Leu Val Val Asp Arg Glu Val
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Met Asn Gly Thr Met Ser Gln Val
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Met Asp Gly Thr Met Ser Gln Val
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ile Thr Asp Gln Val Pro Phe Ser Val
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Tyr Leu Glu Pro Gly Pro Val Thr Ala
1               5

<210> SEQ ID NO 9
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Ala Gly Ile Gly Ile Leu Thr Val
1               5

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Glu Leu Ala Gly Ile Gly Ile Leu Thr Val
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Cys Leu Thr Ser Thr Val Gln Leu Val
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

His Leu Tyr Gln Gly Cys Gln Val Val
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Ile Phe Gly Ser Leu Ala Phe Leu
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ile Ile Ser Ala Val Val Gly Ile Leu
1               5
```

```
<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Pro Leu Thr Ser Ile Ile Ser Ala Val
1               5

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Val Met Ala Gly Val Gly Ser Pro Tyr Val
1               5                   10

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Val Leu Val Lys Ser Pro Asn His Val
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Glu Leu Val Ser Glu Phe Ser Arg Met
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Tyr Leu Ser Gly Ala Asn Leu Asn Leu
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 20

Gly Pro Leu Thr Pro Leu Pro Val
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ser Leu Leu Met Trp Ile Thr Gln Cys
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Lys Ala Leu Phe Ala Gly Pro Pro Val
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Tyr Leu Glu Thr Phe Arg Glu Gln Val
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Leu Gln Ser Pro Lys Ser Pro Leu
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Val Leu Leu Lys Leu Arg Arg Pro Val
1               5

<210> SEQ ID NO 26
<211> LENGTH: 9
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 26

Glu Leu Tyr Ile Pro Ser Val Asp Leu
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Leu Leu Met Trp Ile Thr Gln Val
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ile Leu Ala Lys Phe Leu His Trp Leu
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Thr Ala Pro Pro Val His Asn Val
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Phe Leu Trp Gly Pro Arg Ala Leu Val
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Phe Met Trp Gly Asn Leu Thr Leu Ala
1               5
```

```
<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Leu Val Asp Asp Phe Leu Leu Val
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

His Leu Ser Thr Ala Phe Ala Arg Val
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Leu Ser Leu Leu Met Trp Ile Thr
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Glu Leu Trp Thr His Ser Tyr Lys Val
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Lys Val Ala Glu Leu Val His Phe Leu
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37
```

Tyr Ile Phe Ala Thr Cys Leu Gly Leu
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

His Leu Tyr Ile Phe Ala Thr Cys Leu
1               5

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Met Leu Met Ala Gln Glu Ala Leu Ala Phe Leu
1               5                   10

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ser Thr Leu Glu Lys Ile Asn Lys Thr
1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Lys Ala Ser Glu Lys Ile Phe Tyr Val
1               5

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ser Leu Leu Met Trp Ile Thr Gln Cys Phe Leu
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic

```
                          peptide

<400> SEQUENCE: 43

Glu Leu Thr Leu Gly Glu Phe Leu Lys Leu
1               5                   10

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Leu Thr Leu Gly Glu Phe Leu Lys Leu
1               5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ser Leu Leu Glu Lys Arg Glu Lys Thr
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Thr Leu Gly Glu Asp Asp Pro Trp Leu
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Lys Leu Gly Leu Lys Pro Leu Glu Val
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Tyr Leu Trp Thr Ser Ala Lys Asn Thr
1               5

<210> SEQ ID NO 49
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ser Thr Ala Pro Pro Ala His Gly Val
1               5

<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Met Gly Ser Glu Glu Leu Arg Leu
1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ser Leu Gly Ser Pro Val Leu Gly Leu
1               5

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Tyr Leu Phe Phe Tyr Arg Lys Ser Val
1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Cys Gln Gln Glu Glu Thr Phe Leu Leu
1               5

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Thr Leu Ala Lys Phe Ser Pro Tyr Leu
1               5
```

```
<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asn Leu Thr His Val Leu Tyr Pro Val
1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ser Thr Phe Lys Asn Trp Pro Phe Leu
1               5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ser Leu Leu Gln His Leu Ile Gly Leu
1               5

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Phe Leu Asp Gln Arg Val Phe Phe Val
1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Phe Leu Asp Gln Arg Val Phe Val Val
1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 60

Phe Leu Asp Gln Val Ala Phe Val Val
1               5

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Leu Asp Arg Glu Gln Leu Tyr Leu
1               5

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Val Met Gln His Leu Leu Ser Pro Leu
1               5

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gln Gln Thr His Gly Ile Thr Arg Leu
1               5

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Leu Gln Pro Leu Ser Gly Pro Gly Leu
1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Thr Leu Asp Arg Asp Ser Leu Tyr Val
1               5

<210> SEQ ID NO 66
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 66

Gln Leu Tyr Leu Glu Leu Ser Gln Leu
1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Lys Val Leu Glu Tyr Val Ile Lys Val
1               5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Lys Val Ala Asp Leu Val Gly Phe Leu
1               5

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ser Ile Ile Asn Phe Glu Lys Leu
1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Lys Thr Trp Gly Gln Tyr Trp Gln Val
1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Val Leu Asp Gly Leu Asp Val Leu Leu
1               5
```

```
<210> SEQ ID NO 72
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
cagcagcaaa atcaagt                                                     17

<210> SEQ ID NO 73
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gaagaatgtg agtgtgc                                                     17

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
atcggtgctg ccgatggg                                                    18

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
tgaagttctc attctcgttt ggc                                              23

<210> SEQ ID NO 76
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gagccgtacg tgatgccg                                                    18

<210> SEQ ID NO 77
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
tcattgacgg cgaagtgg                                                    18

<210> SEQ ID NO 78
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
atcttctgcc ctcctggttt                                                   20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
atttgcaacc gcataccttc                                                   20

<210> SEQ ID NO 80
<211> LENGTH: 15
<212> TYPE: PRT
<213> ORGANISM: Drosophila nodaviridae virus

<400> SEQUENCE: 80

Met Val Asn Asn Ile Lys Pro Arg Arg Gln Arg Ser Gln Arg Val
1               5                   10                  15

<210> SEQ ID NO 81
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Val Asn Asn Ile Lys Pro Lys Arg Gln Arg Pro Gln Val
1               5                   10

<210> SEQ ID NO 82
<211> LENGTH: 15
<212> TYPE: PRT
<213> ORGANISM: Flock House virus

<400> SEQUENCE: 82

Met Val Asn Asn Ile Lys Pro Arg Arg Gln Arg Ala Gln Arg Val
1               5                   10                  15

<210> SEQ ID NO 83
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ala Ala Glu Gly Leu Asp Thr Gln Arg Phe Ser Gly
1               5                   10
```